US011655447B2

(12) United States Patent
Talaat

(10) Patent No.: US 11,655,447 B2
(45) Date of Patent: May 23, 2023

(54) **GLOBAL GENE REGULATORS (GGR) AS VACCINE CANDIDATES AGAINST *PARATUBERCULOSIS***

(71) Applicant: Wisconsin Alumni Research Foundation, Madison, WI (US)

(72) Inventor: Adel M. Talaat, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

(21) Appl. No.: 17/221,605

(22) Filed: Apr. 2, 2021

(65) Prior Publication Data

US 2021/0246416 A1 Aug. 12, 2021

Related U.S. Application Data

(60) Continuation of application No. 16/718,892, filed on Dec. 18, 2019, now Pat. No. 10,968,425, which is a division of application No. 15/492,553, filed on Apr. 20, 2017, now Pat. No. 10,544,389, which is a continuation of application No. 14/193,818, filed on Feb. 28, 2014, now Pat. No. 9,663,758.

(60) Provisional application No. 61/777,907, filed on Mar. 12, 2013.

(51) Int. Cl.
| | |
|---|---|
| *C12N 1/20* | (2006.01) |
| *C12Q 1/689* | (2018.01) |
| *C07K 14/195* | (2006.01) |
| *C07K 14/35* | (2006.01) |
| *C12N 1/36* | (2006.01) |
| *G01N 33/569* | (2006.01) |
| *A61K 39/04* | (2006.01) |
| *C12N 15/10* | (2006.01) |
| *C12N 15/113* | (2010.01) |
| *A61K 39/00* | (2006.01) |
| *C12R 1/32* | (2006.01) |

(52) U.S. Cl.
CPC ............... *C12N 1/20* (2013.01); *A61K 39/04* (2013.01); *C07K 14/195* (2013.01); *C07K 14/35* (2013.01); *C12N 1/36* (2013.01); *C12N 15/1031* (2013.01); *C12N 15/1136* (2013.01); *C12Q 1/689* (2013.01); *G01N 33/5695* (2013.01); *A61K 2039/522* (2013.01); *A61K 2039/552* (2013.01); *C12N 1/205* (2021.05); *C12Q 2600/156* (2013.01); *C12R 2001/32* (2021.05)

(58) Field of Classification Search
None
See application file for complete search history.

(56) References Cited

U.S. PATENT DOCUMENTS

2011/0243992 A1  10/2011  Kernodle

FOREIGN PATENT DOCUMENTS

| GB | 2389364 | 12/2003 | |
|---|---|---|---|
| WO | 0011214 A1 | 3/2000 | |
| WO | 2007059256 A2 | 5/2007 | |
| WO | 2007084353 A2 | 7/2007 | |
| WO | 2009087688 A2 | 7/2009 | |
| WO | 2010025462 A1 | 3/2010 | |
| WO | 2011012662 A1 | 2/2011 | |
| WO | WO-2011012662 A1 * | 2/2011 | ............. A61K 39/04 |

OTHER PUBLICATIONS

Alonso-Hearn, M., Eckstein, T. M., Sommer, S., and Bermudez, L. E.; A *Mycobacterium avium* subsp. *paratuberculosis* LuxR regulates cell envelope and virulence. Innate Immunity 2010; vol. 16:235-247.
Coussens, P. M., Colvin, C. J., Wiersman, K., et al. Gene expression profiling of peripheral blood mononuclear cells from cattle infected with *Mycobacterium paratuberculosis*. Infectious Immunity 2002; vol. 70:5494-5502.
Coussens, P. M., Jeffers, A. and Colvin, C.; Rapid and transient activation of gene expression in peripheral blood mononuclear cells from Johne's disease positive cows exposed to *Mycobacterium paratuberculosis* in vitro. Microbial.pathogenesis 2004; vol. 36:93-108.
Ghosh, P., Wu, C. W., and Talaat, A. M.; Key Role for the Alternative Sigma Factor, SigH, in the Intracellular Life of *Mycobacterium avium* subsp. *paratuberculosis* during Macrophage Stress. Infection and Immunity. Jun. 2013; vol. 81(6):2242-2257.
Ghosh, P., Steinberg, H. and Talaat, A.M., Virulence and Immunity Orchestrated by the Global Gene Regular, sigL, in *Micobacterium avium* subsp. *paratuberculosis*. Infection and Immunity Jul. 2014; vol. 82(7). American Society for Microbiology.
Hines, M.E., Tumquist, S.E., Ilha, M.R.S. et al.; Evaluation of novel oral vaccine candidates and validation of a caprine model of Johne's disease; Frontiers in Cellular and Infection Microbiology. Mar. 2014 vol. 4(26):pp. 1-14.
Janagama, H. K., Lamont, E. A., George, S., Bannantine, J. P., et al.; Primary transcriptomes of *Mycobacterium avium* subsp. *paratuberculosis* reveal proprietary pathways in tissue and macrophages. BMC Genomics 2010; vol. 11:561.
Manganelli, R., Voskuil, M. I., Schoolnik, G. K., Dubnau, E., Gomez, M. and Smith, I.; Role of the exliacytoplasmic-function sigma Factor sigma(H) in *Mycobacterium tuberculosis* global gene expression. Mol. Microbiol. 2002 vol. 45:365-374.

(Continued)

*Primary Examiner* — Brian Gangle
(74) *Attorney, Agent, or Firm* — Quarles & Brady LLP

(57) ABSTRACT

Described herein is a *Mycobacterium* mutant, comprising at least one mutation in at least one gene sequence encoding global gene regulators (GGRs) selected from the group consisting of sigH, sigL, sigE, ECF-1, and mixtures thereof, wherein the GGR gene is at least partially inactivated. Described herein also is a vaccine based on the mutant and a method of differentiating between subjects that have been infected with *Mycobacterium* and subjects that have not been infected with *Mycobacterium* or have been vaccinated with a *Mycobacterium* vaccine.

22 Claims, 12 Drawing Sheets

Specification includes a Sequence Listing.

(56) References Cited

OTHER PUBLICATIONS

Mehra, S., Golden, N. A., Stuckey, K., Didier, P. J., et al.; The *Mycobacterium tuberculosis* stress response factor SigH is required for bacterial burden as well as immunopathology in primate lungs. J.Infect.Dis. 2012; vol. 205:1203-1213.

National Animal Health Monitoring System 2008. Johne's Disease on U.S. Dairies, 1991-2007. USDA-APHIS Veterinary Services, Ft. Collins, CO. 2008.

Paget, M. S., Kang, J. G., Roe, J. H., and Buttner, M. J.; SigmaR, an RNA polymerase sigma factor that modulates expression of the thioredoxin system in response to oxidative stress in Streptomyces coelicolor A3(2). EMBO J. 1998 vol. 17:5776-5782. doi:10.1093/emboj/17.19.5776 [doi].

Settles, E.W., Kink, J.A., Talaat, A. Pan-Genome Screen for Live Attenduated Vaccines against Johne's Disease. Vaccine. Apr. 2014 vol. 32(18):2062-2069 Elsevier Ltd.

Weiss, D. J., Evanson, O. A., Deng, M. and Abrahamsen, M. S.; Sequential patterns of gene expression by bovine monocyte-derived macrophages associated with ingestion of mycobacterial organisms. Microb.Pathog. 2004 vol. 37:215-224.

Weiss, D. J., Evanson, O. A., Deng, M., and Abrahamsen, M. S.; Gene expression and antimicrobial activity of bovine macrophages in response to *Mycobacterium avium* subsp. *paratuberculosis*. Vet. Pathol. 2004 vol. 41:326-337.

Wu, C. W., Schmoller, S. K., Shin, S. J., and Talaat, A. M.; Defining the stressome of *Mycobacterium avium* subsp *paratuberculosis* in vitro and in naturally infected cows. Journal of Bacteriology 2007; vol. 189: 7877-7886.

Wu, C. W., Schmoller, S. K., Bannantine, J. P., Eckstein, T. M.; et al.; A novel cell wall lipopeptide is important for biofilm formation and pathogenicity of *Mycobacterium avium* subspecies *paratuberculosis*. Microb. Pathog. 2009 vol. 46: 222-230.

Zhu, X., Tu, Z. J., Coussens,P. M., Kapur, V., Janagama, H., et al.; Transcriptional analysis of diverse strains *Mycobacterium avium* subspecies *paratuberculosis* in primary bovine monocyte derived macrophages. Microbes Infect. 2008 vol. 10: 1274-1282.

Ellis, R. W. "New Technologies for Making Vaccines," "Vaccines" Plotkin, S.A. et al. (eds) published by W. B. Saunders company (Philadelphia) in 1988, pp. 568-575.

Hahn et al., J. Bacteriol., 187:7062-7071, 2005.

Brosch et al., Trends in Microbiol., 9:452-158, 2001.

Kreider et al., Cancer, 46:480-187, 1980.

Chambers et al. Vaccine, 22:1063-1071, 2004.

Manganelli, et al., The *Mycobacterium tuberculosis* ECF Sigma Factor sigmaE: Role in Global Gene Expression and Survival in Macrophages, Molecular Microbiology, 2001, 41(2):423-437.

Pando, et al., Immunogenicity and Protection Induced by a *Mycobacterium tuberculosis* sigE Mutant in a BALB/c Mouse Model of Progressive Pulmonary Tuberculosis, Infection and Immunity, 2010, 78(7):3168-3176.

Sadagopal, et al., Reducing the Activity and Secretion of Microbial Antioxidants Enhances the Immunogenicity of BCG, PLoS ONE, 2009, 4(5):e5531, pp. 1-12.

Sechi, et al., Genome and Transcriptome Scale Portrait of Sigma Factors in *Mycobacterium avium* subsp. *paratuberculosis*, Infection, Genetics and Evolution, 2007, 7(4):424-432.

PCT International Search Report and Written Opinion, PCT/US2014/020248, dated Sep. 16, 2014, 21 pages.

Chen J.-W.et al: "Immunogenicity and protective efficacy of the *Mycobacterium avium* subsp. *paratuberculosis* attenuated mutants against challenge in a mouse model", Vaccine, vol. 30, No. 19, Apr. 1, 2012, pp. 3015-3025, XP055443616.

Comincini S. et al: "Rapid identification of *Mycobacterium tuberculosis* and *Mycobacterium avium* by polymerase chain reaction and restriction enzyme analysis within sigma factor regions", Microbiologica (Pavia), vol. 21, No. 4, Oct. 1998, pp. 391-395, XP009504192.

Obata S. et al: "Association of rpoB mutations with rifampicin resistance in *Mycobacterium avium*", International Journal of Antimicrobial Agents, vol. 27, No. 1, Jan. 1, 2006, pp. 32-39, XP027935891.

Wu Q.-.L et al: "A Mycobacterial extracytoplasmatic Sigma factor involved in survival following stress", Journal of Bacteriology, vol. 179, No. 9, May 1, 1997, pp. 2922-2929,XP002188920.

Whittington R. J. et al: "Comparative immunological and microbiological aspects of paratuberculosis as a model mycobacterial infection", Veterinary Immunology and Immunopathology, vol. 148, No. 1 , Jul. 15, 2012, pp. 29-47, XP028931251.

\* cited by examiner

FIG. 5A
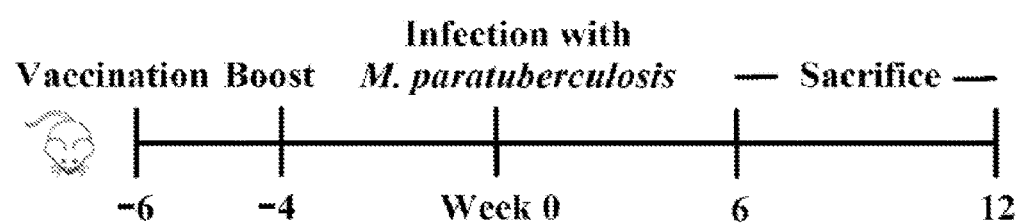
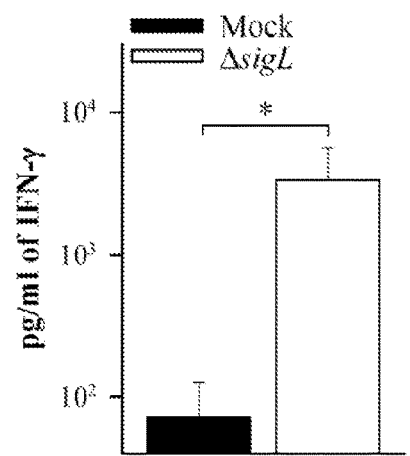
FIG. 5B
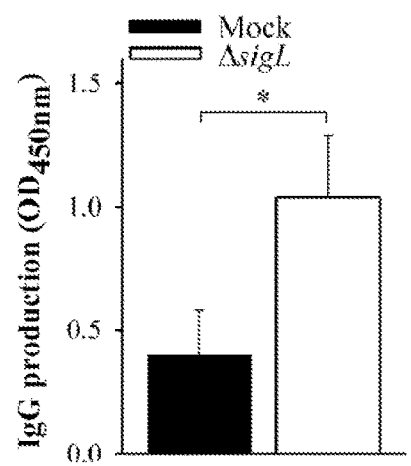
FIG. 5C

FIG. 7A
FIG. 7B
FIG. 7C
FIG. 7D
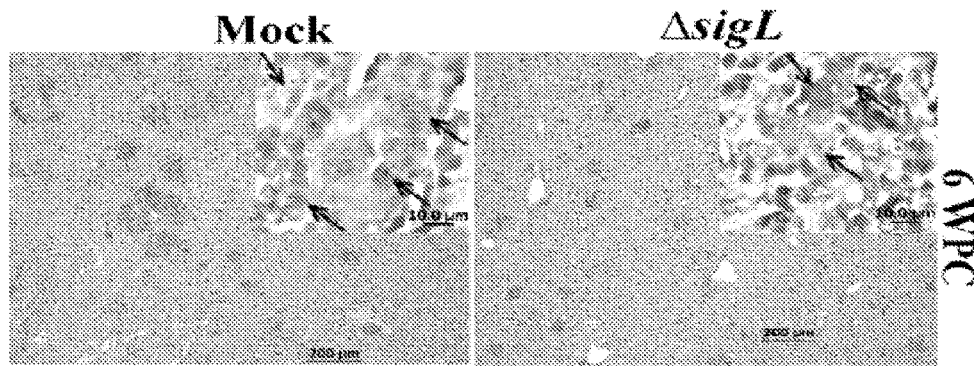
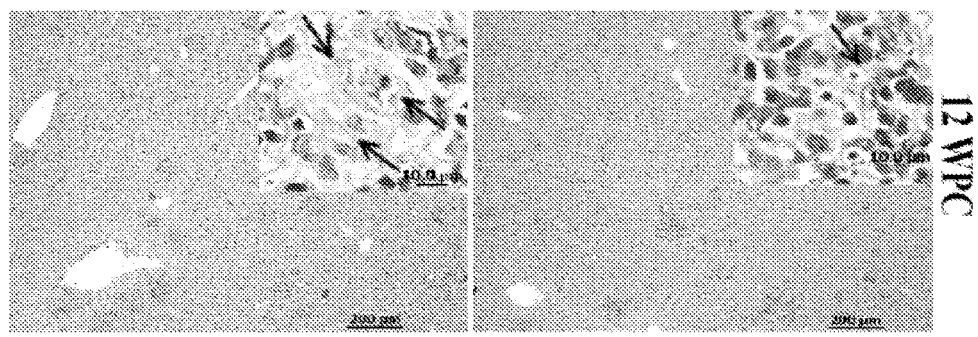
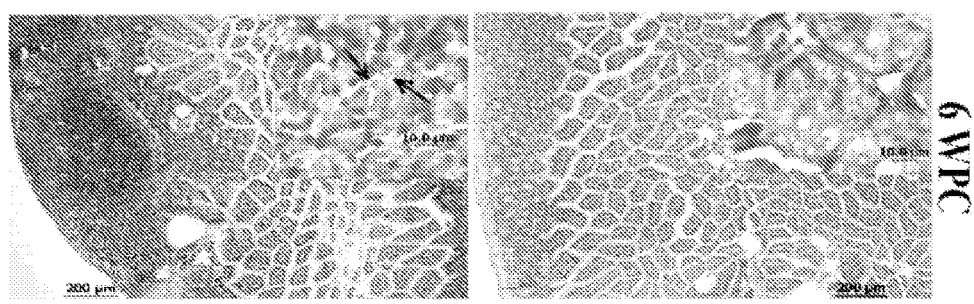
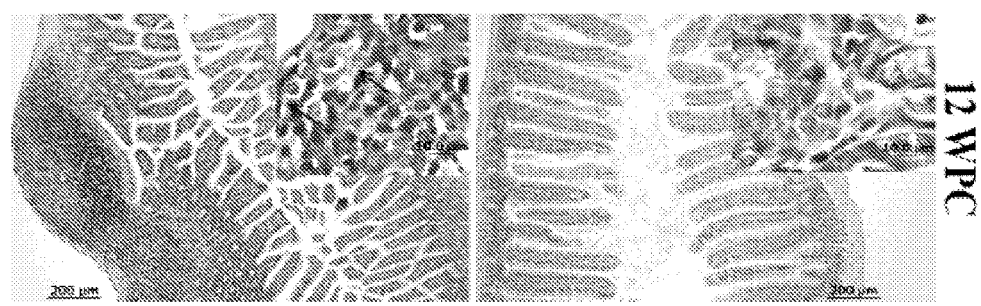

GLOBAL GENE REGULATORS (GGR) AS VACCINE CANDIDATES AGAINST PARATUBERCULOSIS

CROSS-REFERENCE TO RELATED APPLICATION(S)

This application is a continuation of U.S. patent application Ser. No. 16/718,892, filed Dec. 18, 2019, which is issuing as U.S. Pat. No. 10,968,425 on Apr. 6, 2021, which is a divisional of U.S. patent application Ser. No. 15/492,553, filed Apr. 20, 2017, now U.S. Pat. No. 10,544,389, issued Jan. 28, 2020, which is a continuation of U.S. patent application Ser. No. 14/193,818 filed Feb. 28, 2014, now U.S. Pat. No. 9,663,758, issued May 30, 2017, which claims priority to U.S. Patent Application 61/777,907, filed Mar. 12, 2013, each of which is incorporated by reference in its entirety.

STATEMENT REGARDING FEDERALLY SPONSORED RESEARCH OR DEVELOPMENT

This invention was made with government support under 14-CRHF-0-6055 awarded by the USDA/NIFA. The government has certain rights in the invention.

REFERENCE TO A SEQUENCE LISTING SUBMITTED VIA EFS-WEB

The content of the ASCII text file of the sequence listing named "960296_01676_ST25.txt" which is 6.05 kb in size was created on Feb. 28, 2014 and electronically submitted via EFS-Web herewith the application is incorporated herein by reference in its entirety.

BACKGROUND

*Mycobacterium avium* subspecies *paratuberculosis* (a.k.a. *M. paratuberculosis*) is the etiological agent of Johne's disease, a chronic enteritis of domestic and wild animals, especially ruminants. Johne's disease (JD) has been reported on every continent (1-3), and is considered one of the greatest causes of economic hardship to the ruminant industries (4). More than two thirds of the U.S. dairy herds are infected with JD (5) and this wide distribution of the disease, reduced milk production and premature culling of infected animals together causes severe economic losses estimated to be over $200 million a year for the dairy industry (6,7).

Majority of the *M. paratuberculosis* infection occurs through fecal-oral route and the mycobacteria are endocytosed by enterocytes and M cells in the Peyer's patches of the ileum (8,9). After subsequent internalization by subepithelial and intraepithelial macrophages, *M. paratuberculosis* is able to survive and persist within the cells (10) using mechanisms that are not completely understood. Several studies examined gene expression patterns and host defense mechanisms of bovine macrophages from naturally infected cows (11), peripheral blood mononuclear cells (PBMC) (12) or monocytes-derived macrophages (MDMs) (13,14) following infection with *M. paratuberculosis*. Alternatively, our group characterized the general and specific stress responses of *M. paratuberculosis* under various in vitro conditions as well as the transcriptomes of *M. paratuberculosis* in fecal samples from diseased cows (15).

Survival of *M. paratuberculosis* in environmental samples (16), macrophages (17) and animal models (18,19) is well-documented, however, the genetic basis for this survival remains unknown. Reports employing a large-scale screening of *M. paratuberculosis* mutants in relevant animal models (20,21) provided some insights into virulence of this organism with the identification of novel virulence factors associated with biofilm formation (22) and epithelial cell invasion (23). Recently, Zhu, et al. analyzed intracellular *M. paratuberculosis* gene expression patterns in bovine MDMs using SCOTS (selective capture of transcribed sequences), identifying similar patterns of responses to oxidative stress, metabolic activity, and cell survival among *M. paratuberculosis* with distinct host origins (24). The same group further analyzed the expression profiles of *M. paratuberculosis* isolated from naturally infected bovine tissues, identifying tissue-specific pathways (25). However, no comprehensive study has been conducted to clarify the relationship between *M. paratuberculosis* gene expression and specific host microenvironments following macrophage infection.

The current vaccine has a limited use to farmers in some regions (e.g. a few European countries) because of its inability to reduce *M. ap* shedding in feces of infected animals, the main source for spreading JD. There is only one vaccine (Mycopar®, Boehringer Ingelheim) approved for limited use in the USA. This vaccine causes significant granuloma formation at the site of inoculation 21, which persists throughout the animal's life, increasing the possibility for tissue condemnation at the slaughterhouse.

Despite the ability of this vaccine to induce cell mediated immunity in animals[17], shedding of *M. ap* from vaccinated animals continues to cause a problem for transmitting the disease to naïve animals (5,22). In sheep, some animals both shed *M. ap* and died from multi-bacillary form of JD despite being vaccinated (23). In a long-term study of the effect of killed vaccine on dairy herds to reduce the transmission of the disease, no significant difference in prevalence was found between vaccinated and non-vaccinated herds (22). In another study of commercial JD vaccines, cross reactivity to bovine tuberculosis was prominent, further hampering efforts for controlling tuberculosis in farm animals (24,25). More efforts are needed to better understand the pathogenesis of JD and to plan an effective control strategy.

The present invention starts with a goal to gain insights into how *M. paratuberculosis* respond to the intracellular microenvironments of macrophages, the primary site for mycobacterial persistence within the host, using targeted mutagenesis and an array of transcriptome analyses. In this study, the inventors took advantage of analytical microscopy to define the phagosome environment of *M. paratuberculosis*-containing macrophages in association with the expression profile of mycobacterial bacilli using DNA microarrays. The analysis suggested key changes in the metabolic pathways of *M. paratuberculosis* once the bacteria encounter active macrophages and the activation of various alternative sigma factors (Global Gene Regulators, GGRs) that could help *M. paratuberculosis* survive the hostile intracellular environment of macrophages. One such alternative GGR, sigH, has been shown to contribute to the resistance encountered during variable environmental stress conditions, such as temperature and oxidative stress in *M. tuberculosis* (26, 27). However, the basis of transcriptional regulation of sigH remains elusive in *M. paratuberculosis*.

The inventors therefore sought to define the gene regulatory network under control of GGRs, for example, sigH, sigL, sigE and ECF-1 in *M. paratuberculosis*. Accordingly, they confirmed a role for these key GGRs activated inside macrophages in defending *M. paratuberculosis* against thiol-specific oxidative stress and characterized the effect of these GGRs on global transcriptome in *M. paratuberculosis*. Based on the results, the inventor envisions that the GGR mutants could play an important role in designing effective vaccines against mycobacterial infections.

BRIEF SUMMARY OF THE INVENTION

In its first aspect, the present invention relates to a *Mycobacterium* mutant, comprising at least one mutation in at least one gene sequence encoding global gene regulators (GGRs) selected from the group consisting of sigH, sigL, sigE, ECF-1, and mixtures thereof, wherein the GGR gene is at least partially inactivated.

In some embodiments, the *Mycobacterium* is selected from the group consisting of *Mycobacterium avium* subspecies *paratuberculosis* (*M. ap*), *Mycobacterium bovis* (*M. bovis*), *Mycobacterium tuberculosis* (*M. tuberculosis*), *Mycobacterium avium* subsp. *avium* (*M. avium*), and mixtures thereof. Preferably, the *Mycobacterium* is *M. ap, M. bovis,* or *M. tuberculosis*.

In some embodiments, the GGR is *M. ap* sigH (SEQ ID NO:1) or a sequence substantially identical to SEQ ID NO: 1. In some embodiments, the GGR is *M. ap* sigL (SEQ ID NO:2) or a sequence substantially identical to SEQ ID NO:2. In some embodiments, the GGR is *M. ap* sigE (SEQ ID NO:3) or a sequence substantially identical to SEQ ID NO:3. In some embodiments, the GGR is *M. ap* ECF-1 (SEQ ID NO:4) or a sequence substantially identical to SEQ ID NO:4. In other embodiments, the GGR is *M. ap* sigB (SEQ ID NO:5) or a sequence substantially identical to SEQ ID NO:5.

In some embodiments, the inactivation of the GGR genes is achieved by at least partial deletion of the gene sequence encoding GGRs. Preferably, the inactivation is achieved by a complete deletion of the gene sequence encoding GGRs.

In some embodiments, the inactivation of the GGR genes is achieved by at least partial transposon insertion of the gene sequence encoding GGRs. Preferably, the inactivation is achieved by a complete transposon insertion of the gene sequence encoding GGRs.

In some embodiments, the inactivation of the GGR genes is achieved by at least partial anti-sense construct of the gene sequence encoding GGRs. Preferably, the inactivation is achieved by a complete anti-sense construct of the gene sequence encoding GGRs.

In its second aspect, the present invention relates to an isolated mycobacterial organism comprising a *Mycobacterium* mutant described herein.

In its third aspect, the present invention relates a *Mycobacterium* vaccine comprising a *Mycobacterium* mutant described herein. In some embodiments, the vaccine may also comprise the *Mycobacterium* organism described above.

In some embodiments, the vaccine is physically inactivated. Preferably, the vaccine is heat inactivated.

In some embodiments, the vaccine is chemically inactivated. Preferably, the vaccine is formaldehyde inactivated.

In other embodiments, the vaccine is a live attenuated vaccine.

In its fourth aspect, the present invention relates to a method of differentiating between subjects that have been infected with *Mycobacterium* and subjects that have not been infected with *Mycobacterium* or have been vaccinated with a *Mycobacterium* vaccine.

In one embodiment, the method comprises the steps of identifying a sequence that is specific to a *Mycobacterium* mutant and is not found in the wild-type *Mycobacterium* strain; and detecting the presence of the sequence in the subject. In another embodiment, the method comprises the steps of identifying a sequence that is specific to a wild-type *Mycobacterium* strain and is not found in the *Mycobacterium* mutant; and detecting the presence or the quantity of the sequence in the subject.

In a preferred embodiment, the *Mycobacterium* mutant is a mutant described herein. In another preferred embodiment, the detection is made by using probes or primers complementary to the *Mycobacterium* mutant in an amplification reaction. More preferably, the amplification is the loop-mediated isothermal amplification (LAMP).

BRIEF DESCRIPTION OF THE DRAWINGS

FIG. 2A. Survival of *M. avium* subsp. *paratuberculosis* strains in bovine macrophages. Naive MDM cells were infected with ΔsigH mutant and wild-type *M. avium* subsp. *paratuberculosis* strains. Cells were lysed at 1, 4, and 8 days postinfection, and numbers of viable bacilli were determined by CFU plating. The survival levels at 4 and 8 days were relative to the viable counts of bacterial strains at day 1. Survival data represent the average of macrophage infections collected from three different donor animals with significance levels in Student's t test (*, $P<0.05$). Error bars represent the standard deviations.

FIG. 2B. Survival of *M. avium* subsp. *paratuberculosis* strains in bovine macrophages. IFN-γ-pretreated MDM cells were infected with ΔsigH mutant and wild-type *M. avium* subsp. *paratuberculosis* strains. Cells were lysed at 1, 4, and 8 days postinfection, and numbers of viable bacilli were determined by CFU plating. The survival levels at 4 and 8 days were relative to the viable counts of bacterial strains at day 1. Survival data represent the average of macrophage infections collected from three different donor animals with significance levels in Student's t test (*, $P<0.05$). Error bars represent the standard deviations.

FIG. 3B. Virulence of *M. avium* subsp. *paratuberculosis* K10 and the ΔsigH mutant in mice. Mice groups (n=15) were inoculated with ~2×10$^8$ CFU/mouse of *M. avium* subsp. *paratuberculosis* wild-type strain or the ΔsigH mutant via intraperitoneal injection. Spleens were collected at 3, 6, and 12 wpi (n=5 mice/group/time point) and cultured for bacterial counts. Colony counts for each group are represented by scattered plots accompanied with a median line. Organs with significant difference in bacterial load were denoted with * for P values of <0.05 or ** for P values of <0.01).

FIG. 5A. Analysis of immune responses in immunized mice before challenge. Scheme illustrating the immunization study. C57BL/6 mice received a total of 2 doses, each containing ~2×10⁶ CFU *M. avium* subsp. *paratuberculosis* ΔsigL by s.c injection. Mock group received PBS buffer. Following vaccination, both groups of mice were challenged with wild-type *M. avium* subsp. *paratuberculosis* strain as described above. After 6 weeks post-immunization (6PWI; week0 in the scheme) or 6 weeks post-challenge (WPC), mice (N=4-6) from each group were sacrificed for analysis of immune response.

FIG. 5B. Analysis of immune responses in immunized mice before challenge. Splenocytes (6PWI) were isolated and re-stimulated in vitro with Johnin PPD to measure IFN-γ levels from culture supernatant by ELISA after 48 h.

FIG. 5C. Analysis of immune responses in immunized mice before challenge. *M. avium* subsp. *paratuberculosis* specific antibody (anti-PPDj antibodies) in the mouse sera (6PWI) was detected by ELISA (OD 450 nm) using Horseradish peroxidase conjugated rabbit anti-mouse antibody. *p<0.05.

FIG. 7A. Pathological analysis of mice organs following vaccination. Photographs shows haematoxylin and eosin staining liver.

FIG. 7B. Pathological analysis of mice organs following vaccination. Photographs shows haematoxylin and eosin staining liver.

FIG. 7C. Pathological analysis of mice organs following vaccination. Photographs shows haematoxylin and eosin staining intestine section (100× magnification, scale bar=200 µm) from mock and *M. avium* subsp. *paratuberculosis* ΔsigL vaccinated animals following challenge with wild-type *M. avium* subsp. *paratuberculosis* strain at 6WPC and 12WPC. Ziehl-Neelsen staining of both liver and intestine displayed higher acid-fast bacilli (inset images; 1000× magnification, scale bar=10 µm) in the mock vaccinated animals compared to the ones that received *M. avium* subsp. *paratuberculosis* ΔsigL vaccination.

FIG. 7D. Pathological analysis of mice organs following vaccination. Photographs shows haematoxylin and eosin staining intestine section (100× magnification, scale bar=200 µm) from mock and *M. avium* subsp. *paratuberculosis* ΔsigL vaccinated animals following challenge with wild-type *M. avium* subsp. *paratuberculosis* strain at 6WPC and 12WPC. Ziehl-Neelsen staining of both liver and intestine displayed higher acid-fast bacilli (inset images; 1000× magnification, scale bar=10 µm) in the mock vaccinated animals compared to the ones that received *M. avium* subsp. *paratuberculosis* ΔsigL vaccination.

DESCRIPTION OF THE INVENTION

Figure 1A:
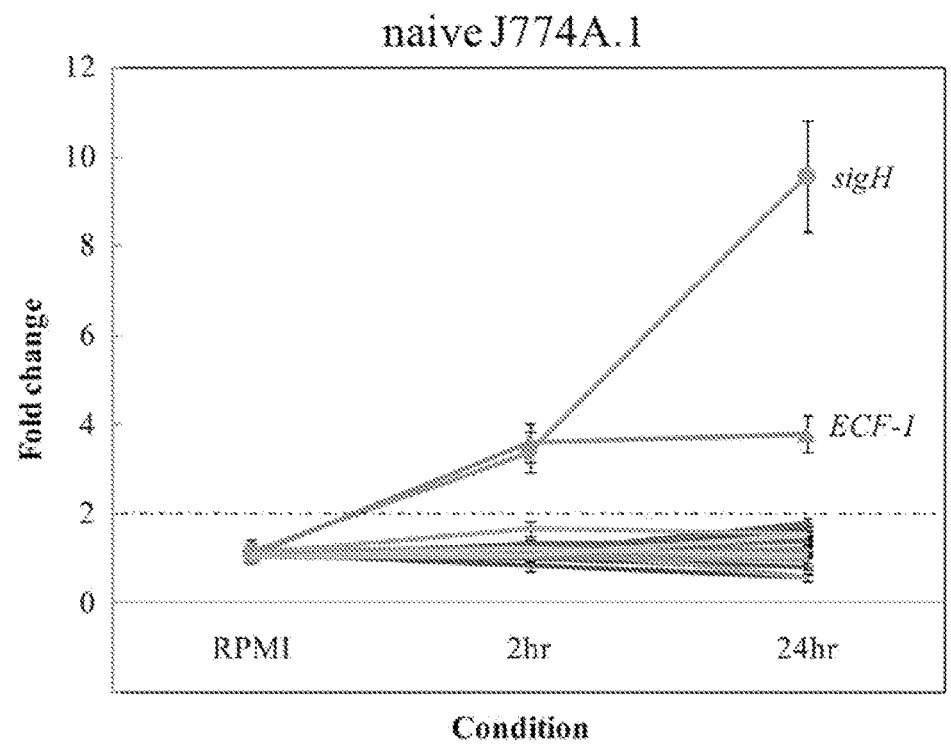
FIG. 1A. Temporal expression of *M. avium* subsp. *paratuberculosis* sigma factors within macrophages using DNA microarrays. A selected list of the *M. avium* subsp. *paratuberculosis* sigma factor genes are shown under naïve macrophages. Note that sigH and other ECF-1 (ECF-1 on the chart for clarity) were upregulated immediately after infection, followed by expression of sigE and sigB.

The present invention provides *Mycobacterium* mutants and a vaccine based on the mutants for successfully generating immune response to the infection by Mycobacteria, and in particular for generating immune response to infection caused by *Mycobacterium avium* subspecies *paratuberculosis* (*M. ap*). The present invention is based on the identification of the gene regulatory network under control of global gene regulators (GGRs) (e.g. sigma factors, transcriptional regulators). It is found that some of key GGRs can be genetically mutated to be activated inside macrophages in defending *M. paratuberculosis* against thiol-specific oxidative stress and characterized the effect of GGRs on global transcriptome in *M. paratuberculosis*. It is envisioned that a mutant with the deletion, inactivation or reduction of GGRs gene could provide strains capable of replication in hosts to generate enough protective immunity.

Definitions

A "*Mycobacterium*" as used herein, refers to microorganisms of the genus *Mycobacterium* (sometimes abbreviated as M. herein), from the family of Mycobacteriaceae. The particularly interested mycobacteria for the purpose of the present invention include members of *Mycobacterium avium* subspecies *paratuberculosis* (*M. ap*), *Mycobacterium bovis* (*M. bovis*), *Mycobacterium avium* subsp. *avium* avium), *M. bovis* BCG (the strain most often used for vaccination purposes), *Mycobacterium tuberculosis* (*M. tuberculosis*), which includes the species *M. tuberculosis* (the major cause of human tuberculosis), *M. africanum, M. microti, M. canetti,* and *M. pinnipedii*.

A "global gene regulator, GGR" refers to any protein needed for initiation of RNA synthesis, for example, "sigma factors" and "transcriptional regulators". They are bacterial transcription initiation factors that enable specific binding of RNA polymerase to gene promoters. RNA polymerase holoenzyme complex consists of core RNA polymerase and a GGR executes transcription of a DNA template strand. The specific GGR used to initiate transcription of a given gene will vary, depending on the gene and on the environmental signals needed to initiate transcription of that gene.

A "mutation" as used herein refers to a mutation in the genetic material (typically DNA), in particular a non-naturally occurring mutation, obtained via genetic engineering techniques. Mutations may include insertions, deletions, anti-sense constructs, substitutions (e.g., transitions, transversion), transpositions, inversions and combinations thereof. Mutations also include mutations upstream of the start codon, such as in the promoter region, particularly mutations within 30 nucleotides upstream of the start codon, as long as these mutations affect the levels and/or function of the gene product. Mutations may involve only a single nucleotide (e.g., a point mutation or a single nucleotide polymorphism) or multiple nucleotides.

In some embodiments, the mutation is a partial or complete deletion of the gene. In some embodiments, the mutation is introduced by inserting heterologous sequences into the gene of interest. In other embodiments, the mutation is introduced by replacing a portion of the wild-type gene or allele, or a majority of the wild-type gene or allele, with a heterologous sequence, or an engineered (e.g., manually altered, disrupted, or changed), non-functional, copy of the wild-type sequence. In some embodiments, the mutation is introduced by a partial or complete anti-sense construct, which refers to a DNA sequence complementary to a particular gene. When such construct is introduced in the genome, it will be transcribed in RNA and will be paired with the RNA of the gene it is complementary to. This complex of two RNA (double stranded RNA) will then be degraded so that no protein of the gene will be expressed.

Preferably, the mutation is done by deleting at least about 10%, at least about 20%, at least about 30%, at least about 50%, at least about 70% or at least 90% of the wild-type gene sequence. In other embodiments, the mutation is done by deleting the full wild-type sequence. In some other embodiments, the mutation may even include a deletion of more than 100% of the wild-type gene sequence (e.g., the full wild-type gene sequence may be deleted but also include one or more heterologous and/or non-functional nucleic acid sequences attached thereto or inserted therein).

Mutations could be silent, that is, no phenotypic effect of the mutation is detected. On the other hand, mutations may also cause a phenotypic change. For example, the expression level of the encoded product is altered, or the encoded product itself is altered. It is also called as the gene with the genetically engineered mutation encodes a gene product that has a reduced (knock-down) or absent (knock-out) functionality. This may be either because there is none or less of the gene product present than in the corresponding wild type strain, and/or because the gene product is not or only partially functional.

Thus, the mutations may influence expression levels of the gene product, stability of the gene product, encode defunct or nonsense gene products (e.g. by insertion of a stop codon), encode a different gene product, or any combination of these. For example, a mutation may result in a disrupted gene with decreased levels of expression of a gene product (e.g., protein or RNA) as compared to the wild-type strain (e.g., *M. ap*). A mutation may also result in an expressed protein with activity that is lower as compared to the activity of the expressed protein from the wild-type strain (e.g., *M. ap*). In some embodiments, the activity of the protein is reduced by 10%, 30%, 50%, 70%, 90% or more.

In specific embodiments of the present invention, mutations are conducted in at least one gene sequence encoding global gene regulators (GGRs). Such mutations result in at least partial inactivation of the function of the GGR genes. The term "function" as used herein is intended to mean the function of GGR gene sequences directly and/or indirectly attributable to the expression of the GGR genes. The "function" also refers to the function and/or activity of the proteins encoded by GGR genes as to their indirectly and/or directly attribution to infectious and/or inflammasome activation of mycobacteria.

The term "at least partially inactivated" as used herein, is meant to indicate a loss, interruption, or alteration of GGR genes function directly and/or indirectly attributable to the expression of GGR genes. It is also meant to indicate a loss, interruption, alteration of the infectious and/or inflammasome activation of the protein products encoded by GGR genes in mycobacteria. Preferably, "at least partially inactivated" relates to a loss of more than 10%, preferably more than 30%, more preferably more than 50%, more preferably more than 70%, most preferably more than 90% of the function directly and/or indirectly attributable to the expression of a GGR gene in mycobacteria. The "at least partially inactivation" may also include a inactivation of the full (100%) function of a GGR gene.

Partial and/or full inactivation of genes in mycobacteria for the purpose of the present invention can be achieved by any conventional method known in the art of gene mutation, e.g., recombinant insertion, transposon insertion, replacement, deletion, frameshift, anti-sense construct and/or homologous recombination. Preferably, the specific methods for partially and/or fully inactivating a GGR gene in mycobacteria is to delete more than 10%, preferably more than 30%, more preferably more than 50%, more preferably more than 70%, most preferably more than 90% of a GGR gene sequence.

The mechanism thereof is not vital to the invention, but typically may involve reduction or loss of transcription and/or translation of the affected gene, or only transcription/translation of a dysfunctional gene product. Genetically engineered mutations in a gene need not necessarily be in an exon or open reading frame, they can be in an intron or even be upstream of the start codon, as long as it affects the levels of the functional gene product. This can easily be checked, e.g. by Q-PCR for gene transcription levels. Functionality of a gene product can also be checked, as one of skill in the art would know, e.g. by providing a natural substrate to the affected enzyme. Of course, for the purpose of the present invention, the inactivation and the extent of inactivation can best be determined in direct comparison to a wild-type *Mycobacterium* or a *Mycobacterium* of the same strain under identical experimental conditions but comprising a full functional and expressed GGR gene.

The term "contiguous portions of a sequence" as used herein refers to a non-interrupted sequence of nucleic acids or amino acids also occurring in the same order in the sequence referred to. Particularly envisaged are contiguous portions having a length of at least 25%, 50%, 70%, 75%, 80% or 90% of the length of the reference sequence, and contiguous portions are typically at least 25 nucleic acids or at least 8 amino acids.

The term "sequence identity" as used herein refers to the extent that sequences are identical on a nucleotide-by-nucleotide basis or an amino acid-by-amino acid basis over a window of comparison. Nucleic acid and protein sequence identities can be evaluated by using any method known in the art. For example, the identities can be evaluated by using the Basic Local Alignment Search Tool ("BLAST"). The BLAST programs identity homologous sequences by identifying similar segments between a query amino or nucleic acid sequence and a test sequence which is preferably obtained from protein or nuclei acid sequence database. The BLAST program can be used with the default parameters or with modified parameters provided by the user.

The term "percentage of sequence identity" is calculated by comparing two optimally aligned sequences over the window of comparison, determining the number of positions at which the identical nucleic acid base (e.g., A, T, C, G) or the identical amino acid residue (e.g., Ala, Pro, Ser, Thr, Gly, Val, Leu, lie, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

The term "substantial identity" of polynucleotide sequences means that a polynucleotide comprises a sequence that has at least 25% sequence identity. Alternatively, percent identity can be any integer from 25% to 100%. More preferred embodiments include at least: 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98% or 99% compared to a reference sequence using the programs described herein; preferably BLAST using standard parameters, as described. These values can be appropriately adjusted to determine corresponding identity of proteins encoded by two nucleotide sequences by taking into account codon degeneracy, amino acid similarity, reading frame positioning and the like.

The term "substantial identity" of amino acid sequences for purposes of this invention normally means polypeptide sequence identity of at least 40%. Preferred percent identity of polypeptides can be any integer from 40% to 100%. More preferred embodiments include at least 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 98.7%, or 99%.

*Mycobacterium* Mutants

According to a first aspect, a *Mycobacterium* mutant is provided comprising at least one genetically engineered mutation in at lease one gene sequence encoding global gene regulators (GGRs), wherein the GGR gene is at least partially inactivated.

In some embodiments, the *Mycobacterium* is selected from the group consisting of *Mycobacterium avium* subspecies *paratuberculosis* (*M. ap*), *Mycobacterium bovis* (*M. bovis*), *Mycobacterium tuberculosis* (*M. tuberculosis*), *Mycobacterium avium* subsp. *avium* (*M. avium*), and mixtures thereof. Preferably, the *Mycobacterium* is *M. ap*.

In preferred embodiments, the GGR gene is selected from the group consisting of sigH, sigL, sigE, ECF-1, and mixtures thereof.

To inactivate a GGR gene in mycobacteria, one may partially or completely delete the sequence of the GGR gene. For example, one may insert heterologous sequences into the GGR gene. One may also replace a portion of the GGR gene or allele, or a majority of the GGR gene or allele, with a heterologous sequence, or an engineered (e.g., manually altered, disrupted, or changed), non-functional, copy of the wild-type sequence. Preferably, the mutation is done by deleting at least about 10%, at least about 20%, at least about 30%, at least about 50%, at least about 70% or at least 90% of the wild-type GGR gene sequence. More preferably, the mutation is done by deleting the full GGR sequence. In some other embodiments, the mutation may even include a deletion of more than 100% of the wild-type GGR gene sequence (e.g., the full wild-type gene sequence may be deleted but also include one or more heterologous and/or non-functional nucleic acid sequences attached thereto or inserted therein).

While these genes across different species of mycobacteria are expected, not all genes in each species have the identical sequences, locations, or functions. But based on sequence homology, one skilled person would be able to readily identify the corresponding (or equivalent) gene in other species. In a particular embodiment, the *Mycobacterium* is *M. paratuberculosis* strain which has 19 GGRs, as listed in Table 1 below.

TABLE 1

List of 19 sigma factors (global gene regulators, GGR) in *M. paratuberculosis* genome.

| Gene | Old locus tag* | Revised locus tag** | Gene length (bp) | Start nucleotide number* | End nucleotide number* | Start nucleotide number** | End nucleotide number** |
|---|---|---|---|---|---|---|---|
| sigA | MAP2820 | MAPK_0948 | 1530 | 3148633 | 3150162 | 1062326 | 1060797 |
| sigB | MAP2826 | MAPK_0942 | 999 | 3153258 | 3154256 | 1057701 | 1056703 |
| sigC | MAP1814 | MAPK_1954 | 1380 | 1991733 | 1993112 | 2219261 | 2217882 |
| sigD | MAP4275 | MAPK_4277 | 597 | 4742530 | 4743126 | 4745339 | 4745935 |
| sigE | MAP2557c | MAPK_1211 | 756 | 2874942 | 2875697 | 1335260 | 1336015 |
| sigF | MAP3406c | MAPK_0362 | 789 | 1613298 | 1614107 | 428572 | 429360 |
| sigF-like | MAP1474c | MAPK_2294 | 810 | 3781604 | 3782392 | 2596880 | 2597689 |
| sigG | MAP3621c | MAPK_0147 | 1101 | 4018733 | 4019833 | 191134 | 192234 |
| sigH | MAP3324c | MAPK_0444 | 807 | 3692929 | 3693735 | 517229 | 518035 |
| sigI | MAP0170 | MAPK_3598 | 858 | 173736 | 174593 | 4037249 | 4036392 |
| sigJ | MAP3446c | MAPK_0322 | 888 | 3825108 | 3825995 | 384969 | 385856 |
| sigL | MAP4201 | MAPK_4203 | 546 | 4670740 | 4671285 | 4673550 | 4674095 |
| sigM | MAP4337 | MAPK_4339 | 588 | 4818485 | 4819072 | 4821294 | 4821881 |
| ECF-1 | MAP0946c | MAPK_2822 | 924 | 975766 | 976689 | 3234298 | 3235221 |
| ECF-2 | MAP1770c | MAPK_1998 | 936 | 1932783 | 1933718 | 2277276 | 2278211 |
| ECF-3 | MAP2166 | MAPK_1602 | 891 | 2397944 | 2398834 | 1813051 | 1812161 |
| ECF-4 | MAP1757c | MAPK_2011 | 630 | 1919501 | 1920130 | 2290864 | 2291493 |
| ECF-5 | MAP4114c | MAPK_4116 | 1263 | 4584803 | 4586065 | 4588877 | 4587615 |
| ECF-6 | MAP4217 | MAPK_4219 | 540 | 4688035 | 4688574 | 4690845 | 4691384 |

*Annotations according to Li, et al., 2005 (35).
**Improved annotations according to the revised genome sequence of *M. paratuberculosis* (GenBank Accession No. AE016958) (38).
Bolded genes were up-regulated during macrophage survival and are potential vaccine mutants.

In the present invention, one of the preferred GGR genes is sigH. The term "sigH" as used herein refers to a gene which encodes a RNA polymerase sigma-H factor. In some embodiments, the sigH is the sigH (SEQ ID NO:1) of *M. paratuberculosis*. It has a size of 807 base pairs (bp) and is located at positions 517229 to 518035 of the *M. paratuberculosis* genomic sequence. In one specific embodiment, a *Mycobacterium* mutant comprises at least one mutation in *M. ap* sigH (SEQ ID NO: 1) or contiguous portions thereof, or sequences at least 90%, at least 95%, at least 98%, or at least 99% identical to SEQ ID NO: 1 or the contiguous portions thereof. Preferably, the mutation in sigH is at least partial deletion of the sigH gene, as characterized as "*M. paratuberculosis* ΔsigH". As a result of the deletion, the sigH gene is expressed at levels lower than the corresponding wild-type gene, or not expressed at all. Preferably, the expression level of sigH gene is so low as to have no effect or the expressed protein is non-functional.

Another preferred GGR gene is sigL (SEQ ID NO:2). The term "sigL" as used herein refers to a gene which encodes a Sigma-L-dependent transcriptional regulator. In some embodiments, the sigL is the sigL (SEQ ID NO:2) of *M. paratuberculosis*. It has a size of 546 base pairs (bp) and is located at positions 4673550 to 4674095 of the *M. paratuberculosis* genomic sequence. In one specific embodiment, a *Mycobacterium* mutant comprises at least one mutation in sigL (SEQ ID NO: 2) or contiguous portions thereof, or sequences at least 90%, at least 95%, at least 98%, or at least 99% identical to SEQ ID NO: 2 or the contiguous portions thereof. Preferably, the mutation in the sigL gene is at least partial deletion of the sigL gene, as characterized as "*M. paratuberculosis* ΔsigL". As a result of the deletion, the sigL gene is expressed at levels lower than the corresponding wild-type gene, or not expressed at all. Preferably, the expression level of sigL gene is so low as to have no effect or the expressed protein is non-functional.

Another preferred GGR gene is sigE (SEQ ID NO:3). The term "sigE" as used herein refers to a gene which encodes a RNA polymerase sigma-E factor. In some embodiments, the sigE is the sigE (SEQ ID NO:3) of *M. paratuberculosis*. It has a size of 756 base pairs (bp) and is located at positions 1335260 to 1336015 of the *M. paratuberculosis* genomic sequence. In one specific embodiment, a *Mycobacterium* mutant comprises at least one mutation in sigE (SEQ ID NO: 3) or contiguous portions thereof, or sequences at least 90%, at least 95%, at least 98%, or at least 99% identical to SEQ ID NO: 3 or the contiguous portions thereof. Preferably, the mutation in sigE gene is at least partial deletion of the sigE gene, as characterized as "*M. paratuberculosis* ΔsigE". As a result of the deletion, the sigE gene is expressed at levels lower than the corresponding wild-type gene, or not expressed at all. Preferably, the expression level of sigE gene is so low as to have no effect or the expressed protein is non-functional.

Another yet preferred GGR gene is ECF-1. The term "ECF-1" as used herein refers to a gene which encodes a RNA polymerase ECF sigma factor. In some embodiments, the ECF-1 is the ECF-1 (SEQ ID NO:4) of *M. paratuberculosis*. It has a size of 924 base pairs (bp) and is located at positions 3234298 to 3235221 of the *M. paratuberculosis* genomic sequence. In one specific embodiment, a *Mycobacterium* mutant comprises at least one mutation in ECF-1 (SEQ ID NO: 4) or contiguous portions thereof, or sequences at least 90%, at least 95%, at least 98%, or at least 99% identical to SEQ ID NO: 4 or the contiguous portions thereof. Preferably, the mutation in ECF-1 gene is at least partial deletion of the ECF-1 gene, as characterized as "*M. paratuberculosis* Δecf-1". As a result of the deletion, the ECF-1 gene is expressed at levels lower than the corresponding wild-type gene, or not expressed at all. Preferably, the expression level of ECF-1 gene is so low as to have no effect or the expressed protein is non-functional.

Another preferred GGR gene is sigB. The term "sigB" as used herein refers to a gene which encodes a RNA polymerase sigma-B factor. In some embodiments, the sigB is the sigB (SEQ ID NO:5) of *M. paratuberculosis*. It has a size of 999 base pairs (bp) and is located at positions 3153258 to 3154256 of the *M. paratuberculosis* genomic sequence. In one specific embodiment, a *Mycobacterium* mutant comprises at least one mutation in sigB (SEQ ID NO: 5) or contiguous portions thereof, or sequences at least 90%, at least 95%, at least 98%, or at least 99% identical to SEQ ID NO: 5 or the contiguous portions thereof. Preferably, the mutation in sigE gene is at least partial deletion of the sigB gene, as characterized as "*M. paratuberculosis* ΔsigB". As a result of the deletion, the sigB gene is expressed at levels lower than the corresponding wild-type gene, or not expressed at all. Preferably, the expression level of sigB gene is so low as to have no effect or the expressed protein is non-functional.

Also, in some embodiments, a *Mycobacterium* mutant comprises a combination of two or more of these genes that are mutated. For instance, both sigH and sigL genes are mutated, or sigH gene and one or two of sigL, sigE, sigB and ECF-1 genes are mutated. Additionally and/or alternatively, one or more of these genes may contain more than one mutation.

In some other embodiments, a *Mycobacterium* mutant may have further non-GGR mutations. One example of these further mutations includes additional mutations in other genes that function independent or dependent from GGRs in directly or indirectly causing mycobacteria infections. Other non-limiting examples of the further mutation sites, as described in the United States Patent Application Publication Number 2007/0134274, include gcpE, pstA, kdpC, papA2, impA, umaA1, fabG2_2, aceAB, mbtH2, lpqP, map0834c, cspB, lipN, map1634 MAP-1, MAP-2, MAP-3, MAP-4, MAP-5, MAP-6, MAP-7, MAP-8, MAP-9, MAP-10, MAP-11, MAP-12, MAP-13, MAP-14, MAP-15, MAP-16, MAP-17, or MAP-18 of *M. paratuberculosis*, or homologs of these genomic islands, and also include, as described in the United States Patent Application Publication Number 2007/0134708, MAV-1, MAV-2, MAV-3, MAV-4, MAV-5, MAV-6, MAV-7, MAV-8, MAV-9, MAV-10, MAV-11, MAV-12, MAV-13, MAV-14, MAV-15, MAV-16, MAV-17, MAV-18, MAV-19, MAV-20, MAV-21, MAV-22, MAV-23, or MAV-24, or homologs thereof.

According to the second aspect of the present invention, a *Mycobacterium* mutant may be defined at the protein (amino acid) level. Thus, the present invention provides an isolated mycobacterial protein, which is encoded by the gene sequence of a *Mycobacterium* mutant as described herein. The protein expressed by the mutant may have a lower activity and/or function as compared to the activity of the expressed protein from the wild-type strain (e.g., *M. ap*). In some embodiments, the activity and/or the function of the protein is reduced by 10%, 30%, 50%, 70%, 90% or more.

Vaccine

The third aspect of the present invention provides a vaccine based on the *Mycobacterium* mutants described herein. Specifically, in some embodiments, the *Mycobacterium* mutant comprises at least one mutation in at lease one gene sequence encoding global gene regulators (GGRs) described herein, wherein the GGR gene is at least partially inactivated. Preferably, the *Mycobacterium* is selected from the group consisting of *Mycobacterium avium* subspecies *paratuberculosis* (*M. ap*), *Mycobacterium bovis* (*M. bovis*), *Mycobacterium tuberculosis* (*M. tuberculosis*), and mixtures thereof. More preferably, the *Mycobacterium* is *M. ap*.

The GGR gene may be selected from the group consisting of a sequence of or sequence substantially identical to sigH (SEQ ID NO:1), sigL (SEQ ID NO:2), sigE (SEQ ID NO:3), ECF-1 (SEQ ID NO:4), sigB (SEQ ID NO:5) and mixtures thereof.

The vaccine of the present invention may be a suspension of live attenuated, or inactivated (killed) microorganisms comprising the mutants described herein. The types microorganisms may vary, such as viruses, bacteria, or rickettsiae of the microorganisms, or of other antigens such as antigenic proteins and other substances derived from them, administered for prevention, amelioration, or treatment of *Mycobacterium* infections.

In some embodiments, the vaccine is a live attenuated vaccine, wherein the *Mycobacterium* mutant or the organism thereof used for the invention is alive. By "alive", we mean the mutant or the organism thereof is capable of propagation in a subject, in particular in a mammalian subject. To be an effective live attenuated vaccine, the live mycobacteria must be attenuated to a degree not harmful to a subject in need thereof. Hence, the *Mycobacterium* mutant used for the invention is preferably non-virulent, i.e. the genes responsible for virulence have been inactivated, and does not evoke or at least evokes minor disease symptoms of a mycobacterial infection in a subject.

In some embodiments, the vaccine is an inactivated vaccine, wherein the *Mycobacterium* mutant or the organism thereof used for the invention is killed or inactivated. The advantage of an inactive vaccine is safety. The vaccine may be inactivated by any art-known method. For example, it may be inactivated by using chemical methods such as beta-propiolactone, thimerosal or (another mercury donating agent), formaldehyde, etc. The vaccine may be inactivated by applying physical methods such as heat, UV-light, microwaves etc. The vaccine may also be inactivated by using biological methods such as enzyme-based methods to kill or inactivate the bacteria and any other method as is commonly applied in the art.

In some other embodiments, the vaccine is an acellular vaccine, i.e., a cell-free vaccine prepared from the purified mycobacterial components of cell-free microorganisms, carrying less risk than whole-cell preparations.

Vaccination may be accomplished by administering nucleic acid sequence of the *Mycobacterium* mutant in a form of a DNA vaccine. A "DNA vaccine" or "immunogenic" or "immunological composition" is composed of at least one vector (e.g., plasmid) which may be expressed by the cellular machinery of the subject to be vaccinated or inoculated and of a pharmaceutically acceptable carrier, vehicle, or excipient. The nucleotide sequence of this vector encodes one or more immunogens, such as proteins or glycoproteins capable of inducing, in the subject to be vaccinated or inoculated, a cellular immune response (mobilization of the T lymphocytes) and an immune response.

The vaccine of the present invention may be administered to a subject at risk of being infected by mycobacteria, or to a subject who has been exposed to mycobacteria, or even to a subject known to be infected with mycobacteria. The typical subject is illustratively a living organism capable of mounting an immune response to challenge from the vaccine. Non-limiting examples of a subject include a human, any lower primate, cow, camel, dog, cat, rabbit, rat, mouse, guinea pig, pig, hamster, horse, donkey, cattle, opossum, badger, goat, sheep, or other mammals or non-mammals.

The vaccine of the present invention is suitable for the prophylaxis and/or treatment of a disease or medical condition affected by antigen and/or immunogen expression of the *Mycobacterium*, more preferably the prophylaxis and/or treatment of mycobacterial infections, preferably an infection of *M. ap, M. avium, M. tuberculosis, M. bovis*, or mixtures thereof. According to most specific embodiments, the vaccine is a vaccine against Johne's disease caused by mycobacterial infection.

The vaccine of the present invention may be administered in any conventional dosage form in any conventional manner. In some embodiments, routes of administration include, but are not limited to, intravenously, intramuscularly, subcutaneously, intranasally, intrasynovially, by infusion, sublingually, transdermal, orally, topically, or by inhalation. The preferred modes of administration are subcutaneous, intravenous and intranasal.

In some embodiments, the *Mycobacterium* mutant of the vaccine may be administered alone or in combination with adjuvants that enhance stability and/or immunogenicity of the mycobacteria, facilitate administration of pharmaceutical compositions containing them, provide increased dissolution or dispersion, increase propagative activity, provide adjunct therapy, and the like, including other active ingredients.

In some embodiments, the pharmaceutical dosage forms of the vaccine according to the present invention may include pharmaceutically acceptable carriers and/or adjuvants known to those of ordinary skill in the art. These carriers and adjuvants include, for example, ion exchangers, alumina, aluminium stearate, lecithin, serum proteins, buffer substances, water, salts, electrolytes, cellulose-based substances, gelatine, water, petrolatum, animal or vegetable oil, mineral or synthetic oil, saline, dextrose or other saccharide and glycol compounds such as ethylene glycol, propylene glycol or polyethylene glycol, antioxidants, lactate, etc. Preferred dosage forms include tablets, capsules, solutions, suspensions, emulsions, reconstitutable powders and transdermal patches. Methods for preparing dosage forms are well known in the art.

In other embodiments, the dosage regimen of the vaccine may also be determined by the skilled person using his expertise (e.g. single administration, repeated administration (twice or more at regular or irregular intervals), etc. This will typically also depend on the disease to be treated and the subject receiving the treatment. In a typical animal vaccination, a dose of $10^5$-$10^{10}$ cfu/animal is given via parental or oral routes of vaccination. In one embodiment, the dose is in the range of $10^7$-$10^{10}$ cfu/animal. In another embodiment, the dose is in the range of $10^5$-$10^9$ cfu/animal.

Differentiate Infected from Vaccinated Animals (DIVA)

In its fourth aspect, the present invention provides a method of in vitro differentiating between subjects that have been infected with *Mycobacterium* and subjects that have not been infected with *Mycobacterium* or have been vaccinated with a *Mycobacterium* vaccine. In one embodiment, the method comprises the steps of (a) identifying a gene sequence that is specific to a *Mycobacterium* mutant and is not found in the wild-type *Mycobacterium* strain; and (b) detecting the presence or the quantity of the sequence in the subject. In other embodiments, the method comprises the steps of (a) identifying a gene sequence that is specific to a wild-type *Mycobacterium* strain and is not found in the *Mycobacterium* mutant; and (b) detecting the presence or the quantity of the sequence in the subject. The *Mycobacterium* mutant for the embodiments is any one *Mycobacterium* mutant described herein. These sequences are detectable by use of a complimentary probe or primer.

The gene or the polynucleotides of the invention may contain less than an entire microbial genome and can be single- or double-stranded nucleic acids. A polynucleotide can be RNA, DNA, cDNA, genomic DNA, chemically synthesized RNA or DNA or combinations thereof. The polynucleotides can be purified free of other components, such as proteins, lipids and other polynucleotides. For example, the polynucleotide can be 50%, 75%, 90%, 95%, 96%, 97%, 98%, 99%, or 100% purified. The purified polynucleotides can comprise additional heterologous nucleotides (that is, nucleotides that are not from *Mycobacterium*). The purified polynucleotides of the invention can also comprise other nucleotide sequences, such as sequences coding for linkers, primer, signal sequences, TMR stop transfer sequences, transmembrane domains, or ligands.

The gene or the polynucleotides of the invention can be isolated. An isolated polynucleotide is a naturally occurring polynucleotide that is not immediately contiguous with one or both of the 5' and 3' flanking genomic sequences with which it is naturally associated. An isolated polynucleotide can be, for example, a recombinant DNA molecule of any length, provided that the nucleic acid sequences naturally found immediately flanking the recombinant DNA molecule in a naturally-occurring genome is removed or absent. Isolated polynucleotides also include non-naturally occurring nucleic acid molecules.

The gene or the polynucleotides of the invention can also comprise fragments that encode immunogenic polypeptides. Polynucleotides of the invention can encode full-length polypeptides, polypeptide fragments, and variant or fusion polypeptides. Polynucleotides of the invention can comprise coding sequences for naturally occurring polypeptides or can encode altered sequences that do not occur in nature. If desired, polynucleotides can be cloned into an expression vector comprising expression control elements, including for example, origins of replication, promoters, enhancers, or other regulatory elements that drive expression of the polynucleotides of the invention in host cells.

The gene or the polynucleotides of the invention can be detected by, for example, a probe or primer, for example, a PCR primer, or can be the basis for designing a complimentary probe or primer, to detect the presence and/or quantity of *Mycobacterium* in a subject, such as a biological sample. Probes are molecules capable of interacting with a target nucleic acid, typically in a sequence specific manner, for example, through hybridization. Primers are a subset of probes that can support an specific enzymatic manipulation and that can hybridize with a target nucleic acid such that the enzymatic manipulation occurs. A primer can be made from any combination of nucleotides or nucleotide derivatives or analogs available in the art that do not interfere with the enzymatic manipulation. "Specific" means that a gene sequence recognizes or matches another gene of the invention with greater affinity than to other non-specific molecules. Preferably, "specifically binds" or "specific to" also means a gene sequence recognizes and matches a gene sequence comprised in a wild-type *Mycobacterium* or a *Mycobacterium* mutant described herein, with greater affinity than to other non-specific molecules. More preferably, the probe or the primer is complimentary to a *Mycobacterium* mutant with at least one mutation in the gene of sigH (SEQ ID NO:1), sigL (SEQ ID NO:2), sigE (SEQ ID NO:3), ECF-1 (SEQ ID NO:4), sigB (SEQ ID NO:5) and mixtures thereof.

The hybridization of nucleic acids is well understood in the art. Typically a primer can be made from any combination of nucleotides or nucleotide derivatives or analogs available in the art. The ability of such primers to specifically hybridize to *Mycobacterium* polynucleotide sequences will enable them to be of use in detecting the presence of complementary sequences in a given subject. The primers of the invention can hybridize to complementary sequences in a subject such as a biological sample, including, without limitation, saliva, sputum, blood, plasma, serum, urine, feces, cerebrospinal fluid, amniotic fluid, wound exudate, or tissue of the subject. Polynucleotides from the sample can be, for example, subjected to gel electrophoresis or other size separation techniques or can be immobilized without size separation.

The probes or the primers can also be labeled for the detection. Suitable labels, and methods for labeling primers are known in the art. For example, the label includes, without limitation, radioactive labels, biotin labels, fluorescent labels, chemiluminescent labels, bioluminescent labels, metal chelator labels and enzyme labels. The polynucleotides from the sample are contacted with the probes or primers under hybridization conditions of suitable stringencies. Preferably, the primer is fluorescent labeled. Also, the detection of the presence or quality of the gene sequence of interest can be accomplished by any method known in the art. For instance, the detection can be made by a DNA amplification reaction. In some embodiments, "amplification" of DNA denotes the use of polymerase chain reaction (PCR) to increase the concentration of a particular DNA sequence within a mixtures of DNA sequences.

Preferably, the amplification of DNA is done by the loop-mediated isothermal amplification (LAMP). LAMP was developed by Notomi, et al. (72), incorporated by reference herein in its entirety. Similar to PCR, LAMP utilizes a polymerization-based reaction to amplify DNA from examined samples, but the enzyme for LAMP, Bst DNA polymerase large fragment, possesses a DNA strand displacement activity. This makes the DNA extension step possible without having to fully denature DNA templates. Moreover, the primers are designed in a way that a hairpin loop structure is formed in the first cycle of amplification, and the following products are further amplified in an auto-cycling manner. Therefore, in about an hour, the repeated reactions can amplify by ~$10^9$ copies of DNA molecules and can be done at a constant temperature in a single heat block, instead of at various cycles of temperature in a relatively expensive thermal cycler.

The detection of LAMP can be made by vary technologies known in the art. Preferably, the detection of LAMP can occur without gel electrophoresis through the addition of fluorophore (73,74). This detection method could readily be used in the field to detect positive samples. As a result, a complete diagnosis can be done and visualized in about one hour (72). Quantification and multiplexing techniques have also been developed which could help determine the bacterial load of a sample (73,74). In addition, variants of Bst polymerase and primer additions have increased Bst polymerase stability, decreased amplification time, and provided the polymerase with the ability to reverse transcribe and amplify RNA targets (73,74). Specifically, the increase in stability could help transfer the diagnostic process to the field.

Accordingly, the detection of the presence of the gene or the specific binding between the gene in *Mycobacterium* mutant and a gene that is not a component of a subject's immune response to a particular vaccine may indicate a natural or experimental *Mycobacterium* infection. For example, the absence of such binding or presence may indicate the absence of *Mycobacterium* infection. Or, a second, separate gene, such as a mutated *Mycobacterium* gene that specific to a component of a subject's immune response to a particular *Mycobacterium* vaccine, may be used to detect a corresponding antibodies produced in response to vaccination. Thus, if an antibody specific to a gene in *Mycobacterium* vaccine is detected, then the subject has been vaccinated and/or infected. The detection of neither genes indicates no infection and no vaccination. As such, various combinations can lead to a determination of the vaccination and/or infection status of the subject.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, useful methods and materials are described below. The materials, methods, and examples are illustrative only and not intended to be limiting. Other features and advantages of the invention will be apparent from the detailed description and from the claims.

EXAMPLES

The following examples set forth preferred markers and methods in accordance with the invention. It is to be understood, however, that these examples are provided by way of illustration and nothing therein should be taken as a limitation upon the overall scope of the invention.

Example 1

The disclosure of Example 1 has been published in *Infection and Immnunity*, June 2013, 81(6): 2242-2257, entitled "Key Role for the Alternative Sigma Factor, SigH, in the Intracellular Life of *Mycobacterium avium* subsp. *paratuberculosis* during Macrophage Stress," which is incorporated herein by reference in its entirety.

Bacteria.

*Escherichia coli* DH5α and HB101 were used as host cells for cloning purposes in all experiments presented here. *M. avium* subsp. *paratuberculosis* K10 and *Mycobacterium smegmatis* mc²155 strains were grown in Middlebrook 7H9 broth and on Middlebrook 7H10 plates as previously described (1).

Construction of the ΔsigH Mutant.

A specialized transduction protocol was adopted with a few modifications to delete the sigH/MAP3324c gene using the *M. avium* subsp. *paratuberculosis* strain (12). Briefly, two ~900-bp PCR fragments flanking each end of the sigH coding region were amplified and cloned into the pYUB854 shuttle vector. The resulting pYUB854::sigH allelic-exchange substrate (AES) was then digested with PacI and ligated to the PacI-digested concatemers of a temperature-sensitive phasmid, phAE87. The ligation mixture was then packaged into phage particles with an in vitro lambda-packaging system (GIGAPackIII; Stratagene, La Jolla, Calif.). Mid-log-phase *Escherichia coli* culture was transduced with the packaged phage particles, resulting in hygromycin-resistant colonies. From the mixture of these colonies, shuttle plasmid DNA was extracted and then electroporated into *M. smegmatis* competent cells. Lysate of plaques formed at 30° C. from the transformants was collected, propagated, and titrated in *M. smegmatis* to produce a high-titer recombinant phage stock. A mid-log-phase culture of *M. avium* subsp. *paratuberculosis* was transduced with the phage stock at nonpermissive temperature (37° C.) with a multiplicity of infection of 10. Individual hygromycin-resistant colonies were picked and grown in broth medium following gDNA isolation. The genotype of sigH-deletion mutants was confirmed with PCR and sequence analysis as outlined before (12).

Stress Treatments of *M. avium* Subsp. *paratuberculosis*.

Wild-type and the ΔsigH mutant of *M. avium* subsp. *paratuberculosis* were grown to late-log phase (optical density at 600 nm [$OD_{600}$]=1.0), and 200 ul was spread on 7H10 agar plates (Difco, Sparks, Md.) supplemented with 0.5% glycerol, 2 ug/ml mycobactin J, and 10% ADC (2% glucose, 5% bovine serum albumin [BSA] fraction V, and 0.85% NaCl). For disc diffusion assay (DDA), 20 ul of diamide solution (0.5 M, 1 M, or 1.5 M) and $H_2O_2$ solution (50 mM, 100 mM, or 0.5 M) was impregnated onto each 6-mm disc (Whatman, Piscataway, N.J.), and discs were placed on each of the spread plates. As a positive control, ethambutol discs (5 ug/disc, Sensi-Disc; BD Diagnostics) were used. Plates were incubated at 37° C. until a thick confluent lawn developed. The sustained effect of stressors (diamide and heat shock) on the viability of the wild type and ΔsigH mutant was monitored by determining their CFU counts. Aliquots of *M. avium* subsp. *paratuberculosis* cultures 1, 3, and 7 days following continuous exposure to 10 mM diamide or a 45° C. water bath were serially diluted and plated. In another experiment, *M. avium* subsp. *paratuberculosis* cultures from midlog phase were exposed to 10 mM diamide for 3 h. The cultures were centrifuged (3,000×g, 4° C., 10 min), and pellets were immediately stored at −80° C. until RNA extraction.

Mouse Infections.

For the animal infections with *M. avium* subsp. *paratuberculosis* strains, female BALB/c mice (Harlan Laboratories, Indianapolis, Ind.) were purchased at 4 weeks of age and housed in a pathogen free environment according to the protocol approved by the Institutional Animal Care and Use Committee, University of Wisconsin-Madison. Two groups of mice (n=15 per group) were challenged intraperitoneally with the wild-type and ΔsigH mutant strains of *M. avium* subsp. *paratuberculosis*. Actual infection inoculum sizes (~2×10$^8$ CFU per mouse) of these two strains were similar, as determined by plate count on the day of infection. Mouse groups (n=5) were sacrificed at 3, 6, and 12 weeks postinfection (wpi), and samples from livers, intestines, and spleens were collected for bacterial CFU enumeration and histopathological examinations as described before (17). Portions of livers, spleens, and intestines were fixed in 10% neutral buffered formalin before being sectioned and stained with hematoxylin and eosin (H&E) and Ziehl-Neelsen stain. Student's t test and Mann-Whitney test were used to statistically evaluate differences in CFU counts among mouse groups infected with the wildtype and ΔsigH mutant strains of *M. avium* subsp. *paratuberculosis*.

Bovine Blood Monocyte Isolation and Infection.

Blood was collected from a Johne's disease-free herd that we maintained at the University of Wisconsin-Madison. Three cows (36-month-old Holstein, designated animals 5695, 5970, and 6117) were bled by jugular venipuncture using blood collection bags (TERUFLEX, Somerset, N.J.) containing citrate phosphate dextrose adenine as an anticoagulant. Blood was transferred to 50-ml polypropylene tubes and centrifuged at 1,400×g for 20 min at 25° C. Buffy coat containing white blood cells was isolated and mixed with phosphate-buffered saline (PBS) ($Ca^{2+}$- and $Mg^{2+}$-free) to a final volume of 30 ml. The cell suspension was layered onto 58% isotonic PERCOLL (medium for density gradient centrifugation) (Sigma) at a 1:1 ratio and centrifuged at 2,000×g for 30 min at 25° C. Peripheral blood mononuclear cells (PBMC) were collected from the PERCOLL-PBS interface and washed three times with PBS to remove residual PERCOLL. To isolate bovine monocyte-derived macrophages (MDMs), PBMC were resuspended in RPMI 1640 (Sigma-Aldrich, St. Louis, Mo.) with 20% autologous serum and transferred to TEFLON nonstick coating jars followed by incubation for 4 days at 37° C. and 5% CO2. MDM cells were harvested, washed, and seeded with 2×10$^6$ cells/well in 24-well plates with 5% autologous serum. Immediately before MDM cell infection, *M. avium* subsp. *paratuberculosis* cultures grown to mid-log phase ($OD_{600}$ of 0.4 to 0.6) were pelleted and resuspended in an appropriate volume of cell culture medium to achieve a 50:1 multiplicity of infection (MOI). The cells were incubated at 37° C. with 5% CO2 for 3 h, and, subsequently, the monolayers were washed two times with warm PBS to remove extracellular bacteria, and RPMI 1640 medium containing 5% autologous serum was added. The plates were incubated at 37° C. for up to 8 days, and the culture medium was replaced with fresh medium at 4 days after infection. In another set of experiments, MDM cells were pretreated overnight (18 h) with 0.01 ug/ml recombinant bovine IFN-γ (Kingfisher Biotech, St. Paul, Minn.) before infection with *M. avium* subsp. *paratuberculosis* strains. This concentration of IFN-γ was adequate to activate bovine monocytes (23). Bovine MDM cells were lysed at 1, 4, and 8 days postinfection for CFU plating with serial dilutions. Student's t test was used for statistical analysis, where P values of 0.05 were considered to be significant to evaluate differences in CFU counts.

J744A.1 Cell Culture Infection.

The mouse macrophage cells (J774A.1) were maintained in RPMI 1640 (Sigma-Aldrich, St. Louis, Mo.) supplemented with 5 to 10% heat-inactivated fetal bovine serum (FBS) (Sigma-Aldrich) in 75-cm$^2$ filter-cap tissue culture flasks (Techno Plastic Products, Trasadingen, Switzerland) in a water jacketed incubator (Thermo Scientific, Waltham, Mass.) at 37° C. with 5% $CO_2$. When confluent, cells were detached with a cell scraper and resuspended, and 10% of the cell suspension was replenished with fresh culture medium every 3 to 4 days.

Macrophages were seeded at 1.5×10$^7$ cells per 15-mm cell culture dish (Techno Plastic Products) in 15 ml of culture medium as described above, 30 to 36 h prior to infection, and were incubated at 37° C. with 5% $CO_2$. At least 5 dishes were seeded for each time point. For IFN-γ activation experiments, old culture medium was discarded and 15 ml of fresh medium with 100 U/ml recombinant murine IFN-γ (Pepro Tech, Rocky Hill, N.J.) was added to each dish, 16 to 20 h prior to infection. An approximate 109 CFU bacterial suspension from mid-log phase was mixed with 12 ml of cell culture medium (RPMI 1640-10% FBS, mycobactin J-free) and added to each decanted dish (MOI=50). The cells were incubated at 37° C. with 5% CO2 for 2 or 24 h before intracellular bacteria isolation. For the 24-h-time-point experiments, extracellular bacteria were washed away at 2 h postinfection with 15 ml of warm PBS at least five times or until no visible bacterial particles were observed under an inverted microscope at ×400 magnification. The washed cells were replenished with 15 ml of fresh cell culture medium and incubated until 24 h postinfection. Each condition was replicated at least twice until the quality of extracted RNA passed the criteria described below.

Immunofluorescent Staining for LAMP-1 Expression.

Culture cells grown on a circular coverslip were fixed in 2.5% paraformaldehyde for 10 min and permeated with cold methanol-acetone (1:1) at −20° C. for 5 min. A few drops of TB AuramineM (BD Diagnostics, Franklin Lakes, N.J.) were added and incubated at room temperature for 10 min to stain mycobacteria. The coverslip was washed with 95% EtOH three times and rinsed with PBS containing 0.2% saponin and 2% goat serum. Rat monoclonal antibody 1D4B against mouse LAMP-1 purchased from the Developmental Studies Hybridoma Bank at the University of Iowa was diluted to 20 ug/ml in PBS-saponin-goat serum and incubated with the fixed cells at room temperature for 1 h. The cells were washed with PBS-saponin-goat serum three times, each for 10 min. Goat antibody conjugated with ALEXA FLUOR 633 fluorophore dye against rat IgG (Invitrogen, Carlsbad, Calif.) was diluted to 10 ug/ml in PBS-saponin-goat serum and incubated with the cells for 1 h in the dark at room temperature. The cells were then washed in the same way as described in the last step. Finally, the coverslip was mounted on a microscope slide in Vectashield mounting medium (Vector Laboratories, Burlingame, Calif.) and observed with a Nikon Cl confocal microscope system.

Phagosome pH Measurements.

Phagosome pH measurement was slightly modified from previous studies (26, 27) based on ratiometric measurements. J774A.1 cells were seeded at $2 \times 10^5$ cells per well on a 24-well cell culture plate (Techno Plastic Products) in 0.5 ml of culture medium with or without 100 U/ml murine IFN-γ. A poly-L-lysine (Electron Microscopy Sciences, Hatfield, Pa.)-coated 12-mm circular coverslip was placed in each well before seeding. After overnight incubation, culture medium was replaced with 0.3 ml of prewarmed fresh medium with 5 uM LYSOSENSOR radiometric probe Yellow/Blue DND-160 (Invitrogen), and the cells were incubated for 5 min at 37° C. To generate an in situ pH gradient standard curve, each coverslip was then incubated with morpholineethanesulfonic acid (IVIES) buffer (25 mM MES, 5 mM NaCl, 115 mM KCl, and 1.2 mM MgSO4) of known pH (from 3.5 to 7.0 at a 0.5 interval), in the presence of 10 uM nigericin and 10 uM monensin, for 2 min. The coverslip was immediately mounted on a glass slide and observed under an OLYMPUS BX51 microscope with a reflected fluorescence system. Sixteen-bit grayscale images of two separate channels (excitation of 365/10 nm, emission of 460/50 nm, dichroic of 400 nm; excitation of 365/10 nm, emission of 540/20 nm, dichroic of 400 nm; Chroma, Bellows Falls, Vt.) from each field were taken.

The processing time from sample mounting to image acquisition was controlled so it took no longer than 10 min for each coverslip. Image processing was done with ImageJ 1.44 k (28). For each pH standard, at least 20 individual regions of interest (ROIs) were randomly chosen, and mean intensities of each ROI from both channels were recorded. Ratios of intensities of green (540 nm) to blue (460 nm) from the same pH standard were then averaged, excluding values of = or >2 standard deviations (SD) from the mean. A standard curve of ratios was plotted against pH by applying a Boltzmann equation, $y=A2+(A1-A2)/\{1+\exp[(x-x0)/dx]\}$, where A1 and A2 represent the limits of the fluorescent ratio at infinitely low and high pHs, respectively, x0 is the pH midpoint at $(A1+A2)/2$, x is the observed pH, and dx is the slope of the curve. When needed, cells were infected with *M. avium* subsp. *paratuberculosis* as described above, except the bacteria were prestained with 5 uM VYBRANT dye DiD cell-labeling solutions (Invitrogen) for 10 min (29). Intracellular bacteria could be observed with a third filter set (excitation of 535/50 nm, emission of 675/20 nm, dichroic of 565 nm). ROIs were chosen where the bacteria were colocalized with LYSOSENSOR radiometric probe-stained phagosomes. The average 540/460 ratio of ROIs was plugged into the equation to calculate phagosome pH.

Intracellular Bacterial Isolation and RNA Extraction.

Intracellular bacteria were isolated by a protocol described before (30) with modifications. At 2 or 24 h post infection, infected cells were washed with 15 ml ice-cold PBS at least five times or until no visible bacterial particles were observed under an inverted microscope. The washed cells on each dish were then lysed with 10 ml cell lysis buffer (4 M guanidine thiocyanate, 0.5% sodium N-lauryl sarcosine, 25 mM sodium citrate, 0.5% TWEEN 80 (polyoxyethylene (20) sorbitan monooleate), and 0.1 M β-mercaptoethanol) and collected with a rubber cell scraper. To reduce viscosity and help dissolve cell debris, cell lysates from all dishes were pooled and passed through a 23-gauge needle five times. The lysate was then split into four 14-ml polypropylene centrifuge tubes (Falcon 352059; BD Biosciences, San Jose, Calif.) and centrifuged at 3,200×g and 4° C. for 25 min. Each pellet was washed in 1 ml of TRIZOL regent (monophasic solution of phenol and guanidine isothiocyanate) (Invitrogen) twice and subjected to RNA extraction. Total RNA was extracted by a protocol described before (12, 31). Briefly, bacterial pellets were resuspended in 2 ml of TRIZOL reagent (monophasic solution of phenol and guanidine isothiocyanate) and split into two 2-ml screwcap tubes, each with 3.0 g of 0.1-mm zirconia/silica beads (BioSpect Products, Bartlesville, Okla.) and disrupted in a Mini-BeadBeater-8 (BioSpect Products) at top speed for three pulses of 60 s with 30-s intervals on ice. Following a 5-min incubation at room temperature, the supernatant was transferred to RNase-free tubes and centrifuged at 12,000×g for 15 min. RNA was then isolated according to the manufacturer's instruction. To remove genomic DNA contamination, RNA samples were treated with 10 U of Turbo DNase (Ambion, Austin, Tex.) at 37° C. for 30 min. An IS900 241-bp PCR was performed to confirm that no genomic DNA was detectable in the RNA samples (1). DNase treatments were repeated if needed. Quality of the extracted RNA was examined with a NANODROP 1000 spectrophotometer (Thermo Scientific). The ratios of $A_{260}/A_{280}$ and $A_{260}/A_{230}$ must be higher than 1.8 and 1.5, respectively, before proceeding to cDNA synthesis for transcriptome studies.

Transcriptome Studies.

The NimbleGen (NimbleGen System Inc., Madison, Wis.) *M. avium* subsp. *paratuberculosis* microarray was designed from the 4,350 open reading frame sequences in the genome of *M. avium* subsp. *paratuberculosis* (32). The whole genome was represented three times on each chip. In addition, each gene was represented by 20 probes of 60-mer oligonucleotides. As a result, each gene was represented by a total of 60 probes. Double-stranded cDNA synthesis from isolated RNA samples, microarray hybridization, and data analysis were performed as previously described (12, 33). Significantly expressed genes were selected by ±2-fold of change and P values of <0.05 by Student's t test. The intensities were also exported to Gene Spring GX (Agilent Technologies, Santa Clara Calif.) for principal component analysis (PCA) on treatment conditions, which is a method to reduce dimensionality in multicondition microarray experiments and to find relevant patterns across conditions (34). Two biological replicates were included for each condition.

For RNA-seq studies, purified RNA samples were used for depletion of rRNA sequences to enrich mRNA using the MICROBEXPRESS bacterial mRNA enrichment kit (Ambion, Austin, Tex.). Approximately, 10 ug of total RNA for each sample was processed according to the manufacturer's instructions. For cDNA library preparation and sequencing, samples containing at least 1 ug of enriched mRNA were sent to the DNA Sequencing Facility at the University of Wisconsin-Madison Biotechnology Center. An Illumina HiSeq 2000 platform using one flow cell lane with 100-cycle paired-end chemistry (Illumina, San Diego, Calif.) was used to sequence the cDNA library clusters. Raw RNA-seq data files in FASTQ format were assembled against the M. avium subsp. paratuberculosis (35) using the CLC Genomics Workbench 4.8 (CLC bio, Aarhus, Denmark). Gene expression for each of the different sample conditions was calculated using "reads per kilobase million" (RPKM) expression values (36). The following formula was used to determine the RPKM values: RPKM=number of reads/(kilobase length of gene x millions of mapped reads).

This RPKM metric enables comparisons between data sets with a varying number of total reads. All reads mapping to annotated noncoding RNA (ncRNA) were removed from the data sets before determining RPKM values. Data sets were quantile normalized, and Kal's Z-test (37) was used for the comparative gene expression analysis. Genes were considered significantly, differentially expressed if they showed a ±2.5-fold change with FDR P values of <0.05.

Quantitative Real-Time PCR.

Quantitative real-time PCR (qRT-PCR) was previously described (12, 38) for confirmation of transcript levels. A SYBR green-based reagent with ROX (Bio-Rad, Hercules, Calif.) was used with 50 ng of double-stranded cDNA in each reaction. Double-stranded cDNA synthesis is described in the microarray sample preparation session. No gDNA was detected from the RNA samples for cDNA synthesis. qRT-PCRs were performed with a 7300 real-time PCR system (Applied Biosystems, Foster City, Calif.). The threshold cycle (CT) of each gene was normalized to the CT of the 16S rRNA gene from the same cDNA sample. The expression fold changes were calculated by comparing the normalized CT of treated samples to the control sample as detailed before (39, 40).

Microarray Data Accession Number.

Data sets discussed in this report were deposited in NCBI's Gene Expression Omnibus (41) and are accessible through GEO Series accession number GSE43645.

Results

Characterization of M. avium Subsp. paratuberculosis-Containing Phagosomes.

In our previous study, we defined the stressome of M. avium subsp. paratuberculosis under various in vitro conditions that mimicked the hostile host microenvironments, including low pH and oxidative stress (12). In the present study, we further examined the bacterial responses in the early stage of cell infection using a murine macrophage infection model. Both naive and IFN-γ-activated cells were used in our study. We monitored the expression of inducible nitric oxide synthase (iNOS), a marker for macrophage activation, with quantitative real-time PCR following IFN-γ treatment of J774A.1 cells. The transcription activity of iNOS in IFN-γ-treated cells was over 1,000 times higher than naive cells (data not shown). The temporal profile of iNOS expression indicated that naive macrophages were activated by 2 h postinfection and throughout the course of infection, with comparable mRNA levels regardless of the viability of M. avium subsp. paratuberculosis bacilli. Activated macrophages had a similar profile, but the iNOS expression levels were between 1.6 to 2.6 times greater than those of infected naive macrophages at each time point.

Additionally, we measured the phagosomal pH in both naive and activated macrophages using a dual-emission dye LYSOSENSOR radiometric probe DN-160 that emits fluorescent signals in a pH-dependent manner. Before infection, naive and activated macrophages had similar lysosomal pH levels ranging from 5.1 to 5.3. At 2 h postinfection, the pH in phagosomes containing heat-killed M. avium subsp. paratuberculosis decreased below 4.0 regardless of cell activation status. However, the pH in phagosomes containing live M. avium subsp. paratuberculosis bacilli decreased just below the preinfection level (i.e., 4.8 to 5.0), suggesting the ability of live bacteria to prevent phagosome acidification. Activated macrophages, but not naive ones, were able to continuously decrease the pH of phagosomes containing live bacilli up to 4 h of postinfection. As the infection progressed (24 h), activated macrophages exhibited a better ability to maintain a lower pH level than naive macrophages.

To examine the role of M. avium subsp. paratuberculosis on phagosome maturation, we examined the percentage of colocalization between intracellular M. avium subsp. paratuberculosis and the lysosome marker LAMP-1. While heat-killed bacteria showed over 85% colocalization with LAMP-1, live M. avium subsp. paratuberculosis significantly reduced the percentage of colocalization with LAMP-1 at 2 h postinfection (67.6%±5.5) in naive macrophages, suggesting live M. avium subsp. paratuberculosis is able to rapidly circumvent the hostile environment and to delay phagosome maturation. The percentage of colocalization did not significantly change in activated macrophages over the course of the experiment (87.92%±5.32 and 83.7%±9.5 at 2 h and 24 h, respectively), suggesting that preactivated host cells have a better ability to control invading intracellular pathogens by means of phagosome maturation. The reduced phagolysosome fusion of naive macrophages was restored to a level (78.4%±6.8) similar to that of the preactivated phagosome (81.6%±8.8) at 24 h postinfection, as also evidenced by the increased iNOS expression level of the naive macrophage infection compared to uninfected cells (data not shown). In general, both phagosomal pH and LAMP-1 colocalization indicated the ability of live, virulent M. avium subsp. paratuberculosis to prevent phagosome acidification and to delay lysosomal fusion by 2 h postinfection.

Transcriptional Profiling of M. avium Subsp. paratuberculosis Isolated from Infected Macrophages.

To profile changes in the levels of M. avium subsp. paratuberculosis transcripts within macrophages, we isolated intracellular bacilli at 2 and 24 h postinfection, with or without IFN-γ activation. Because the bacteria must stay in the cell culture medium (RPMI 1640-10% FBS, mycobactin J-free) before they can infect host macrophages, we compared the transcriptomes of intracellular bacteria to those incubated in vitro in cell culture medium for 2 h. Under all conditions tested, the correlation coefficients (r) between biological replicates ranged between 0.92 and 0.99. To examine the statistical distance between each biological replicate and among treatments, a three-dimensional principal component analysis plot was generated, indicating high correlations between biological replicates. Cluster analysis identified groups of genes active only during macrophage infection. Compared to the RPMI-incubated control sample, expression levels of 136 and 333 M. avium subsp. paratuberculosis genes were significantly changed in naive macrophages at 2 and 24 h postinfection, respectively. On the other hand, in IFN-γ-activated macrophages, the numbers of genes with significantly changed expression levels were 284 and 328, respectively. Among those genes, 47 were common in all of the 4 examined macrophage conditions, representing a core set of genes responsible for interacting with the macrophage microenvironment.

In general, M. avium subsp. paratuberculosis transcriptomes in infected macrophages preactivated with IFN-γ were more similar to those observed under in vitro stressors reported earlier (12). Also, IFN-γ activation of macrophages resulted in significant induction of a group of genes (n=48), mostly those involved in energy production and conversion (e.g., icl, fdxA, sdhABCD, and ndh) or nutrient transport and metabolism (e.g., fad genes, dapA_1, and cysH_2), at 2 h postinfection in IFN-γ-activated macrophages compared to naive macrophages.

At 24 h postinfection, we started to see a significant change in M. avium subsp. paratuberculosis transcriptomes indicative of change of their microenvironment, especially in activated macrophages. For example, the mbt operon (mbtA to mbtE and MAP2172c) involved in iron metabolism was significantly upregulated at 24 h postinfection in IFN-γ-treated macrophages compared to the RPMI-incubated control samples. A similar observation was reported for 120 h postinfection of bovine monocyte-derived macrophages (MDMs) (21). MAP2172c was shown to be repressed in M. avium subsp. paratuberculosis cultures grown in mycobactin J-depleted medium over time, where expression levels of other mbt genes remained constant (42). This paradigm could suggest that an intracellular environment is not iron exochelin-free, or there are other intracellular factors that stimulate alternative iron metabolic pathways, at least in the examined times. On the other hand, a gene involved in iron storage, bfrA (43), was significantly downregulated at the same time point, while the mbt operon was activated, suggesting the lack of access to iron inside the mycobacterial phagosome. Interestingly, the expression of the iron-dependent regulator ideR (43) remained unchanged during the examined time course regardless of macrophage activation status, suggesting a lesser role of ideR in early stages of macrophage infection. Overall, a significant time-dependent shift in M. avium subsp. paratuberculosis transcriptomes was evident from examining M. avium subsp. paratuberculosis collected at 2 and 24 h after macrophage infection.

Microenvironment of M. avium Subsp. paratuberculosis.

One of our goals is to gain more insights into the intracellular environment of M. avium subsp. paratuberculosis using transcriptome analysis. Schnappinger et al. reported that M. tuberculosis upregulates β-oxidation genes by 4 h postinfection in murine bone marrow macrophages, suggesting a transition of carbon source from carbohydrates to fatty acids (44). Similarly, our study indicated activation of M. avium subsp. paratuberculosis orthologues (fadA6_3, fadB_1, fadD9, fadE17, fadE21, fadE3_1, and fadE5) in the β-oxidation pathway starting from as early as 2 h postinfection, suggesting the transition of carbon source utilization is a common bacterial strategy between M. tuberculosis and M. avium subsp. paratuberculosis. The id gene, previously known as aceA, was also among the highly upregulated genes involved in carbon metabolism. The gene product, an isocitrate lyase, bridges the β-oxidation pathway to glyoxylate cycle, an anabolic pathway with a net product of glucose. The contribution of id to M. avium subsp. paratuberculosis survival in macrophages remains to be analyzed.

Once entering host cell compartments, intracellular bacteria encounter host defense mechanisms such as reactive oxygen intermediates (ROIs), reactive nitrogen intermediates (RNIs), digestive enzymes, and, most importantly, lower pH. In addition, the phagosome is also a nutrient-depleted environment. Accordingly, we examined genes that are associated with stress response and intracellular bacterial survival. Several known oxidative stress-induced genes, such as oxyR, trxB, trxC, tpx, ahpC, and ahpD, were significantly upregulated in all intracellular conditions. OxyR is a redox sensor protein that, when oxidized, positively regulates a group of genes, including ahpC, katG, gorA, and furA (45). Among those genes, the ahpCD operon was highly upregulated (6.2- to 11.0-fold) in samples taken from naive or activated macrophages. In addition, TrxB, TrxC, and Tpx, proteins involved in reduction of thio-disulfide and resistance of hydroperoxide processes (46), were upregulated, suggesting active machinery for counteracting oxidative stress within host cells. However, other known oxidative responsive genes, such as katG, gorA, furA, sodA, and sodC, were not activated in these samples, possibly because those genes are indirectly regulated by oxyR or also under the control of other stress-response regulators. Overall, M. avium subsp. paratuberculosis deployed specific gene products to defend against the hostile microenvironment during this early stage of infection.

Figure 1B:
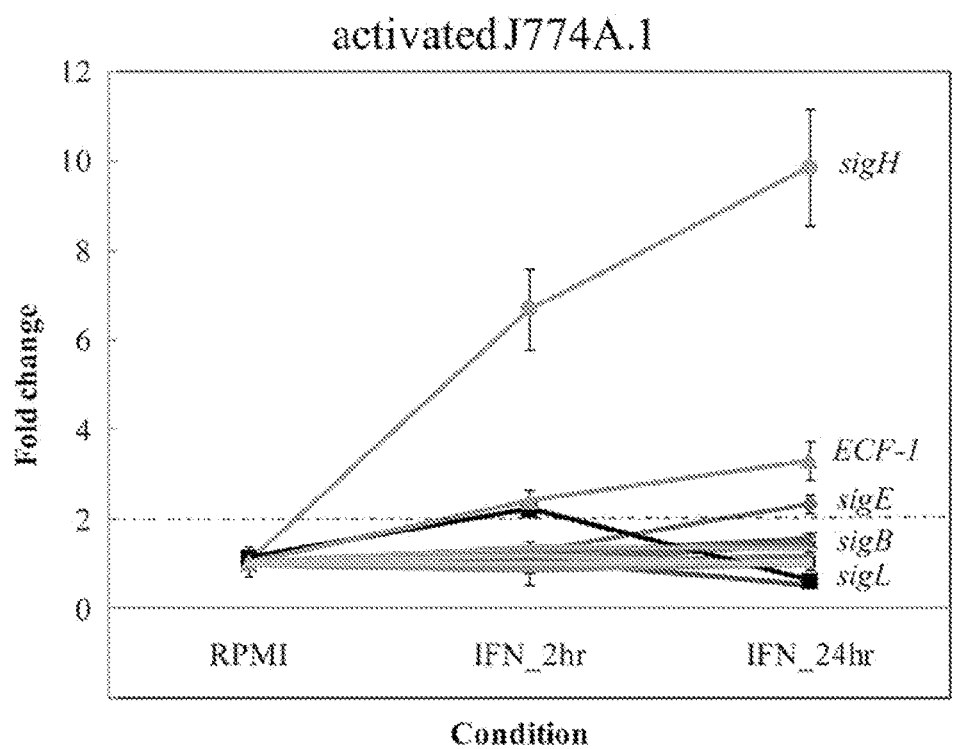
FIG. 1B. Temporal expression of *M. avium* subsp. *paratuberculosis* sigma factors within macrophages using DNA microarrays. A selected list of the *M. avium* subsp. *paratuberculosis* sigma factor genes are shown under activated macrophages. Note that sigH and other ECF-1 (ECF-1 on the chart for clarity) were upregulated immediately after infection, followed by expression of sigE and sigB.

Changes in global gene regulators. Sigma factors play a central role in bacterial gene regulation (47) and pathogenesis as reviewed in M. tuberculosis (48) and other pathogens (49). Nineteen sigma factors were identified in M. avium subsp. paratuberculosis by sequence analysis (24), 13 of which are homologous to M. tuberculosis sigma factors. The sigA gene, though considered a constitutively expressed sigma factor gene in M. tuberculosis (50), was found downregulated to nearly 2-fold at 24 h in activated macrophages. The sigB gene, which is a dispensable sigma factor and partially responsive to some oxidative and heat shock stresses in M. tuberculosis (51), showed a slight increase (~1.6-fold) at 24 h postinfection under both activated and naive states of macrophages. Genes of sigC, sigG, sigJ, sigM, and other extracytoplasmic sigma factors (ECF-2 through ECF-6) remained constantly expressed in all examined conditions. However, as shown in FIG. 1, sigH was the most induced among other sigma factors of M. avium subsp. paratuberculosis, and the activation seems to be augmented by macrophage activation over time. sigH transcripts were upregulated under in vitro heat shock and oxidative stress treatments in M. avium subsp. paratuberculosis (12). Also, sigL was upregulated at the 2-h time point but downregulated by 24 h postinfection, suggesting a potential role for sigL in the very early stage of infection. On the contrary, sigE expression was significantly upregulated after 2 h postinfection and remained high at 24 h postinfection, suggesting a prolonged role during M. avium subsp. paratuberculosis persistence. Overall, a few sigma factors showed a dynamic and active gene regulation transition during the first 24 h postinfection within macrophages. It is possible that other regulators could play a similar role during later times of infection or in different host cells.

Role of sigH in M. avium Subsp. paratuberculosis to Variable Stress Conditions.

The sigH gene in M. tuberculosis has been shown to be upregulated upon heat shock, upon diamide treatment (25), and during survival in human macrophages (52), suggesting its importance in responding to extracellular stimuli and intracellular survival. To test the hypothesis that sigH could play an important role in M. avium subsp. paratuberculosis stress responses, we employed a specialized transduction protocol (53) to generate a sigH isogenic knockout mutant in the *M. avium* subsp. *paratuberculosis* K10 genetic background. Because sigH and its anti-sigma factor (MAP3323c) are likely encoded in an operon (54), the ΔsigH mutant was examined for possible polar effects on the downstream gene, MAP3323c. Using reverse transcriptase PCR, the presence of the MAP3323c transcript was confirmed in the ΔsigH mutant strain.

After construction, the resistance of the ΔsigH mutant was evaluated against various stressors. Analysis of the disc diffusion assay revealed that the ΔsigH mutant does not tolerate thiol-specific oxidation compared to the wild-type strain, as evidenced by the observed halo zones on plates. However, no other differential resistance was observed when a cell wall stressor (sodium dodecyl sulfate) or ethambutol discs were used (data not shown). To measure viability of the ΔsigH mutant after sustained exposure to diamide or heat stress, we cultured both wild-type and the mutant strains for an extended time period in the presence of diamide or a 45° C. water bath. In both stress conditions, there was significant reduction at each time point in the viability of the ΔsigH mutant compared to that of the wild-type strain. At day 7, the viability of the ΔsigH mutant was reduced by almost 2-log orders and more than 1-log order in CFU counts relative to the wild-type strain for diamide and heat stress, respectively. Unfortunately, replicative plasmid complementation of the ΔsigH mutant with a wild-type sigH under the control of the hsp65 promoter did not restore the diamide resistance phenotype (data not shown), most likely due to inefficient complementation in mycobacterial strains (25, 55, 56).

Intracellular Survival of the ΔsigH Mutant in Bovine MDM Cells.

Figures 2A, 2B:
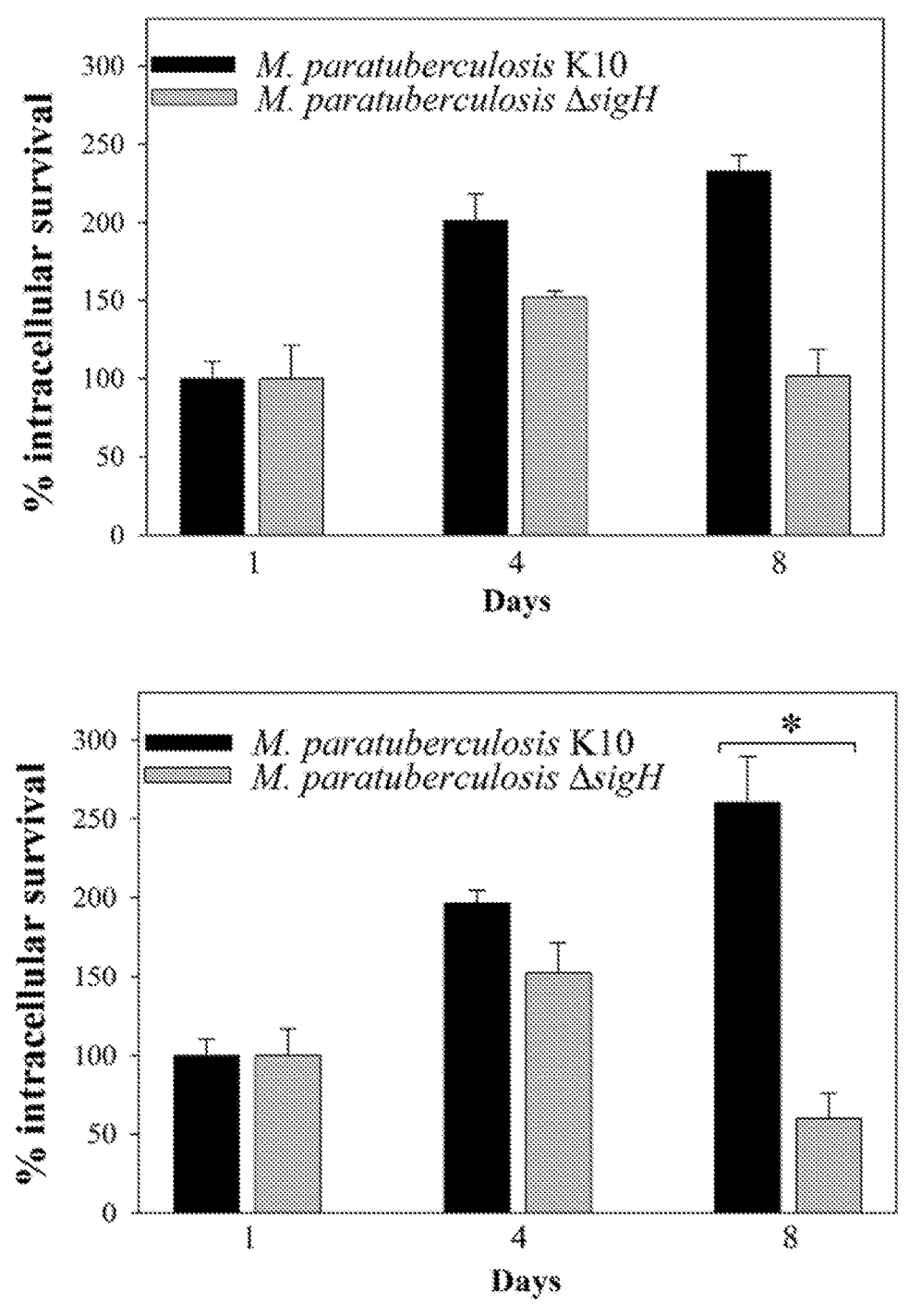

Intracellular growth kinetics of *M. avium* subsp. *paratuberculosis* strains were analyzed using bovine MDM cells. MDM cells were infected with the ΔsigH mutant and its parental strain for a prolonged time up to 8 days after infection. The MDM monolayer in the culture wells was checked at a regular interval for cell confluence under an inverted light microscope. We first determined intracellular viability of both the ΔsigH mutant and wild-type strains within the naive MDM cells. The numbers of wild-type strain of *M. avium* subsp. *paratuberculosis* bacilli increased 2-fold, whereas the growth of the ΔsigH mutant was not supported within naive MDM cells as determined by CFU plating at 8 days after infection (FIG. 2A). Next, we examined whether the ΔsigH mutant would be able to survive inside activated MDM cells pretreated with recombinant IFN-γ. At 8 days post infection, there was more than a 2-fold increase in the number of wild-type *M. avium* subsp. *paratuberculosis* bacilli, whereas in the IFN-γ pretreated MDM cells, viability of the ΔsigH mutant was significantly reduced almost by 50% (FIG. 2B). These observations suggested an important role for sigH in defending *M. avium* subsp. *paratuberculosis* against IFN-γ activation.

Virulence Analysis of the *M. avium* Subsp. *paratuberculosis* ΔsigH Mutant.

Figure 3A:
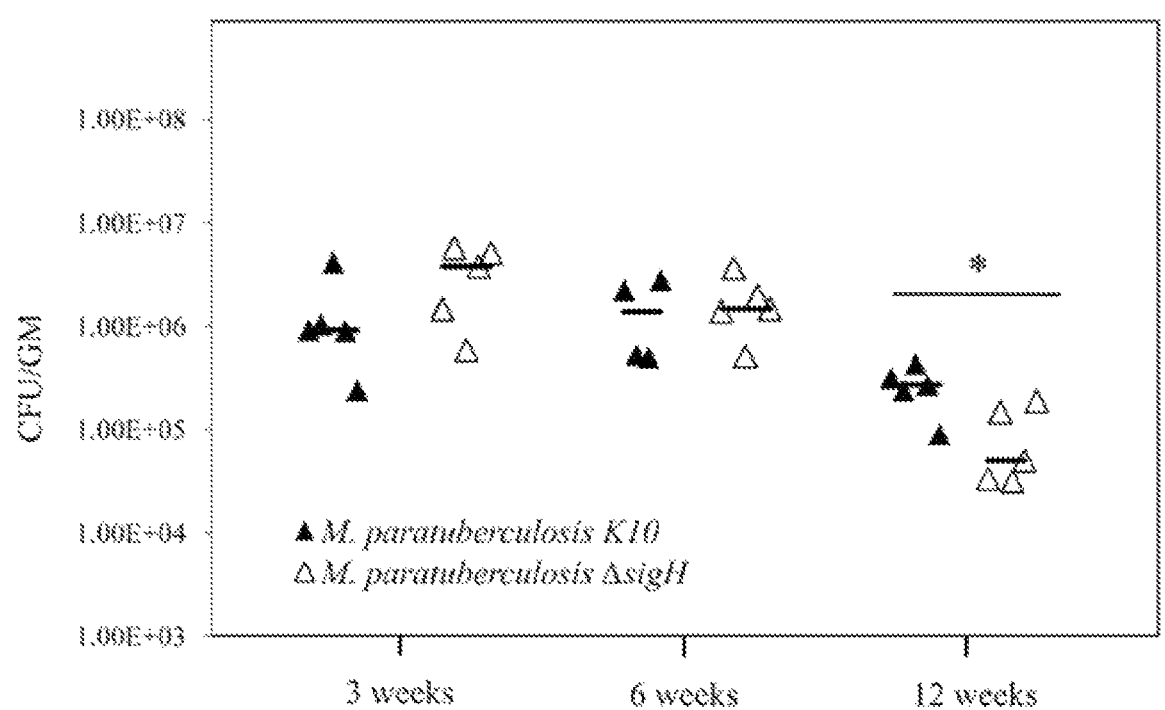
FIG. 3A. Virulence of *M. avium* subsp. *paratuberculosis* K10 and the ΔsigH mutant in mice. Mice groups (n=15) were inoculated with ~2×10$^8$ CFU/mouse of *M. avium* subsp. *paratuberculosis* wild-type strain or the ΔsigH mutant via intraperitoneal injection. Intestines were collected at 3, 6, and 12 wpi (n=5 mice/group/time point) and cultured for bacterial counts. Colony counts for each group are represented by scattered plots accompanied with a median line. Organs with significant difference in bacterial load were denoted with * for P values of <0.05 or ** for P values of <0.01).
Figure 3B:
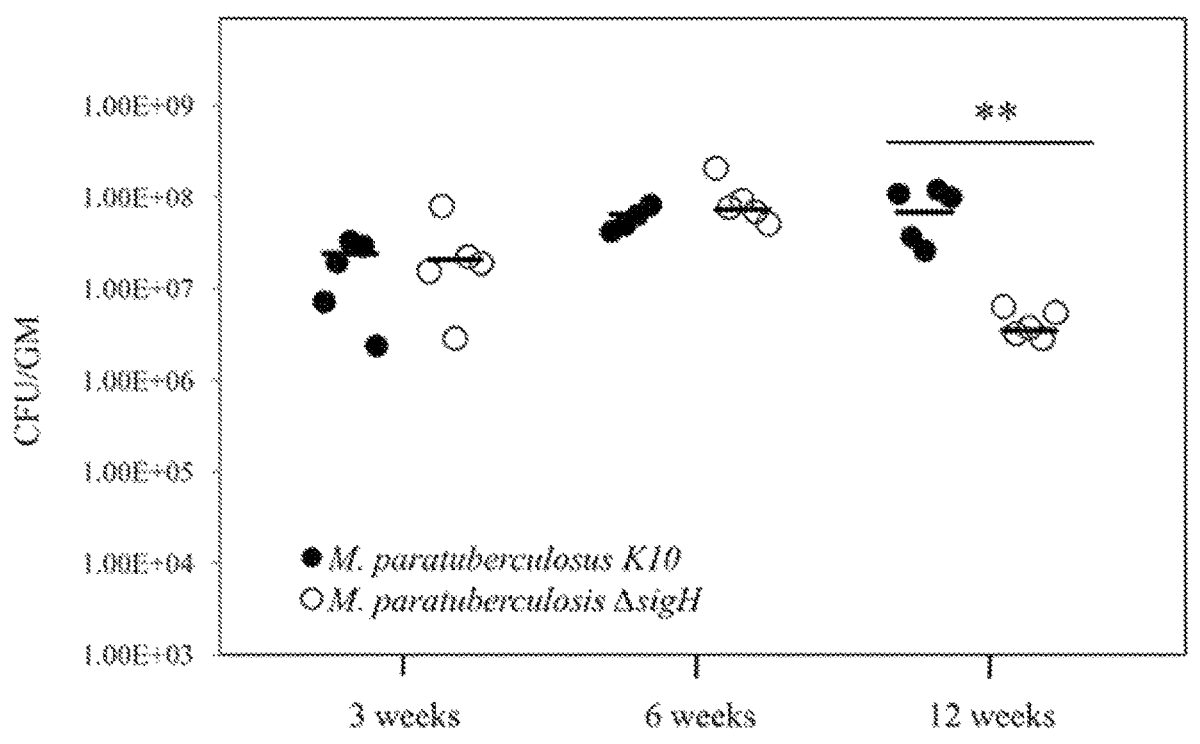

To assess the role of SigH in *M. avium* subsp. *paratuberculosis* virulence, we investigated the persistence of the *M. avium* subsp. *paratuberculosis* ΔsigH mutant using the mouse model of *paratuberculosis*. The initial growth kinetics of the wildtype and ΔsigH mutant strains were similar, with an equal burden of bacteria in both intestine and spleen up to 6 wpi (FIG. 3). However, the colonization levels of the ΔsigH mutant compared to its parental strain were significantly reduced in spleen and intestine at 12 wpi, suggesting a role for sigH in the long-term survival of *M. avium* subsp. *paratuberculosis* in mice. Interestingly, when *M. tuberculosis* ΔsigH was used to challenge mice, no differences in bacterial load were observed in mouse organs compared to that of the wild-type strain (57).

Figures 3C, 3D:
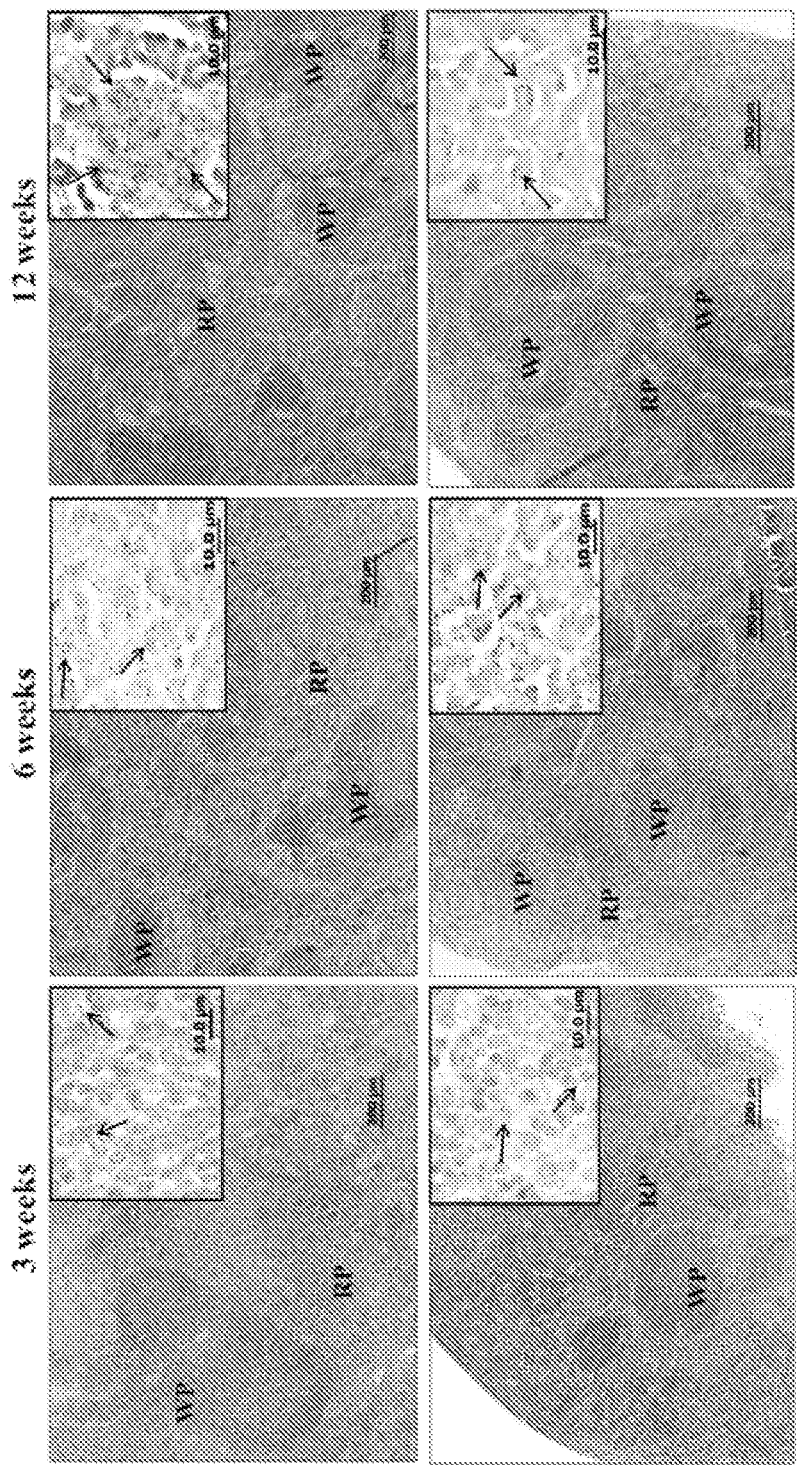
FIG. 3C. Pathology of spleen collected from mice infected with *M. avium* subsp. *paratuberculosis* K10. H&E-stained sections with 100× magnification (scale bar=200 µm) are shown. Inset images (1,000× magnification, scale bar=10 µm) show the *M. avium* subsp. *paratuberculosis* bacilli in purple color (arrows). WP, white pulp; RP, red pulp.
FIG. 3D. Pathology of spleen collected from mice infected with *M. avium* subsp. *paratuberculosis* K10 and its isogenic ΔsigL mutant. H&E-stained sections with 100× magnification (scale bar=200 µm) are shown. Inset images (1,000× magnification, scale bar=10 µm) show the *M. avium* subsp. *paratuberculosis* bacilli in purple color (arrows). WP, white pulp; RP, red pulp.

Evaluation of the hematoxylin and eosin-stained spleen, liver, and intestine organs at 3, 6, and 12 wpi showed moderately similar tissue pathology when infected with the ΔsigH mutant or wildtype *M. avium* subsp. *paratuberculosis*. Granulomatous inflammation was evident in the liver tissues by 12 wpi, with no visual differences in mycobacterial colonization among the mouse groups infected with wild-type or mutant strains. However, mouse spleen tissues infected with the wild-type strain displayed higher follicular atrophy than the spleen tissues infected with the ΔsigH mutant. Consistent with the bacterial colonization data, Ziehl-Neelsen staining showed higher numbers of acid-fast bacilli in the mouse spleen infected with the wild-type strain than the ΔsigH mutant at 12 wpi (FIG. 3C). Taken together, our data indicated that the ΔsigH mutant was attenuated in the murine model of *paratuberculosis* compared to the wild-type *M. avium* subsp. *paratuberculosis* strain.

Transcriptional Regulation of sigH in *M. avium* Subsp. *paratuberculosis*.

Our stress experiments showed that the ΔsigH mutant was hypersensitive to elevated temperature and diamide exposure, each resulting in impaired growth. On the basis of these findings, we hypothesized that sigH may play an important role in directing transcriptional control under unfavorable environmental conditions. To identify gene regulatory networks under the control of sigH, both wild-type *M. avium* subsp. *paratuberculosis* and ΔsigH mutant transcriptomes were profiled before and after diamide exposure using the next-generation RNA sequencing (RNA-seq). When the wild-type strain was compared to the ΔsigH mutant, approximately 15% of the *M. avium* subsp. *paratuberculosis* genes (~307 induced and ~344 repressed) were found to be differentially regulated at 3 h postexposure to diamide stress. This large number of gene perturbation was likely orchestrated by additional sigma factors (e.g., sigB, sigD, sigE) along with various transcriptional regulators that were differentially expressed in examined samples. Genes were grouped into different functional categories, and a large number of genes (e.g., hsp, clpB) belonging to the chaperonin functional category were significantly upregulated. Many induced genes were involved in detoxification and maintaining cellular redox homeostasis (e.g., trxB2, adhE) during oxidative stress as detailed before (46, 58). Many transcriptional factors and two-component systems were found to be upregulated (e.g., sigB, sigE, whiB4, MAPK_0206, mtrA) under the control of SigH. The expression of mycobacterial sigB and sigE was known to be linked with the presence of the sigH gene (59). WhiB-like proteins are redox-responsive DNA binding factors and could play a protective role against oxidative stress (60). In mycobacteria, the role of the MtrB-MtrA two-component system is not entirely understood, but it was found to be essential for bacterial viability, particularly involved in the regulation of cell wall permeability (61, 62).

A number of induced genes in the SigH regulon were related to virulence, and many of them were included in the mce gene family (e.g., mceA1, mceC, mceD). Several mce genes were shown to be upregulated during phagocytosis and oxidative stress exposure (52, 63), indicating that they are active during infection. Other key functional gene categories were associated with central intermediary/sulfate metabolism (e.g., rmlB, rmlC, cysQ_2, cysD), energy metabolism (e.g., rpi, tpi, nuoA), and cell processes/transport (e.g., fdxC_2, MAPK_4062) or were cell envelope related (e.g., mmpL4_1, mmpS3). Our results indicate that many of these genes were induced under intraphagosomal stresses inside macrophages. Genes belonging to functional categories, including lipid metabolism (e.g., fadE14, fadD33_2, MAPK_2213), polyketides (e.g., pks2, papA3_2), and biosynthesis of amino acids (e.g., leuC, metA, trpE2), were among the down regulated genes in *M. avium* subsp. *paratuberculosis* relative to the ΔsigH mutant following diamide stress. We also examined the differential expression profile of *M. avium* subsp. *paratuberculosis* in the absence of sigH during standard physiological growth conditions (mid-log phase). In this case, gene categories belong to lipid metabolism (e.g., fadD29), cell processes (e.g., kdpA, pstS), transcriptional regulation (e.g., MAPK_0788), and electron transport (e.g., fdxC 2). Additionally, we found that a large number of genes belong to the hypothetical functional category (~30%). To verify the transcriptome results, a few upregulated genes were randomly selected, and qRTPCR was employed using the SYBR green method. The transcript levels of these genes analyzed by RNA-seq and qRT-PCR were in good agreement and corroborated with the transcriptome data.

Identification of sigH-Regulated Promoters in *M. avium* Subsp. *paratuberculosis*.

For identification of promoters that were likely to be directly controlled by sigH, we analyzed a list of candidate transcripts with higher expression ratios (wild type/ΔsigH mutant). Since SigH of *M. avium* subsp. *paratuberculosis* is a very close homologue of *M. tuberculosis* SigH (59), we searched for the presence of the consensus sequence of *M. tuberculosis* SigH-dependent nondegenerate promoter motifs GGAA-N18-20-GTT in the 250-bp region upstream of start codons of *M. avium* subsp. *paratuberculosis* genes using the Genolist webserver (genodb.pasteur.fr/cgi-bin/WebObjects/GenoList). A total of 30 genes were found to be directly upregulated by SigH with GGAA and GTT core motifs at the −35 and −10 regions, respectively, in their promoter regions. Many of these targets of SigH in *M. avium* subsp. *paratuberculosis* were also found to be controlled in *Corynebacterium glutamicum* (64), *Streptomyces coelicolor* (65), and *M. tuberculosis* (59), suggesting a conserved regulon directly controlled by SigH across the high-percentage GC Gram-positive actinobacteria.

Discussion

The intracellular pathogen *M. avium* subsp. *paratuberculosis* is known to infect and persist within host macrophages with unclear mechanisms. To examine how *M. avium* subsp. *paratuberculosis* responds to intracellular environments, especially during the early stages of infection, we used a macrophage cell line coupled with DNA microarrays to profile macrophage-induced changes in *M. avium* subsp. *paratuberculosis* transcriptome. A clear advantage of this infection model is the flexibility to control the activation status of the host cells in addition to the availability of reagents and protocols for manipulation. By comparing the results of phagosome pH and phagosome colocalization markers, we found significant differences in intracellular environments of naive versus active macrophages consistent with earlier studies (44, 66). Activated macrophages, at the time of infection, showed much higher iNOS gene expression than naive macrophages. At 2 or 24 h postinfection, they showed higher phagosome colocalization with ingested *M. avium* subsp. *paratuberculosis* particles, which clearly exhibited a better cell defense mechanism than naive macrophages. However, during the course of infection up to 24 h, overall survival of intracellular *M. avium* subsp. *paratuberculosis* did not differ in either naive or activated macrophages. This phenotype could change later during persistent infection which we did not address in this study. Most of the differentially expressed genes between these states are core stress responsive genes involved in energy production, indicating *M. avium* subsp. *paratuberculosis* initiates stress responses to a higher level more rapidly in activated intracellular environments. On the host side, once activated, the host cells maintained their activation status throughout the course of infection. This suggests that virulent *M. avium* subsp. *paratuberculosis* has the ability to prevent phagosome maturation and subsequently circumvent detrimental low pH and oxidative stresses during the very early stages of infection, possibly without interfering with the host early signal transduction pathways responsible for macrophage activation.

When *M. avium* subsp. *paratuberculosis* transcriptomes in macrophages were compared to our previous study of the in vitro stressome (12), there were more common genes with the 24-h than 2-h-postinfection samples, indicating that during the early stage of infection, *M. avium* subsp. *paratuberculosis* is adjusting to more acidic and oxidizing environments. We also observed the metabolic shift of *M. avium* subsp. *paratuberculosis* to utilize fatty acids as the major carbon source, which has already been observed in *M. tuberculosis* (44) and *M. avium* subsp. *paratuberculosis* (21). The shift of metabolic activity at early infection may be a common theme employed by mycobacterial pathogens under nutrient-depleted conditions. By 24 h postinfection, securing iron for *M. avium* subsp. *paratuberculosis* became a significant quest, especially in activated macrophages, as suggested by the activation of the mbt operon. It is well established that the phagosome is an iron-depleted compartment (44) and intracellular pathogens have evolved ways to scavenge iron within mammalian cells. However, iron acquisition mechanisms of *M. avium* subsp. *paratuberculosis* remain unknown given that *M. avium* subsp. *paratuberculosis* possesses a truncated mtbA gene and thus is unable to produce mycobactin (32).

Because of the important role played by global gene regulators in bacterial pathogenesis, we focused our analysis on the expression profile of the 19 sigma factors encoded in the *M. avium* subsp. *paratuberculosis* genome (32). Accordingly, in the experiments reported here, we were able to capture active gene regulation of a set of sigma factors (e.g., sigH, ECF-1) during early macrophage infection with *M. avium* subsp. *paratuberculosis*. Consistent with the *M. tuberculosis* infection studies, we found an immediate upregulation of sigH within macrophages. This trend continued through 24 h postinfection and indicated a crucial role of sigH to regulate stress-responsive genes, especially those activated during exposure to thiol oxidation, as indicated by the disc diffusion assay. Moreover, we have demonstrated that the ΔsigH mutant is very sensitive to sustained exposure to diamide or heat stress compared to the wild-type strain. The sigE gene, another stress-induced sigma factor, did not show higher expression levels until 24 h postinfection in either naive or activated macrophages. This delayed response of sigE as well as modest induction of sigB may indicate an indirect regulation by other immediate stress-responsive genes and support the important role played by sigma factors in mycobacterial pathogenesis (25, 59). The other sigma factor that was upregulated throughout the examined time course was ECF-1. This sigma factor may also play an important role immediately upon infection, which was not reported before.

We have also profiled the regulatory network under the control of sigH by studying the relative abundance of gene transcripts using RNA-seq. We found that a large number of

*M. avium* subsp. *paratuberculosis* genes were directly or indirectly regulated by sigH after exposure to diamide stress. In fact, analysis of the upstream sequence of the upregulated genes revealed a set of genes that could be directly controlled by SigH. Among them, many genes are involved in the functional category of heat shock and protein processing. Heat shock proteins (e.g., Hsp, DnaJ2, ClpB) are found widely on prokaryotic cells and act as molecular chaperones helping to configure proteins correctly upon encountering an unfavorable milieu (67, 68). Such environments, i.e., oxidative stress, could result in nonrepairable protein structures which may necessitate full degradation by the ClpC protease (63). Oxidative stress scavengers induced following diamide stress include TrxB2, TrxC, and AdhE (46, 58). All of these genes likely play important roles in redox homeostasis under thiol oxidation and are found in high levels inside the macrophages (44, 63). Interestingly, the effect of diamide stress in *M. tuberculosis* also resulted in a transcriptional profile similar to that of *M. avium* subsp. *paratuberculosis* (63), indicating the pivotal role of sigH across mycobacterial species.

Consistent with the estimated large regulon of SigH, a significant difference in survival rates between the ΔsigH and wild-type strains was observed inside activated bovine macrophages. Intracellular growth of the wild-type *M. avium* subsp. *paratuberculosis* strain was not inhibited regardless of the activation state up to 8 days postinfection. This observation was in corroboration with the earlier findings which showed that activated bovine monocytes were inadequate to inhibit intracellular growth of *M. avium* subsp. *paratuberculosis* up to 9 days after infection as determined by the CFU method (69). In contrast, viability of the ΔsigH mutant was significantly impaired, indicating an important function of sigH for the intracellular growth of *M. avium* subsp. *paratuberculosis*, possibly by blocking IFN-γ activity as suggested earlier (23). In recent studies, clues have been obtained on macrophage interaction with *M. avium* subsp. *paratuberculosis* that indicate the capacity of this pathogen to subvert host immune responses by blocking the ability of mononuclear phagocyte maturation (23, 70, 71). Although it is tempting to speculate that the ΔsigH mutant failed to interfere with macrophage maturation, especially when preactivated with IFN-γ, more experiments are needed to fully understand the mechanisms that sigH could play during macrophage infection. The survival profile of *M. avium* subsp. *paratuberculosis* constructs in MDM was further supported by the inability of the ΔsigH mutant to survive in mice. Both bacteriological and histological analyses displayed impaired organ colonization of the ΔsigH mutant with a low inflammatory response. However, we did not find any comparative differences in liver organs infected with the wild-type and ΔsigH mutant strains. A recent study showed that the *M. tuberculosis* ΔsigH mutant was completely attenuated in nonhuman primates (72), a better experimental model than mice for studying human tuberculosis (57). It will be interesting and important to examine the survival of the *M. avium* subsp. *paratuberculosis* ΔsigH mutant in a ruminant model of *paratuberculosis* (e.g., goat).

In conclusion, our analyses indicated significant changes in mycobacterial gene expression during macrophage survival, most likely under the control of sigH and other sigma factors. The activation status of macrophages also directs the mycobacterial response to a specific stress-responsive profile. We demonstrated that sigH offers a massive temporal response on the *M. avium* subsp. *paratuberculosis* transcriptome to cope with the adverse effects of oxidative stress. Our data indicate that sigH could play a critical role during infection, and activation of its regulon is required for replication and full virulence of *M. avium* subsp. *paratuberculosis*. Further interrogation of these sigma factors and their regulatory networks should ultimately furnish a greater understanding of *M. avium* subsp. *paratuberculosis* pathogenesis and help design a better approach for controlling Johne's disease.

Example 2

References cited in this Example are listed in the section of References as "References cited in Example 2."

Materials and Methods

Bacterial Strains.

*M. avium* subsp. *paratuberculosis* K10 and *M. smegmatis* mc$^2$155 strains were grown in Middlebrook 7H9 broth and on Middlebrook 7H10 plates as previously described (2,19). For cloning, *Escherichia coli* DH5α and HB101 were used as host cells. To generate an *M. avium* subsp. *paratuberculosis* mutant, a specialized transduction protocol was adopted to delete the sigL/MAP4201 gene using the *M. avium* subsp. *paratuberculosis* K10 strain (19,25). Primers were designed to amplify ~750 bp PCR fragments flanking each end of the sigL coding region and cloned into pYUB854 (19). The resulting vector was used to generate sigL deleted mutant, *M. avium* subsp. *paratuberculosis* ΔsigL, according to the methods described elsewhere (26). Genotype of the *M. avium* subsp. *paratuberculosis* ΔsigL was confirmed by PCR and sequence analysis (19). To complement the *M. avium* subsp. *paratuberculosis* ΔsigL, a ~4-kb fragment, encompassing sigL with its 5' regulatory region and the distal genes (MAP4202-MAP4205), was amplified by PCR and cloned into pMV306 (24). The *M. avium* subsp. *paratuberculosis* ΔsigL strain was transformed with this recombinant construct and genotype of the complemented strain (*M. avium* subsp. *paratuberculosis* ΔsigL: sigL) was identified by PCR analysis. A similar approach was applied to complement *M. tuberculosis* mutant strain lacking such alternative sigma factor (27).

Stress Phenotype of *M. avium* Subsp. *paratuberculosis*.

*M. avium* subsp. *paratuberculosis* cultures were grown to log phase ($OD_{600}$=0.5-1.0) and 200 μl spread on 7H10 plates. For disk diffusion assay (DDA), paper discs (6-mm, Whatman, Piscataway, N.J.) containing 20 μl of 0.5, 1, or 1.5M diamide (oxidative stressor) and 1, 2, or 3% sodium dodecyl sulfate (SDS;cell wall stressor) were placed on each of the spread plate. Plates were incubated at 37° C. until a thick confluent lawn developed. To determine sustained effect of stressor on the viability of bacilli, after washing with PBS, *M. avium* subsp. *paratuberculosis* cultures were exposed to the acidified 7H9 broth (pH 5.5 obtained by adding HCl) containing 0.3% bovine bile (cell wall stressor) and aliquots were collected at 0, 4, 15, 24, 48, and 72 h to monitor their viability by colony forming units (CFU) (19).

Cell Culture and Infection.

The mouse macrophage cells (J774A.1) were regularly maintained as described elsewhere (19). To activate macrophages, cells were pretreated overnight (18 h) with 100 U/ml recombinant murine IFN-γ (Pepro Tech, Rocky Hill, N.J.) before infection with *M. avium* subsp. *paratuberculosis* strains (19). For cell infection studies, wild-type and mutant strains were added to macrophage monolayers (multiplicity of infection [MOI], 20:1). Following incubation at 37° C. in 5% $CO_2$ for 3 h, macrophage monolayers were washed twice with warm PBS to remove extracellular bacteria and RPMI-1640 medium containing 5% fetal bovine serum was added. Cells were lysed at 1, and 8 days post-infection for bacterial CFU counts. To examine *M. avium* subsp. *paratuberculosis* ΔsigL survival in bovine monocyte-derived macrophages (MDM), MDM cells were isolated from peripheral blood of three cows and cell infection studies were performed as described in detail elsewhere (19).

Mouse Infections.

All animal experiments used in this study were performed according to the protocols approved by the Institutional Animal Care and Use Committee, UW-Madison. For the virulence study, two groups (N=15 per group) of female BALB/c mice (Harlan Laboratories, Indianapolis, USA) were challenged intraperitoneally (i.p) with the wild-type and mutant strains. Infection inocula (~2×10$^8$ CFU/mouse) of the two strains were similar as determined by plate count on the day of infection. Mouse groups (N=5) were sacrificed at 3, 6 and 12 weeks post-infection (WPI), and organ samples were collected for bacterial CFU enumeration and histopathological examinations as described before (19). For the immunization studies, female C57BL/6 mice (Taconic, Hudson, N.Y.) were used. Mock group (N=12) was immunized with PBS buffer while *M. avium* subsp. *paratuberculosis* ΔsigL mice group (N=14) received ~2×10$^6$ CFU in 0.2 ml PBS subcutaneously (s.c.) into the neck scruff twice, 2 weeks apart. Four weeks following booster dose, mice were challenged i.p. with ~7×10$^8$ CFU wild-type *M. avium* subsp. *paratuberculosis* strain as determined by plate count on the day of infection. Mouse groups (N=4-6) were sacrificed at 6 weeks post-immunization and 6 and 12 weeks post-challenge (WPC), and organ samples were collected for bacterial CFU counts, histopathological examinations, and immune responses.

Evaluation of Immune Responses.

Mouse spleens were collected aseptically and homogenized by gentle mechanical disruption. Following spleen cell isolation, splenocytes were cultured in duplicate in round bottom 96-well tissue culture plates with 1×10$^6$ cells/well (28). Cells were re-stimulated in vitro with 10 μg/ml Johnin purified protein derivative (PPD) (NVSL, Ames, Iowa) for 48 and 72 h. Cell supernatants were collected and analyzed for cytokines by ELISA kit according to the manufacturer's instructions (BioLegend, San Diego, Calif.). To determine humoral immune response, sera were prepared from mouse blood and *M. avium* subsp. *paratuberculosis* specific antibody (anti-PPDj antibodies) was detected by ELISA using Horseradish peroxidase conjugated rabbit anti-mouse antibody (Pierce, Rockford, Ill.) (29).

Statistical Analysis.

Student's t test was performed to compare differences in mouse immune responses and bacterial CFU counts from in vitro stress treatments. Mann-Whitney U test was used to compare bacterial loads in mouse organs. A probability value of <0.05 was considered significant.

Results

Effect of sigL Mutation on Viability of *M. avium* Subsp. *paratuberculosis* Under Stress.

Figure 4A:
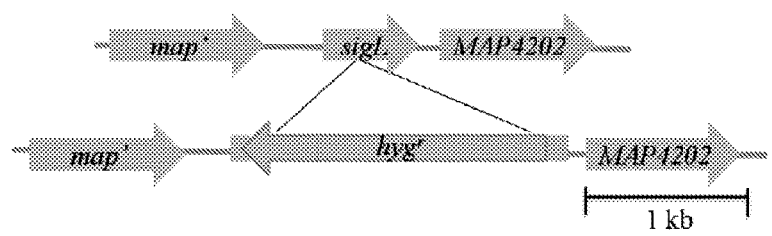
FIG. 4A. Construction of *M. avium* subsp. *paratuberculosis* ΔsigL using wild-type *M. avium* subsp. *paratuberculosis* strain. A Physical map displaying the deletion of sigL (MAP4201) gene with homologous recombination via pYUB854 cosmid shuttle cloning vector, which resulted in the deletion of ~750 bp coding region and the insertion of a ~2 kb region encoding a hygromycin resistance cassette.
Figure 4B:
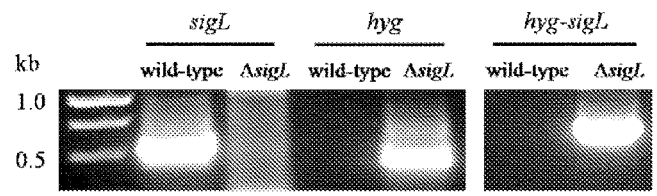
FIG. 4B. Construction of *M. avium* subsp. *paratuberculosis* ΔsigL using wild-type *M. avium* subsp. *paratuberculosis* strain. The *M. avium* subsp. *paratuberculosis* ΔsigL mutant was confirmed with PCR and sequence verification using genomic DNA from the wild-type and the mutant strains. Primer pairs were designed for the sigL region, hygromycin resistance gene ($hyg^r$), or the recombinant region after allelic exchange. A 1.5% agarose gel showed amplicons from the sigL region only when wild-type genomic DNA was used (lane 1), whereas $hyg^r$ was amplified only from the *M. avium* subsp. *paratuberculosis* ΔsigL mutant genomic DNA (lane 4). Lane 6 showed amplicon from the recombinant region only when *M. avium* subsp. *paratuberculosis* ΔsigL mutant genomic DNA was used.
Figure 4C:
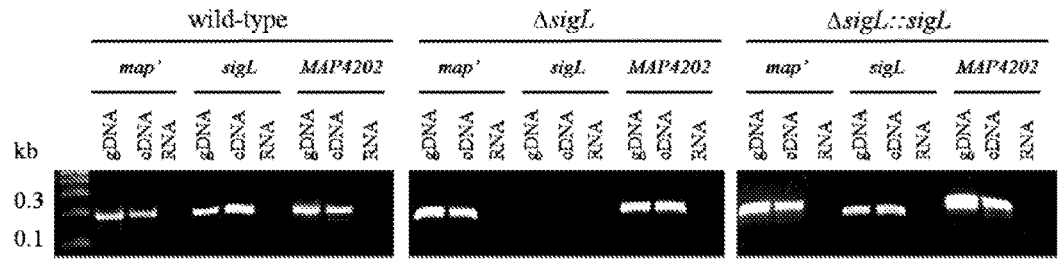
FIG. 4C. Construction of *M. avium* subsp. *paratuberculosis* ΔsigL using wild-type *M. avium* subsp. *paratuberculosis* strain. The polarity of the *M. avium* subsp. *paratuberculosis* ΔsigL knockout mutant was assessed using reverse-transcriptase PCR analysis to check for transcription of its neighboring genes. In the wild-type (left) and complemented (right) strains, positive bands show that map', sigL and the downstream gene MAP4202 are both encoded in the genome and transcribed (amplified from cDNA), with no amplification from RNA used as a negative control. In the *M. avium* subsp. *paratuberculosis* ΔsigL mutant (middle), the sigL coding region is absent in the genome or as cDNA, but transcripts for the neighboring genes are present.

Recent analysis of *M. avium* subsp. *paratuberculosis* transcriptome during macrophage infection suggested that sigL could be an important factor for *M. avium* subsp. *paratuberculosis* survival inside host macrophages (19). To test this hypothesis, we generated a sigL deletion mutant, *M. avium* subsp. *paratuberculosis* ΔsigL (FIG. 4A-B) and examined survival of this mutant under different stress conditions. Because sigL and its anti-sigma factor (MAP4202) are likely encoded in an operon (24), we examined *M. avium* subsp. *paratuberculosis* ΔsigL strain for possible polarity on the downstream gene, MAP4202. By employing reverse-transcriptase PCR analysis, presence of the MAP4202 transcript was confirmed in the ΔsigL mutant (FIG. 4C).

To examine a potential role for sigL in *M. avium* subsp. *paratuberculosis* response to unfavorable stress conditions, we analyzed the survival of *M. avium* subsp. *paratuberculosis* cultures under both oxidative (diamide) and cell wall stresses (SDS and bovine bile). Growth inhibition zones in disk diffusion assays indicated that *M. avium* subsp. *paratuberculosis* ΔsigL was susceptible to diamide oxidation. Such phenotypic differences also indicated the inability of *M. avium* subsp. *paratuberculosis* ΔsigL to survive under SDS stress when compared to the wild-type and complemented strains. Bile tolerance was also evaluated by culturing of the *M. avium* subsp. *paratuberculosis* strains in the presence of 0.3% bovine bile (oxgall). This concentration of bile is likely encountered by the bacteria within the intestinal content following oral infection (30). In addition, because of the ability of *M. avium* subsp. *paratuberculosis* to resist killing by acidic conditions (31), we made culture broths slightly acidic (pH 5.5) to partially mimic the physiological condition that *M. avium* subsp. *paratuberculosis* would encounter following infection in the gastrointestinal tract (e.g. abomasum of a cow and stomach of a human). Survival levels showed a significant drop in the viability of the *M. avium* subsp. *paratuberculosis* ΔsigL at 4 h post-exposure to bovine bile compared to the wild-type and complemented strains. This difference in bacterial survival for *M. avium* subsp. *paratuberculosis* ΔsigL was increased by more than 1.0 log at 24 h and the viability of the mutant continued to decline at later times suggesting that sigL is important in rendering resistance when bacteria experience initial bactericidal barriers in the host. Because complementation of the *M. avium* subsp. *paratuberculosis* ΔsigL restored wild-type phenotype under these stress conditions, the complemented strain was not included in further experiments.

Intracellular Survival within Macrophages.

Because sigL was up-regulated inside activated murine macrophages (19), we examined intracellular survival of *M. avium* subsp. *paratuberculosis* ΔsigL in the IFN-γ pretreated murine macrophages. Our analysis showed an increase in the number of wild-type *M. avium* subsp. *paratuberculosis* at 8 days relative to the numbers obtained at day 1 post-infection whereas viability of the *M. avium* subsp. *paratuberculosis* ΔsigL was significantly reduced at this time. To use a more relevant model for *M. avium* subsp. *paratuberculosis* infection, we evaluated the persistence of the *M. avium* subsp. *paratuberculosis* ΔsigL both in resting and IFN-γ-activated bovine monocyte-derived macrophages (MDM cells), the natural host cell for *M. avium* subsp. *paratuberculosis*. At 8 days post-infection, the number of wild-type bacilli increased over twofold compared to the numbers obtained at day 1 in the resting MDM cells. Specifically, naive and IFN-γ pretreated MDM cells were infected with *M. avium* subsp. *paratuberculosis* ΔsigL and wild-type *M. avium* subsp. *paratuberculosis* strains. Cells were lysed at 1, and 8 days post-infection and numbers of viable bacilli were determined by serial dilutions for CFU plating. The survival level at 8 days was relative to the viable counts of bacterial strains at day 1. Survival data represent the average of macrophage infections collected from three different donor animals with significance levels in Student's t test (*p<0.05).

In contrast, viability of the *M. avium* subsp. *paratuberculosis* ΔsigL was significantly reduced almost by half indicating a potential function for sigL in defending *M. avium* subsp. *paratuberculosis* against intracellular stress. A similar survival trend for the *M. avium* subsp. *paratuberculosis* ΔsigL was seen inside IFN-γ pretreated MDM cells whereas this activation status did not result in more inhibitory effect on the survival of wild-type bacilli. Collectively, survival assays indicated that deletion of sigL affected *M. avium* subsp. *paratuberculosis* viability following exposure to stress conditions suggesting a significant function for sigL in defending *M. avium* subsp. *paratuberculosis* against intracellular insults.

Virulence Analysis of *M. avium* Subsp. *paratuberculosis* ΔsigL Strain.

To evaluate the contribution of SigL to *M. avium* subsp. *paratuberculosis* virulence, we examined persistence of the *M. avium* subsp. *paratuberculosis* ΔsigL using the murine model of *paratuberculosis*. The survival pattern indicated significant attenuation for *M. avium* subsp. *paratuberculosis* ΔsigL as early as 3 WPI in all of the examined organs. In the spleen, viability of *M. avium* subsp. *paratuberculosis* ΔsigL was reduced by more than 1-log and 2-log orders relative to the wild-type strain at 6 and 12 WPI, respectively. Similarly, colonization levels of the mutant strain in the liver were significantly lower compared to the parental strain at all examined time points. Interestingly, *M. avium* subsp. *paratuberculosis* ΔsigL did not persist in the intestines as we were unable to detect any bacteria (limit of detection 20 CFU) at 6 and 12 WPI.

The histological analysis revealed mild to moderate granulomatous inflammation in the liver tissues at both 3 and 6 WPI with either of the *M. avium* subsp. *paratuberculosis* strains with higher lymphocytic infiltration in the mice infected with *M. avium* subsp. *paratuberculosis* ΔsigL. At 12 WPI, *M. avium* subsp. *paratuberculosis* ΔsigL infected animals showed less granulomatous inflammation indicating reduced ability of *M. avium* subsp. *paratuberculosis* ΔsigL compared with wild-type bacilli to establish an infection in animals. In accordance with the bacterial organ burden data, Ziehl-Neelsen staining showed higher numbers of acid-fast bacilli in mice liver infected with the wild-type strain relative to the *M. avium* subsp. *paratuberculosis* ΔsigL at all examined time points. A similar observation was noticed for the spleen and intestine tissues (data not shown). Both bacterial organ colonization and histological data analyses suggested that *M. avium* subsp. *paratuberculosis* ΔsigL was attenuated for survival, compared to the wild-type strain in the mice model of infection.

Immunization with *M. avium* Subsp. *paratuberculosis* ΔsigL.

Because sigL encodes a mycobacterial GGR (32) and was critical for *M. avium* subsp. *paratuberculosis* survival in the present study, we investigated the vaccine potential of *M. avium* subsp. *paratuberculosis* ΔsigL in a challenge model of murine *paratuberculosis* (FIG. 5A). To examine immunogenicity of the mutant strain, groups of mice were immunized twice with *M. avium* subsp. *paratuberculosis* ΔsigL and 6 weeks post-immunization (WPI) mice organs were analyzed for bacterial content. Two immunizations with this mutant resulted in low colonization ($2 \times 10^2$ CFU) in the liver whereas no bacteria were detected (limit of detection 20 CFU) in the intestine or spleen (data not shown). To evaluate vaccine induced immune responses before challenge; ELISA was used to estimate levels of key cytokines in stimulated spleen cells. Statistical analysis revealed significantly ($p<0.05$) high level of IFN-γ secretion in the *M. avium* subsp. *paratuberculosis* ΔsigL immunized mice compared to naïve animals (FIG. 5B). Because of the importance of T-helper 17 cells (33) for intracellular bacterial infection, we examined IL-17A production in the immunized animals. However, we did not find any detectable levels for IL-17A at 6 WPI. Additionally, the mice group vaccinated with *M. avium* subsp. *paratuberculosis* ΔsigL had significantly ($p<0.05$) higher anti-PPDj IgG level (FIG. 5C). Thus, both IFN-γ and IgG data suggested ability of the *M. avium* subsp. *paratuberculosis* ΔsigL strain to induce enhanced immune responses.

Protection Against Challenge with *M. avium* Subsp. *paratuberculosis*.

Figure 6A:
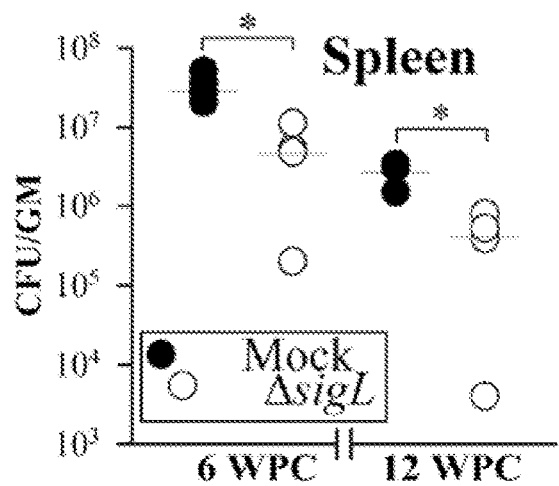
FIG. 6A. Protective efficacy of immunization. At 6 weeks following vaccination, mice received a challenge dose containing ~7×10⁸ CFU wild-type *M. avium* subsp. *paratuberculosis* strain i.p (see FIG. 5A). Following challenge, mice groups (N=4) were sacrificed at 6 and 12 weeks and bacterial burden was analyzed in the spleen.
Figure 6B:
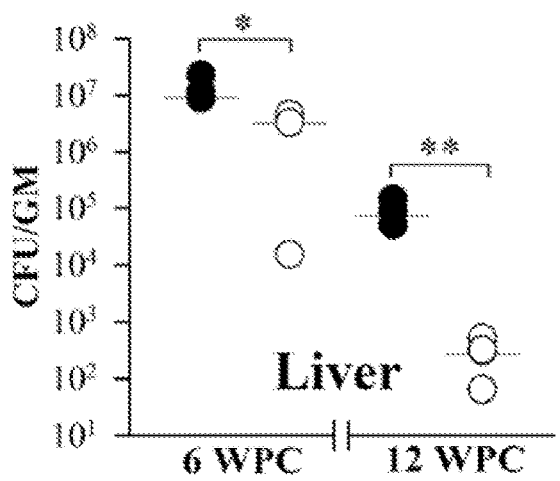
FIG. 6B. Protective efficacy of immunization. At 6 weeks following vaccination, mice received a challenge dose containing ~7×10⁸ CFU wild-type *M. avium* subsp. *paratuberculosis* strain i.p (see FIG. 5A). Following challenge, mice groups (N=4) were sacrificed at 6 and 12 weeks and bacterial burden was analyzed in the liver.
Figure 6C:
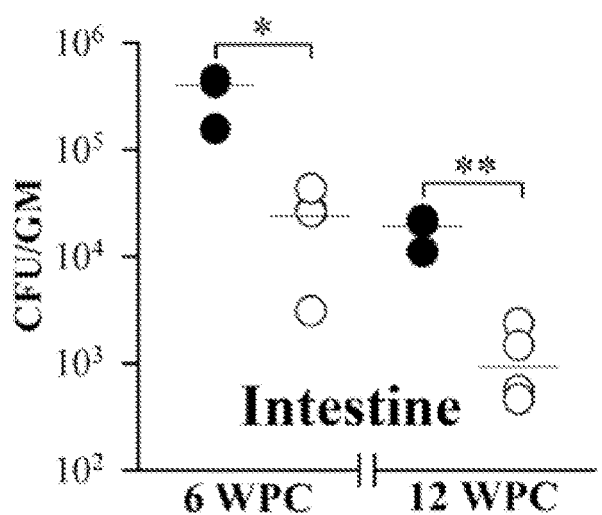
FIG. 6C. Protective efficacy of immunization. At 6 weeks following vaccination, mice received a challenge dose containing ~7×10⁸ CFU wild-type *M. avium* subsp. *paratuberculosis* strain i.p (see FIG. 5A). Following challenge, mice groups (N=4) were sacrificed at 6 and 12 weeks and bacterial burden was analyzed in the intestine. Horizontal lines indicate median value. Statistical analyses were done using student's t test and Mann-Whitney test to evaluate differences in bacterial organ load among mice groups vaccinated with the PBS (mock) or *M. avium* subsp. *paratuberculosis* ΔsigL mutant.

To examine the vaccine potential of sigL-based mutant, groups of mice were vaccinated with PBS (control) or *M. avium* subsp. *paratuberculosis* ΔsigL live strain and challenged with the virulent *M. avium* subsp. *paratuberculosis* K10 strain following 6 WPI (FIG. 5A). At 6 weeks post challenge (WPC), the ΔsigL mice group had a significant reduction in the bacterial load in spleen and liver (~0.5 log) compared to the PBS-vaccinated mice (FIG. 6A, B). More importantly, a higher level of bacterial load reduction (~1 log) was observed in the intestine (FIG. 6C), an important organ for *M. avium* subsp. *paratuberculosis* infection. A similar colonization pattern was observed for all examined organs (spleen, liver, intestine) at 12 WPC where the level of bacterial reduction reached >1 log.

For histological examination, we focused our efforts on the liver because it is the most reflective organ for *M. avium* subsp. *paratuberculosis* infection (34). Liver sections from ΔsigL immunized animals displayed lower granulomatous scores and smaller size granulomas than the PBS-control group at 6 and 12 WPC (FIG. 7A-B). In addition, low numbers of acid-fast bacilli were observed when liver sections were stained with Ziehl-Neelsen stain, another support for colonization data discussed above. Interestingly, sections from the intestines of the ΔsigL-immunized mice appeared normal compared to mock infected mice with no detectable acid-fast bacteria in Ziehl-Neelsen stained sections at both at 6 and 12 WPC (FIG. 7C-D). Overall, reduction in *M. avium* subsp. *paratuberculosis* colonization levels combined with histological scores indicated the ability of the ΔsigL mutant to control tissue damage by a challenge with the virulent strain of *M. avium* subsp. *paratuberculosis*.

Expansion of Immune Responses Following Challenge in Immunized Mice.

Figure 6D:
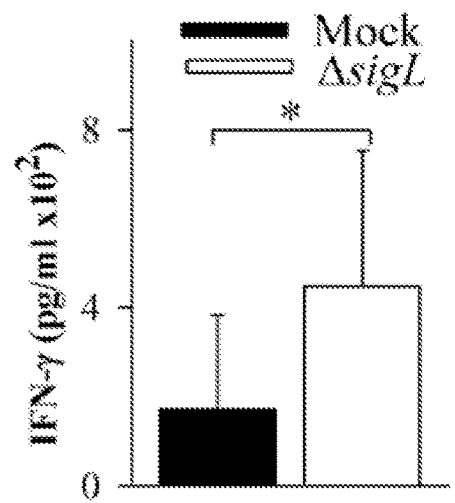
FIG. 6D. Secretion of IFN-γ production (6WPC) from the cell supernatant was measured by ELISA. The histograms show mean values with error bars representing the standard deviation. *p<0.05, **p<0.01.

To evaluate expansion of the cellular immune response following challenge, splenocytes of immunized and challenged mice were analyzed for the production of key cytokines associated with protection against *paratuberculosis* (35,36). As shown in FIG. 6D, PPD-stimulated splenocytes from ΔsigL-immunized and challenged mice secreted significantly higher levels of IFN-γ than that of control animals at 6WPC, indicating increased levels of T cell activity (T-helper 1 cells) in the animals that received ΔsigL mutant. However, at 12 WPC there was no significant difference in IFN-γ response between these two groups of animals. Our data also showed a better ability, even though not significant, of the *M. avium* subsp. *paratuberculosis* ΔsigL vaccinated animals to induce PPD-specific IL-17A secretion compared to the mock challenged group at 6WPC. Taken together, the colonization, histological and immune response levels suggested that *M. avium* subsp. *paratuberculosis* ΔsigL induced protective immunity against challenge with virulent *M. avium* subsp. *paratuberculosis* strain.

Discussion

Infection with *M. avium* subsp. *paratuberculosis* represent a major threat (Johne's disease) to dairy animals (11,14) with the potential spread to human with the likely involvement in several diseases (7-10,12). Earlier reports indicated that *M. avium* subsp. *paratuberculosis* count on a large number of sigma factors (N=19) to establish the infection and survive diverse stress conditions (19,37). In this study, we have targeted sigL because of its activation during early macrophage infection suggesting a role to control important stage(s) of *M. avium* subsp. *paratuberculosis* pathogenesis following oral infection (19). Moreover, the orthologous sigL deletion mutant, *M. tuberculosis* ΔsigL, in *M. tuberculosis* was less lethal for mice relative to the wild-type strain (32). However, unlike *M. tuberculosis* ΔsigL (24), our analysis indicated that deletion of sigL affected ability of *M. avium* subsp. *paratuberculosis* to survive exposure to intracellular stimuli including oxidative stress and damaging the mycobacterial cell wall stresses (e.g. diamide and SDS) (38-40). This mutant was also unable to survive both naïve and activated macrophages to similar levels, an indication of the significant attenuation of this mutant. This intracellular survival defect of the mutant was further verified by the poor ability of *M. avium* subsp. *paratuberculosis* ΔsigL to replicate in mouse tissues. Both histological and bacteriological analyses revealed reduced organ colonization of the *M. avium* subsp. *paratuberculosis* ΔsigL with low inflammatory scores compared to the parental strain. Interestingly, this result was in contrast to the reports where orthologous *M. tuberculosis* ΔsigL survived in the mice organs to the same level as the wild-type strain suggesting a more comprehensive and dynamic role for sigL in *M. avium* subsp. *paratuberculosis* survival and pathogenesis (24,32). However, the nature and mechanisms employed by sigL to enable *M. avium* subsp. *paratuberculosis* virulence remain elusive.

The alternative sigma factor (e.g. sigE) mutant strains were targeted for the vaccine development and found to provide protection against infection with pathogenic bacteria including mycobacteria (41,42). In our study, observations gained from both in vitro and murine model experiments encouraged us to investigate the vaccine potential of *M. avium* subsp. *paratuberculosis* ΔsigL as a live attenuated vaccine against *M. avium* subsp. *paratuberculosis* infection in mice. The murine model of *paratuberculosis* represent an important screening tool (43,44) to examine vaccine candidates before testing in a more expensive goat model, despite the associated shortcomings of the murine model (no diarrhea or shedding of bacteria). In our hands, mice that received *M. avium* subsp. *paratuberculosis* ΔsigL were very efficient in producing IFN-γ (e.g. 6WPI), an important cytokine involved in controlling mycobacterial infection (45). The decline in IFN-γ is often associated with the onset of clinical JD in ruminants (35,46). Importantly, culturing tissue samples from immunized animals indicated the ability of *M. avium* subsp. *paratuberculosis* ΔsigL to persist in animals following immunization but to a low level which could be a critical factor in inducing protective immune responses.

Controlling *M. avium* subsp. *paratuberculosis* infection is dependent on developing vaccines that reduce bacterial colonization and shedding from infected animals. Earlier studies demonstrated the potential use of *M. avium* subsp. *paratuberculosis* mutants (e.g. WAg915, *M. avium* subsp. *paratuberculosis* ΔleuD) as live attenuated vaccine candidates in the murine model of *paratuberculosis* (44,47). WAg915 mutant strain (*M. avium* subsp. *paratuberculosis* ΔppiA), defective in the peptidyl-prolyl cis-trans-isomerase, showed mild attenuated phenotype relative to the wild-type strain and provided limited protection in mouse organ only at later stages after challenge with parental *M. avium* subsp. *paratuberculosis* strain (47), whereas the attenuated *M. avium* subsp. *paratuberculosis* ΔleuD, defective in leucine biosynthesis, exhibited some protection following challenge (44). In our experiment, *M. avium* subsp. *paratuberculosis* ΔsigL was attenuated in macrophages and in mice but persisted in murine tissues up to the time of challenge. Ability to persist following immunization could be responsible for the generated protective immunity, which was more efficient to reduce *M. avium* subsp. *paratuberculosis* colonization compared to the Wag915 candidate (47). However, it is not clear whether *M. avium* subsp. *paratuberculosis* ΔsigL could provide better protection compared to the *M. avium* subsp. *paratuberculosis* ΔleuD because the previous study examined *M. avium* subsp. *paratuberculosis* bacilli in mouse tissues by Ziehl-Neelsen staining which is less sensitive compared to the tissue culturing (48,49). We further evaluated longevity of immune responses in the mouse groups following challenge and these data suggest that *M. avium* subsp. *paratuberculosis* ΔsigL immunized mice maintained strong T-cell responses with secretion of higher IFN-γ and IL-17 at 6WPC, despite the later not being significant compared to the mock infected group.

Overall, an isogenic mutant of *M. avium* subsp. *paratuberculosis* lacking sigL had limited ability to survive in macrophages or mice, most likely because of a defective bacterial cell wall. Such an attenuated strain of *M. avium* subsp. *paratuberculosis* (ΔsigL) persisted in murine tissue following subcutaneous immunization and generated a robust immune response. The generated immune responses were sufficient to reduce tissue colonization and lesion scores in animals following a challenge with the wild-type strain of *M. avium* subsp. *paratuberculosis*. Further vaccine testing in natural hosts of Johne's disease, e.g. goats or calves, will demonstrate the viability of developing an effective control strategy against *paratuberculosis* in both animals and humans. In general, approaches used to investigate sigL in *M. avium* subsp. *paratuberculosis* could be adopted to examine the role and potential use of other global gene regulators in pathogenesis and control of intracellular pathogens.

Example 3

References cited in this Example are listed in the section of References as "References cited in Example 3."

Survival of GGR Mutants in the Murine Model of *paratuberculosis*.

Figure 8A:
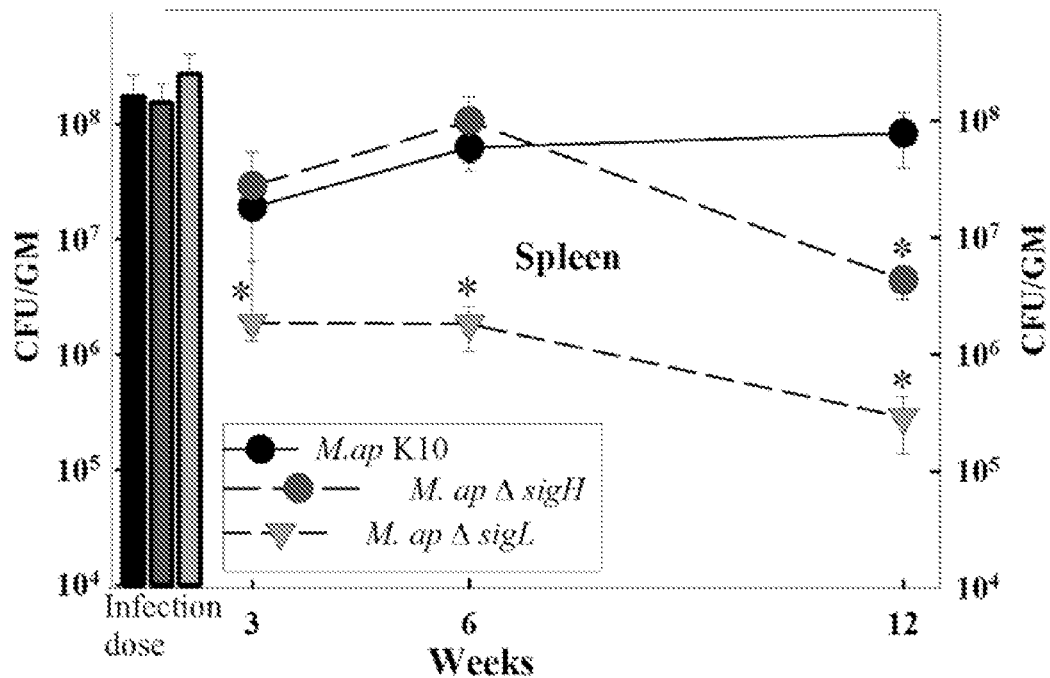
FIG. 8A. Virulence of *M. ap* mutants in BALB/c mice (n=15/group) following IP. Spleen (circle).
Figure 8B:
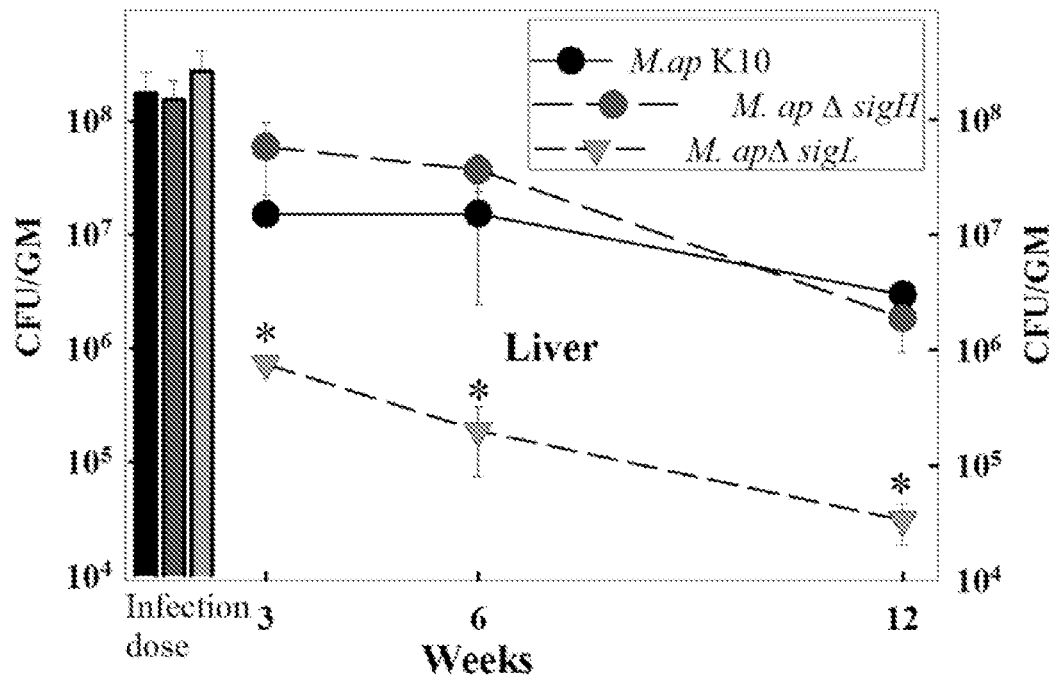
FIG. 8B. Virulence of *M. ap* mutants in BALB/c mice (n=15/group) following IP. Liver (square) were collected at 3, 6, and 12 WPI. Colonization levels were compared to *M. ap* K10 (Continued line). * denotes significant difference between groups in Student's t-test (p<0.05).

To assess the role of sigH and sigL in *M. ap* virulence, we investigated the persistence of the each mutant in mice. The initial growth kinetic of the wild-type and ΔsigH mutant strains was similar, with an equal burden of bacteria in liver, intestine and spleen up to 6 WPI (FIG. 8). However, at 12 WPI, colonization levels were significantly reduced for ΔsigH compared to its parental strain only in spleen and intestine (p<0.01 and p<0.05, respectively), suggesting a role for sigH in the long term survival of *M. ap* in mice. For the ΔsigL mutant, bacterial colonization levels were significantly reduced in spleen, liver and intestine at all times post infection (FIG. 8) compared to K10, suggesting a pivotal role for sigL in the pathogenesis of *M. ap*.

Figure 9A:
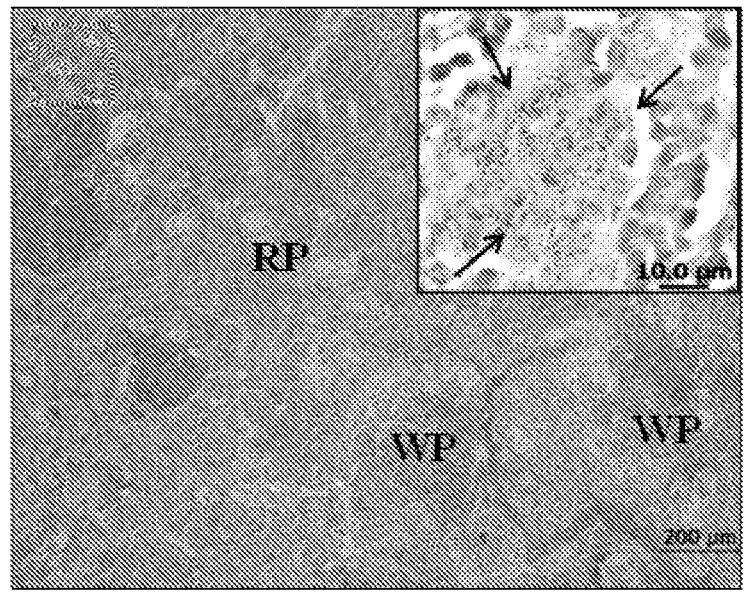
FIG. 9A. Pathology of spleen collected from mice infected with wild type *M. ap*.
Figure 9B:
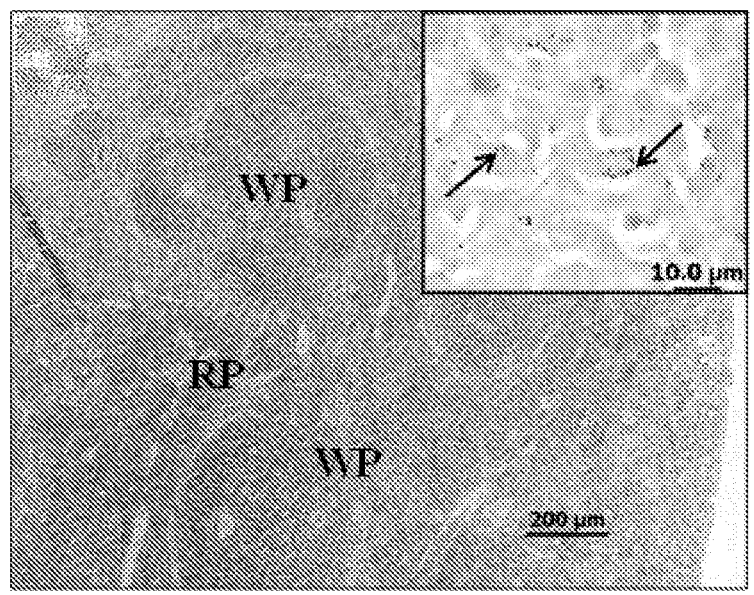
FIG. 9B. Pathology of spleen collected from mice infected with isogenic mutant ΔsigH. H&E stained sections with 100× (Bar=200 μm) are shown. Inset images (1000×, Bar=10 μm). WP, white pulp; RP, red pulp.

Interestingly, when the ΔsigH mutant of *M. tuberculosis* was used to challenge mice, no differences in bacterial load were observed in mouse organs compared to the wild-type strain (54), suggesting a more significant role for sigH in *M. ap*. Consistent with the colonization data, Ziehl-Neelsen staining of spleen showed higher acid fast bacilli in mice infected with wild-type strain compared to ΔsigH mutant at 12 WPI (FIG. 9).

Taken together, our data indicated that both ΔsigH and ΔsigL mutants were attenuated in the murine model of *paratuberculosis* compared to the wild-type *M. ap* strain.

RNA Sequencing for Transcriptional Profiling.

During the last decade, it is evident that the use of DNA microarrays has greatly contributed to our understanding of the genetic basis of bacterial infections, including infection with *M. ap* (42,55-58). Recently, large scale sequencing approaches were developed for gene expression profiling to overcome problems associated with DNA microarrays (59). The use of Next-generation sequencers enabled us to sequence all transcripts in a given RNA sample, hence named RNA sequence (RNA-Seq) profiling. This naming reflects the ability of the high throughput sequencers (e.g. HighSeq2000, Roche 454) to be used for in-depth sequencing of millions of transcripts in a single run (59-61). The RNA-Seq approach has already been successfully applied in several systems, both mammalian and bacterial, (61) including *M. tuberculosis* and *M. ap* in our laboratory (62) (see below). Some key benefits of RNA-Seq over microarrays include less biased transcriptome data acquisition, actual sequences for transcripts that can show SNPs and antisense transcription, less complex data analysis; improved correlation between laboratories and increased sensitivity of low transcript numbers (63-65).

Because of the global nature of transcriptional regulation under control of a factors, we pursued the characterization of the sigH transcriptome using RNA-Seq profiling utilizing an Illumina-based sequencer operated by the University of Wisconsin Biotechnology Center (UWBC). Our stress experiments showed that the ΔsigH mutant was hypersensitive to elevated temperature and diamide exposure, each resulting in impaired growth. Accordingly, we hypothesize that sigH may play an important role in directing transcriptional control under unfavorable environmental conditions. To test this hypothesis, both wild-type *M. ap* K10 and ΔsigH mutant transcriptomes were profiled before and after diamide exposure. Briefly, cultures grown to mid-log phase ($OD_{600}$=0.5) from both K-10 and its isogenic mutant, ΔsigH, were centrifuged (3,200×g) for 15 min at 4° C. for total RNA extraction as outlined before (32). Extracted RNA samples were treated with DNAse I (Ambion) to eliminate residual genomic DNA and then treated with MICROBExpress (Ambion, Austin) to enrich bacterial mRNA and reduce the amount of rRNA. Following a standard protocol for cDNA generation in our laboratory (42), all samples were sent to the UWBC for library construction and sequencing on the Illumina/GAIIx sequencing platform using 100-bp, paired end fragments. As a testament of the high resolution analysis of RNA-Seq profiling, we were not able to detect the presence of only 18 or 20 genes in both samples from *M. ap* K10 or ΔsigH, respectively (Table 2).

TABLE 1

Sequencing run statistics on M. ap samples.

| | M. ap K10 | M. ap K10 ΔsigH |
|---|---|---|
| Material Submitted | 2 μg mRNA | 2 μg mRNA |
| Total Reads | 74, 747, 582 | 53, 305, 460 |
| Read Length | 100 bp | 100 bp |
| Total Reads Mapped | 57, 477, 920 | 41, 101, 069 |
| Reads mapped in pairs | 53, 359, 286 | 36, 887, 226 |
| Reads mapped to rRNA or tRNA | 54, 209, 373 | 37, 081, 401 |
| Reads not mapped | 16, 903, 464 | 11, 874, 445 |
| Most sequenced mRNA (reads) | MAP 1975 (1, 286, 560) | MAP 1975 (1, 390, 707) |
| Transcripts not detected | 18 | 20 |

Examine the Vaccine Potential of GGR *M. ap* Mutants.

Figure 10A:
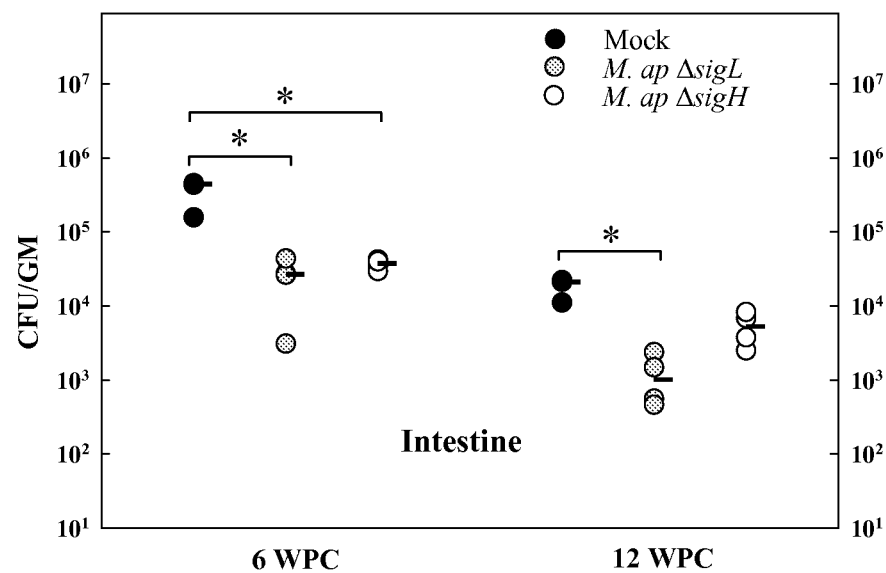
FIG. 10A. Vaccine potential of *M. ap* a factors deleted mutants. Recovery of virulent *M. ap* (cfu/g tissue) from Intestine. of mice immunized with mock (PBS), ΔsigL or ΔsigH at 6 and 12 weeks following challenge. Colony forming unit (cfu) counts are shown as a scatter plot where the bar represents the median. *p<0.05.
Figure 10B:
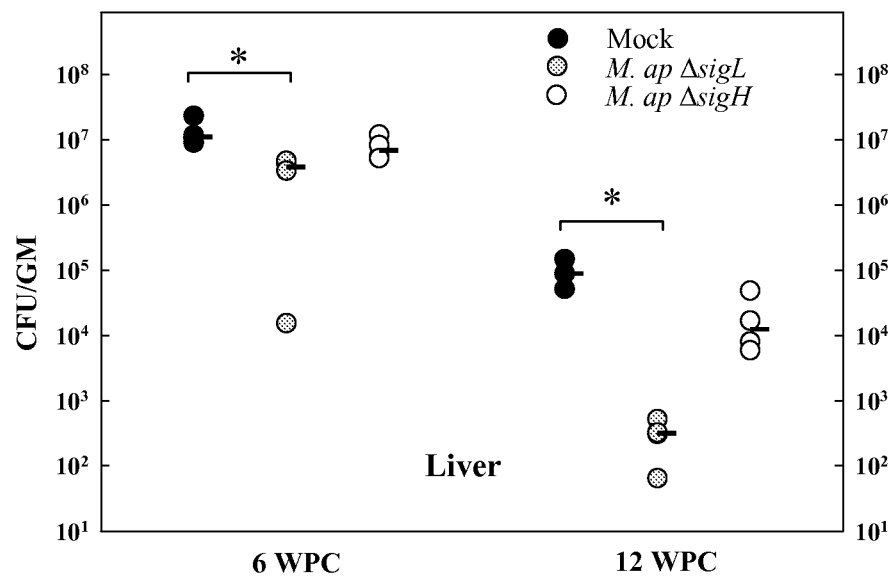
FIG. 10B. Vaccine potential of *M. ap* a factors deleted mutants. Recovery of virulent *M. ap* (cfu/g tissue) from Liver of mice immunized with mock (PBS), ΔsigL or ΔsigH at 6 and 12 weeks following challenge. Colony forming unit (cfu) counts are shown as a scatter plot where the bar represents the median. *p<0.05.

Because they control a large number of genes, we hypothesize that GGR mutants will be attenuated but able generate enough immune responses to serve as live attenuated vaccines that could control JD. To examine the vaccine potential of ΔsigH and ΔsigL mutants as live-attenuated vaccines, C57BL/6 mice groups (N=11) were vaccinated twice at 2 weeks interval with $10^6$ CFU/mouse via subcutaneous (S/C.) injection. This route of immunization was chosen after evaluating other routes (oral and intra-peritoneal, I/P.) and was found to yield better immunity (data not shown). In addition, immunized mice via the S/C. showed no *M. ap* colonization in their organs when examined at 6 weeks post immunization (WPI). At 6 WPI, immunized mice (N=8/group) were challenged with $2 \times 10^8$ CFU/mouse of the wild-type strain *M. ap* K10 via I/P. Mock-immunized mice with (Phosphate Buffered Saline, PBS) showed the highest colonization levels of *M. ap* in their organs following challenge with *M. ap* K10. On the other hand, mice vaccinated with the attenuated mutants (ΔsigH and ΔsigL) showed a significant reduction in bacterial colony levels in the intestine at 6 weeks post challenge (WPC) (FIG. 10). Only ΔsigL-vaccinated group showed significant reduction in both liver and spleen at this time point. By 12 WPC, only ΔsigL-vaccinated group showed more than 1 log reduction in intestine in all organs (intestine, liver, spleen) compared to the control group (FIG. 10). Overall, ΔsigL immunization was more effective in inducing protection against virulent *M. ap* K10 strain compared to ΔsigH vaccination.

REFERENCES

1. Ghosh, P., C. Hsu, E. J. Alyamani, M. M. Shehata, M. A. Al-Dubaib, A. Al-Naeem, M. Hashad, O. M. Mahmoud, K. B. Alharbi, K. Al-Busadah, A. M. Al-Swailem, and A. M. Talaat. 2012. Genome-wide analysis of the emerging infection with *Mycobacterium avium* subspecies *paratuberculosis* in the Arabian camels (*Camelus dromedarius*). PLoS. One. 7:e31947. doi: 10.1371/journal. pone. 0031947 [ doi]; PONE-D-11-17590 [pii].
2. Yalo Ayele, W., M. Machackova, and I. Pavlik. 2001. The transmission and impact of *paratuberculosis* infection in domestic and wild ruminants. Vet. Med. (Praha) 46:205-224.
3. Nielsen, S. r. S. and N. Toft. 2009. A review of prevalences of *paratuberculosis* in farmed animals in Europe. Preventive Veterinary Medicine 88:1-14. doi:doi: DOI: 10.1016/j.prevetmed.2008.07.003.
4. Nielsen, S. S. and Kennedy, D. Proceedings of the 1st ParaTB Forum. Nielsen, S. S. and Kennedy, D. The 1st ParaTB Forum. Proceedings of the 1st ParaTB Forum, 1-48. 3-22-2007. Brussels, Belgium, International Dairy Federation.
5. National Animal Health Monitoring System. 2008. Johne's Disease on U.S. Dairies, 1991-2007. USDA-APHIS Veterinary Services, Ft. Collins, Colo. 2008.
6. Ott, S. L., S. J. Wells, and B. A. Wagner. 1999. Herd-level economic losses associated with Johne's disease on US dairy operations. Prev. Vet. Med. 40:179-192. doi:S0167-5877(99)00037-9 [pii].
7. NIAA. The cost of Johne's disease to dairy producers National Institute for Animal Agriculture. Springs, Colo. (CO) (2009) 09-69224-00. 2009.
8. Bermudez, L. E., M. Petrofsky, S. Sommer, and R. G. Barletta. 2010. Peyer's patch684 deficient mice demonstrate that *Mycobacterium avium* subsp. *paratuberculosis* translocates across the mucosal barrier via both M cells and enterocytes but has inefficient dissemination. Infect. Immun. 78:3570-3577. doi:IAI.01411-09 [pii]; 10.1128/IAI.01411-09 [doi].
9. Ponnusamy, D., S. Periasamy, B. N. Tripathi, and A. Pal. 2012. *Mycobacterium avium* subsp. *paratuberculosis* invades through M cells and enterocytes across ileal and jejuna mucosa of lambs. Res. Vet. Sci. doi: S0034-5288(12)00301-3 [pii]; 10.1016/j.rvsc.2012.09.023 [doi].
10. Chacon, O., L. E. Bermudez, and R. G. Barletta. 2004. Johne's disease, inflammatory bowel disease, and *Mycobacterium paratuberculosis*. Annu. Rev. Microbiol. 58:329-363.
11. Coussens, P. M., C. J. Colvin, K. Wiersma, A. Abouzied, and S. Sipkovsky. 2002. Gene expression profiling of peripheral blood mononuclear cells from cattle infected with *Mycobacterium paratuberculosis*. Infect. Immun. 70:5494-5502.
12. Coussens, P. M., A. Jeffers, and C. Colvin. 2004. Rapid and transient activation of gene expression in peripheral blood mononuclear cells from Johne's disease positive cows exposed to *Mycobacterium paratuberculosis* in vitro. Microbial. pathogenesis. 36:93-108.
13. Weiss, D. J., O. A. Evanson, M. Deng, and M. S. Abrahamsen. 2004. Sequential patterns of gene expression by bovine monocyte-derived macrophages associated with ingestion of mycobacterial organisms. Microb. Pathog. 37:215-224.
14. Weiss, D. J., O. A. Evanson, M. Deng, and M. S. Abrahamsen. 2004. Gene expression and antimicrobial activity of bovine macrophages in response to *Mycobacterium avium* subsp. *paratuberculosis*. Vet. Pathol. 41:326-337.
15. Wu, C. W., S. K. Schmoller, S. J. Shin, and A. M. Talaat. 2007. Defining the stressome of *Mycobacterium avium* subsp *paratuberculosis* in vitro and in naturally infected cows. Journal of Bacteriology 189:7877-7886.
16. Whittington, R. J., D. J. Marshall, P. J. Nicholls, I. B. Marsh, and L. A. Reddacliff. 2004. Survival and dormancy of *Mycobacterium avium* subsp. *paratuberculosis* in the environment. Appl. Environ. Microbiol. 70:2989-3004.
17. Bannantine, J. P. and J. R. Stabel. 2002. Killing of *Mycobacterium avium* subspecies *paratuberculosis* within macrophages. BMC Microbiol. 2:2.
18. Stabel, J. R., M. V. Palmer, B. Harris, B. Plattner, J. Hostetter, and S. Robbe-Austerman. 2009. Pathogenesis of *Mycobacterium avium* subsp. *paratuberculosis* in neonatal calves after oral or intraperitoneal experimental infection. Vet. Microbiol. 136:306-313.
19. Wu, C. W., M. Livesey, S. K. Schmoller, E. J. Manning, H. Steinberg, W. C. Davis, M. J. Hamilton, and A. M. Talaat. 2007. Invasion and persistence of *Mycobacterium avium* subsp. *paratuberculosis* during early stages of Johne's disease in calves. Infect. Immun. 75:2110-2119.
20. Shin, S. J., C.-W. Wu, H. Steinberg, and A. M. Talaat. 2006. Identification of Novel Virulence Determinants in *Mycobacterium paratuberculosis* by Screening a Library of Insertional Mutants. Infec. Immun. 7:3825-3833.
21. Alonso-Hearn, M., D. Patel, L. Danelishvili, L. Meunier-Goddik, and L. E. Bermudez. 2008. The *Mycobacterium avium* subsp. *paratuberculosis* MAP3464 gene encodes an oxidoreductase involved in invasion of bovine epithelial cells through the activation of host cell Cdc42. Infect. Immun. 76:170-178.
22. Wu, C. W., S. K. Schmoller, J. P. Bannantine, T. M. Eckstein, J. M. Inamine, M. Livesey, R. Albrecht, and A. M. Talaat. 2009. A novel cell wall lipopeptide is important for biofilm formation and pathogenicity of *Mycobacterium avium* subspecies *paratuberculosis*. Microb. Pathog. 46:222-230.
23. Alonso-Hearn, M., T. M. Eckstein, S. Sommer, and L. E. Bermudez. 2010. A *Mycobacterium avium* subsp. *paratuberculosis* LuxR regulates cell envelope and virulence. Innate immunity 16:235-247.
24. Zhu, X., Z. J. Tu, P. M. Coussens, V. Kapur, H. Janagama, S. Naser, and S. Sreevatsan. 2008. Transcriptional analysis of diverse strains *Mycobacterium avium* subspecies *paratuberculosis* in primary bovine monocyte derived macrophages. Microbes Infect. 10:1274-1282.
25. Janagama, H. K., E. A. Lamont, S. George, J. P. Bannantine, W. W. Xu, Z. J. Tu, S. J. Wells, J. Schefers, and S. Sreevatsan. 2010. Primary transcriptomes of *Mycobacterium avium* subsp. *paratuberculosis* reveal proprietary pathways in tissue and macrophages. BMC Genomics 11:561.
26. Manganelli, R., M. I. Voskuil, G. K. Schoolnik, E. Dubnau, M. Gomez, and I. Smith. 2002. Role of the extracytoplasmic-function sigma Factor sigma(H) in *Mycobacterium tuberculosis* global gene expression. Mol. Microbiol. 45:365-374.
27. Paget, M. S., J. G. Kang, J. H. Roe, and M. J. Buttner. 1998. sigmaR, an RNA polymerase sigma factor that modulates expression of the thioredoxin system in response to oxidative stress in *Streptomyces coelicolor* A3(2). EMBO J. 17:5776-5782. doi:10.1093/emboj/17.19.5776 [doi].

REFERENCES CITED IN EXAMPLE 1

1. Ghosh, P., C. Hsu, E. J. Alyamani, M. M. Shehata, M. A. Al-Dubaib, A. Al-Naeem, M. Hashad, O. M. Mahmoud, K. B. Alharbi, K. Al-Busadah, A. M. Al-Swailem, and A. M. Talaat. 2012. Genome-wide analysis of the emerging infection with *Mycobacterium avium* subspecies *paratuberculosis* in the Arabian camels (*Camelus dromedarius*). PLoS. One. 7:e31947.
2. Yalo Ayele, W., M. Machackova, and I. Pavlik. 2001. The transmission and impact of *paratuberculosis* infection in domestic and wild ruminants. Vet. Med. 46:205-224.
3. Nielsen, S. r. S. and N. Toft. 2009. A review of prevalences of *paratuberculosis* in farmed animals in Europe. Preventive Veterinary Medicine 88:1-14.
4. Lombard, J. E. 2011. Epidemiology and economics of *paratuberculosis*. Vet. Clin. North Am. Food Anim Pract. 27:525-35.
5. Lombard, J. E., I. A. Gardner, S. R. Jafarzadeh, C. P. Fossler, B. Harris, R. T. Capsel, B. A. Wagner, and W. O. Johnson. 2013. Herd-level prevalence of *Mycobacterium avium* subsp. *paratuberculosis* infection in United States dairy herds in 2007. Prev. Vet. Med. 108:234-238.
6. Ott, S. L., S. J. Wells, and B. A. Wagner. 1999. Herd-level economic losses associated with Johne's disease on US dairy operations. Prev. Vet. Med. 40:179-192.
7. Bermudez, L. E., M. Petrofsky, S. Sommer, and R. G. Barletta. 2010. Peyer's patch-deficient mice demonstrate that *Mycobacterium avium* subsp. *paratuberculosis* translocates across the mucosal barrier via both M cells and enterocytes but has inefficient dissemination. Infect. Immun. 78:3570-3577.
8. Chacon, O., L. E. Bermudez, and R. G. Barletta. 2004. Johne's disease, inflammatory bowel disease, and *Mycobacterium paratuberculosis*. Annu. Rev. Microbiol. 58:329-363.

9. Coussens, P. M., C. J. Colvin, K. Wiersma, A. Abouzied, and S. Sipkovsky. 2002. Gene expression profiling of peripheral blood mononuclear cells from cattle infected with *Mycobacterium paratuberculosis*. Infect. Immun. 70:5494-5502.
10. Coussens, P. M., A. Jeffers, and C. Colvin. 2004. Rapid and transient activation of gene expression in peripheral blood mononuclear cells from Johne's disease positive cows exposed to *Mycobacterium paratuberculosis* in vitro. Microbial. pathogenesis. 36:93-108.
11. Weiss, D. J., O. A. Evanson, M. Deng, and M. S. Abrahamsen. 2004. Gene expression and antimicrobial activity of bovine macrophages in response to *Mycobacterium avium* subsp. *paratuberculosis*. Vet. Pathol. 41:326-337.
12. Wu, C. W., S. K. Schmoller, S. J. Shin, and A. M. Talaat. 2007. Defining the stressome of *Mycobacterium avium* subsp *paratuberculosis* in vitro and in naturally infected cows. Journal of Bacteriology 189:7877-7886.
13. Whittington, R. J., D. J. Marshall, P. J. Nicholls, I. B. Marsh, and L. A. Reddacliff. 2004. Survival and dormancy of *Mycobacterium avium* subsp. *paratuberculosis* in the environment. Appl. Environ. Microbiol. 70:2989-3004.
14. Bannantine, J. P. and J. R. Stabel. 2002. Killing of *Mycobacterium avium* subspecies *paratuberculosis* within macrophages. BMC Microbiol. 2:2.
15. Stabel, J. R., M. V. Palmer, B. Harris, B. Plattner, J. Hostetter, and S. Robbe-Austerman. 2009. Pathogenesis of *Mycobacterium avium* subsp. *paratuberculosis* in neonatal calves after oral or intraperitoneal experimental infection. Vet. Microbiol. 136:306-313.
16. Wu, C. W., M. Livesey, S. K. Schmoller, E. J. Manning, H. Steinberg, W. C. Davis, M. J. Hamilton, and A. M. Talaat. 2007. Invasion and persistence of *Mycobacterium avium* subsp. *paratuberculosis* during early stages of Johne's disease in calves. Infect. Immun. 75:2110-2119.
17. Shin, S. J., C.-W. Wu, H. Steinberg, and A. M. Talaat. 2006. Identification of Novel Virulence Determinants in *Mycobacterium paratuberculosis* by Screening a Library of Insertional Mutants. Infec. Immun. 7:3825-3833.
18. Alonso-Hearn, M., D. Patel, L. Danelishvili, L. Meunier-Goddik, and L. E. Bermudez. 2008. The *Mycobacterium avium* subsp. *paratuberculosis* MAP3464 gene encodes an oxidoreductase involved in invasion of bovine epithelial cells through the activation of host cell Cdc42. Infect. Immun. 76:170-178.
19. Wu, C. W., S. K. Schmoller, J. P. Bannantine, T. M. Eckstein, J. M. Inamine, M. Livesey, R. Albrecht, and A. M. Talaat. 2009. A novel cell wall lipopeptide is important for biofilm formation and pathogenicity of *Mycobacterium avium* subspecies *paratuberculosis*. Microb. Pathog. 46:222-230.
20. Alonso-Hearn, M., T. M. Eckstein, S. Sommer, and L. E. Bermudez. 2010. A *Mycobacterium avium* subsp. *paratuberculosis* LuxR regulates cell envelope and virulence. Innate immunity 16:235-247.
21. Zhu, X., Z. J. Tu, P. M. Coussens, V. Kapur, H. Janagama, S. Naser, and S. Sreevatsan. 2008. Transcriptional analysis of diverse strains *Mycobacterium avium* subspecies *paratuberculosis* in primary bovine monocyte derived macrophages. Microbes. Infect. 10:1274-1282.
22. Janagama, H. K., E. A. Lamont, S. George, J. P. Bannantine, W. W. Xu, Z. J. Tu, S. J. Wells, J. Schefers, and S. Sreevatsan. 2010. Primary transcriptomes of *Mycobacterium avium* subspecies *paratuberculosis* reveal proprietary pathways in tissue and macrophages. BMC Genomics. 11:561.:561.
23. Arsenault, R. J., Y. Li, K. Bell, K. Doig, A. Potter, P. J. Griebel, A. Kusalik, and S. Napper. 2012. *Mycobacterium avium* subspecies *paratuberculosis* Inhibits Gamma Interferon-Induced Signaling in Bovine Monocytes: Insights into the Cellular Mechanisms of Johne's Disease. Infect.& Immun. 80:3039-3048.
24. Sechi, L. A., G. E. Felis, N. Ahmed, D. Paccagnini, D. Usai, S. Ortu, P. Molicotti, and S. Zanetti. 2007. Genome and transcriptome scale portrait of sigma factors in *Mycobacterium avium* subsp. *paratuberculosis*. Infection, Genetics and Evolution 7:424-432.
25. Raman, S., T. Song, X. Puyang, S. Bardarov, W. R. Jacobs, Jr., and R. N. Husson. 2001. The Alternative Sigma Factor SigH Regulates Major Components of Oxidative and Heat Stress Responses in *Mycobacterium tuberculosis*. The Journal of Bacteriology 183:6119-6125.
26. Diwu, Z., C. S. Chen, C. Zhang, D. H. Klaubert, and R. P. Haugland. 1999. A novel acidotropic pH indicator and its potential application in labeling acidic organelles of live cells. Chemistry & biology 6:411-418.
27. Wozniak, A. L., S. Griffin, D. Rowlands, M. Harris, M. Yi, S. M. Lemon, and S. A. Weinman. 2010. Intracellular proton conductance of the hepatitis C virus p7 protein and its contribution to infectious virus production. PLoS Pathog. 6:e1001087.
28. Abramoff, M. D., P. J. Magelhaes, and S. J. Ram. 2004. Image Processing with ImageJ. Biophotonics International 11:36-42.
29. Grode, L., P. Seiler, S. Baumann, J. Hess, V. Brinkmann, E. A. Nasser, P. Mann, C. Goosmann, S. Bandermann, D. Smith, G. J. Bancroft, J. M. Reyrat, S. D. van, B. Raupach, and S. H. Kaufmann. 2005. Increased vaccine efficacy against tuberculosis of recombinant *Mycobacterium bovis* bacille Calmette-Guerin mutants that secrete listeriolysin. The Journal of clinical investigation 115:2472-2479.
30. Rohde, K. H., R. B. Abramovitch, and D. G. Russell. 2007. *Mycobacterium tuberculosis* invasion of macrophages: linking bacterial gene expression to environmental cues. Cell Host Microbe 2:352-364.
31. Talaat, A. M., S. T. Howard, W. Hale, R. Lyons, H. Garner, and S. A. Johnston. 2002. Genomic DNA standards for gene expression profiling in *Mycobacterium tuberculosis*. Nucleic Acids Res. 30:e104.
32. Li, L., J. P. Bannantine, Q. Zhang, A. Amonsin, B. J. May, D. Alt, N. Banerji, S. Kanjilal, and V. Kapur. 2005. The complete genome sequence of *Mycobacterium avium* subspecies *paratuberculosis*. Proc. Natl. Acad. Sci U.S.A. 102:12344-12349.
33. Talaat, A. M., P. Hunter, and S. A. Johnston. 2000. Genome-directed primers for selective labeling of bacterial transcripts for DNA microarray analysis. Nat. Biotechnol. 18:679-682.
34. Raychaudhuri, S., J. M. Stuart, and R. B. Altman. 2000. Principal components analysis to summarize microarray experiments: application to sporulation time series. Pac. Symp. Biocomput. 455-466.
35. Wynne, J. W., T. Seemann, D. M. Bulach, S. A. Coutts, A. M. Talaat, and W. P. Michalski. 2010. Resequencing the *Mycobacterium avium* subsp. *paratuberculosis* K10 genome: improved annotation and revised genome sequence. J. Bacteriol. 192:6319-6320.

36. Mortazavi, A., B. A. Williams, K. McCue, L. Schaeffer, and B. Wold. 2008. Mapping and quantifying mammalian transcriptomes by RNA-Seq. Nat. Methods 5:621-628.
37. Kal, A. J., A. J. van Zonneveld, V. Benes, M. van den Berg, M. G. Koerkamp, K. Albermann, N. Strack, J. M. Ruijter, A. Richter, B. Dujon, W. Ansorge, and H. F. Tabak. 1999. Dynamics of gene expression revealed by comparison of serial analysis of gene expression transcript profiles from yeast grown on two different carbon sources. Mol. Biol. Cell 10:1859-1872.
38. Edgar, R., M. Domrachev, and A. E. Lash. 2002. Gene Expression Omnibus: NCBI gene expression and hybridization array data repository. Nucleic Acids Res. 30:207-210.
39. Ward, S. K., E. A. Hoye, and A. M. Talaat. 2008. The global responses of *Mycobacterium tuberculosis* to physiological levels of copper. J. Bacteriol. 190:2939-2946.
40. Talaat, A. M., S. K. Ward, C.-W. Wu, E. Rondon, C. Tavano, J. P. Bannantine, R. Lyons, and S. A. Johnston. 2007. Mycobacterial bacilli are metabolically active during chronic tuberculosis in murine lungs: Insights from genome-wide transcriptional profiling. J. Bacteriol. 189:4265-4274.
41. Pfaffl, M. W. 2001. A new mathematical model for relative quantification in real-time RT-PCR. Nucleic Acids Res. 29:e45.
42. Bannantine, J. P. and A. M. Talaat. 2010. Genomic and transcriptomic studies in *Mycobacterium avium* subspecies *paratuberculosis*. Vet. Immunol. Immunopathol. 138:303-311.
43. Janagama, H. K., T. M. Senthilkumar, J. P. Bannantine, G. M. Rodriguez, I. Smith, M. L. Paustian, J. A. McGarvey, and S. Sreevatsan. 2009. Identification and functional characterization of the iron-dependent regulator (IdeR) of *Mycobacterium avium* subsp. *paratuberculosis*. Microbiology 155:3683-3690.
44. Schnappinger, D., S. Ehrt, M. I. Voskuil, Y. Liu, J. A. Mangan, I. M. Monahan, G. Dolganov, B. Efron, P. D. Butcher, C. Nathan, and G. K. Schoolnik. 2003. Transcriptional Adaptation of *Mycobacterium tuberculosis* within Macrophages: Insights into the Phagosomal Environment. J. Exp. Med. 198:693-704.
45. Pagan-Ramos, E., S. S. Master, C. L. Pritchett, R. Reimschuessel, M. Trucksis, G. S. Timmins, and V. Deretic. 2006. Molecular and physiological effects of mycobacterial oxyR inactivation. J. Bacteriol. 188:2674-2680.
46. den Hengst, C. D. and M. J. Buttner. 2008. Redox control in actinobacteria. Biochim. Biophys. Acta 1780:1201-1216.
47. Bashyam, M. D. and S. E. Hasnain. 2004. The extracytoplasmic function sigma factors: role in bacterial pathogenesis. Infect. Genet. Evol. 4:301-308.
48. Sachdeva, P., R. Misra, A. K. Tyagi, and Y. Singh. 2010. The sigma factors of *Mycobacterium tuberculosis*: regulation of the regulators. Febs Journal 277:605-626.
49. Kazmierczak, M. J., M. Wiedmann, and K. J. Boor. 2005. Alternative sigma factors and their roles in bacterial virulence. Microbiol. Mol. Biol. Rev. 69:527-543.
50. Dubnau, E., P. Fontan, R. Manganelli, S. Soares-Appel, and I. Smith. 2002. *Mycobacterium tuberculosis* genes induced during infection of human macrophages. Infect. Immun. 70:2787-2795.
51. Manganelli, R., R. Provvedi, S. Rodrigue, J. Beaucher, L. Gaudreau, and I. Smith. 2004. Sigma factors and global gene regulation in *Mycobacterium tuberculosis*. J. Bacteriol. 186:895-902.
52. Graham, J. E. and J. E. Clark-Curtiss. 1999. Identification of *Mycobacterium tuberculosis* RNAs synthesized in response to phagocytosis by human macrophages by selective capture of transcribed sequences (SCOTS). Proc. Natl. Acad. Sci. U.S.A. 96:11554-11559.
53. Bardarov, S., Bardarov Jr S Jr, J. M. Pavelka, Jr., V. Sambandamurthy, M. Larsen, J. Tufariello, J. Chan, G. Hatfull, and J. W. Jacobs, Jr. 2002. Specialized transduction: an efficient method for generating marked and unmarked targeted gene disruptions in *Mycobacterium tuberculosis, M. bovis* BCG and *M. smegmatis*. Microbiology 148:3007-3017.
54. Song, T. S., S. L. Dove, K. H. Lee, and R. N. Husson. 2003. RshA, an anti-sigma factor that regulates the activity of the mycobacterial stress response sigma factor SigH. Molecular Microbiology 50:949-959.
55. Karls, R. K., J. Guarner, D. N. McMurray, K. A. Birkness, and F. D. Quinn. 2006. Examination of *Mycobacterium tuberculosis* sigma factor mutants using low-dose aerosol infection of guinea pigs suggests a role for SigC in pathogenesis. Microbiology 152:1591-1600.
56. Raman, S., R. Hazra, C. C. Dascher, and R. N. Husson. 2004. Transcription regulation by the *Mycobacterium tuberculosis* alternative sigma factor SigD and its role in virulence. Journal of Bacteriology 186:6605-6616.
57. Kaushal, D., B. G. Schroeder, S. Tyagi, T. Yoshimatsu, C. Scott, C. Ko, L. Carpenter, J. Mehrotra, Y. C. Manabe, R. D. Fleischmann, and W. R. Bishai. 2002. Reduced immunopathology and mortality despite tissue persistence in a *Mycobacterium tuberculosis* mutant lacking alternative sigma factor, SigH. Proceedings of the National Academy of Sciences of the United States of America 99:8330-8335.
58. Echave, P., J. Tamarit, E. Cabiscol, and J. Ros. 2003. Novel antioxidant role of alcohol dehydrogenase E from *Escherichia coli*. J. Biol. Chem. 278:30193-30198.
59. Manganelli, R., M. I. Voskuil, G. K. Schoolnik, E. Dubnau, M. Gomez, and I. Smith. 2002. Role of the extracytoplasmic-function sigma Factor sigma(H) in *Mycobacterium tuberculosis* global gene expression. Mol. Microbiol. 45:365-374.
60. Singh, A., D. K. Crossman, D. Mai, L. Guidry, M. I. Voskuil, M. B. Renfrow, and A. J. Steyn. 2009. *Mycobacterium tuberculosis* WhiB3 maintains redox homeostasis by regulating virulence lipid anabolism to modulate macrophage response. PLoS. Pathog. 5:e1000545.
61. Cangelosi, G. A., J. S. Do, R. Freeman, J. G. Bennett, M. Semret, and M. A. Behr. 2006. The two-component regulatory system mtrAB is required for morphotypic multidrug resistance in *Mycobacterium avium*. Antimicrob. Agents Chemother. 50:461-468.
62. Zahrt, T. C. and V. Deretic. 2000. An essential two-component signal transduction system in *Mycobacterium tuberculosis*. J. Bacteriol. 182:3832-3838.
63. Mehra, S. and D. Kaushal. 2009. Functional genomics reveals extended roles of the *Mycobacterium tuberculosis* stress response factor sigmaH. J. Bacteriol. 191:3965-3980.
64. Busche, T., R. Silar, M. Picmanova, M. Patek, and J. Kalinowski. 2012. Transcriptional regulation of the operon encoding stress-responsive ECF sigma factor SigH and its anti-sigma factor RshA, and control of its regulatory network in *Corynebacterium glutamicum*. BMC. Genomics 13:445.
65. Paget, M. S., J. G. Kang, J. H. Roe, and M. J. Buttner. 1998. sigmaR, an RNA polymerase sigma factor that modulates expression of the thioredoxin system in response to oxidative stress in *Streptomyces coelicolor* A3(2). EMBO J. 17:5776-5782.
66. Kuehnel, M. P., R. Goethe, A. Habermann, E. Mueller, M. Rohde, G. Griffiths, and P. Valentin-Weigand. 2001. Characterization of the intracellular survival of *Mycobacterium avium* ssp. *paratuberculosis*: phagosomal pH and fusogenicity in J774 macrophages compared with other mycobacteria. Cell Microbiol. 3:551-566.
67. Stewart, G. R., L. Wernisch, R. Stabler, J. A. Mangan, J. Hinds, K. G. Laing, D. B. Young, and P. D. Butcher. 2002. Dissection of the heat-shock response in *Mycobacterium tuberculosis* using mutants and microarrays. Microbiology 148:3129-3138.
68. Yang, H., S. Huang, H. Dai, Y. Gong, C. Zheng, and Z. Chang. 1999. The *Mycobacterium tuberculosis* small heat shock protein Hsp16.3 exposes hydrophobic surfaces at mild conditions: conformational flexibility and molecular chaperone activity. Protein Sci. 8:174-179.
69. Zhao, B., M. T. Collins, and C. J. Czuprynski. 1997. Effects of gamma interferon and nitric oxide on the interaction of *Mycobacterium avium* subsp. *paratuberculosis* with bovine monocytes. Infect. Immun. 65:1761-1766.
70. Basler, T., C. Brumshagen, A. Beineke, R. Goethe, and W. Baumer. 2013. *Mycobacterium avium* subspecies impair dendritic cell maturation. Innate. Immun. (Epub ahead of print).
71. Kabara, E. and P. M. Coussens. 2012. Infection of Primary Bovine Macrophages with *Mycobacterium avium* Subspecies *paratuberculosis* Suppresses Host Cell Apoptosis. Front Microbiol. 3:215.
72. Mehra, S., N. A. Golden, K. Stuckey, P. J. Didier, L. A. Doyle, K. E. Russell-Lodrigue, C. Sugimoto, A. Hasegawa, S. K. Sivasubramani, C. J. Roy, X. Alvarez, M. J. Kuroda, J. L. Blanchard, A. A. Lackner, and D. Kaushal. 2012. The *Mycobacterium tuberculosis* stress response factor SigH is required for bacterial burden as well as immunopathology in primate lungs. J. Infect. Dis. 205:1203-1213.

REFERENCES CITED IN EXAMPLE 2

1. Nielsen, S. r. S. and N. Toft. 2009. A review of prevalences of *paratuberculosis* in farmed animals in Europe. Preventive Veterinary Medicine 88:1-14. doi:doi: DOI: 10.1016/j.prevetmed.2008.07.003.
2. Ghosh, P., C. Hsu, E. J. Alyamani, M. M. Shehata, M. A. Al-Dubaib, A. Al-Naeem, M. Hashad, O. M. Mahmoud, K. B. Alharbi, K. Al-Busadah, A. M. Al-Swailem, and A. M. Talaat. 2012. Genome-wide analysis of the emerging infection with *Mycobacterium avium* subspecies *paratuberculosis* in the Arabian camels (*Camelus dromedarius*). PLoS. One. 7:e31947.
3. Kumthekar, S., E. J. Manning, P. Ghosh, K. Tiwari, R. N. Sharma, and H. Hariharan. 2013. *Mycobacterium avium* subspecies *paratuberculosis* confirmed following serological surveillance of small ruminants in Grenada, West Indies. J. Vet. Diagn. Invest 25:527-530. doi: 1040638713490688 [pii]; 10.1177/1040638713490688 [doi].
4. McClure, H. M., R. J. Chiodini, D. C. Anderson, R. B. Swenson, W. R. Thayer, and J. A. Coutu. 1987. *Mycobacterium paratuberculosis* infection in a colony of stumptail macaques (*Macaca arctoides*). J. Infect. Dis. 155:1011-1019.
5. Eltholth, M. M., V. R. Marsh, W. S. Van, and F. J. Guitian. 2009. Contamination of food products with *Mycobacterium avium paratuberculosis*: a systematic review. J. Appl. Microbiol. 107:1061-1071. doi:JAM4286 [pii]; 10.1111/j.1365-2672.2009.04286.x [doi].
6. Golan, L., A. Livneh-Kol, E. Gonen, S. Yagel, I. Rosenshine, and N. Y. Shpigel. 2009. *Mycobacterium avium paratuberculosis* invades human small-intestinal goblet cells and elicits inflammation. J. Infect. Dis. 199:350-354. doi:10.1086/596033 [doi].
7. Naser, S. A., G. Ghobrial, C. Romero, and J. F. Valentine. 2004. Culture of *Mycobacterium avium* subspecies *paratuberculosis* from the blood of patients with Crohn's disease. Lancet 364:1039-1044.
8. Bull, T. J., E. J. McMinn, K. Sidi-Boumedine, A. Skull, D. Durkin, P. Neild, G. Rhodes, R. Pickup, and J. Hermon-Taylor. 2003. Detection and verification of *Mycobacterium avium* subsp. *paratuberculosis* in fresh ileocolonic mucosal biopsy specimens from individuals with and without Crohn's disease. J. Clin. Microbiol. 41:2915-2923.
9. Naser, S. A., S. Thanigachalam, C. T. Dow, and M. T. Collins. 2013. Exploring the role of *Mycobacterium avium* subspecies *paratuberculosis* in the pathogenesis of type 1 diabetes mellitus: a pilot study. Gut Pathog. 5:14. doi:1757-4749-5-14 [pii]; 10.1186/1757-4749-5-14 [doi].
10. Masala, S., D. Paccagnini, D. Cossu, V. Brezar, A. Pacifico, N. Ahmed, R. Mallone, and L. A. Sechi. 2011. Antibodies recognizing *Mycobacterium avium paratuberculosis* epitopes cross-react with the beta-cell antigen ZnT8 in Sardinian type 1 diabetic patients. PLoS. One. 6:e26931. doi:10.1371/journal.pone.0026931 [doi]; PONE-D-11-14979 [pii].
11. Lombard, J. E., I. A. Gardner, S. R. Jafarzadeh, C. P. Fossler, B. Harris, R. T. Capsel, B. A. Wagner, and W. O. Johnson. 2013. Herd-level prevalence of *Mycobacterium avium* subsp. *paratuberculosis* infection in United States dairy herds in 2007. Prev. Vet. Med. 108:234-238. doi: S0167-5877(12)00267-X [pii]; 10.1016/j.prevetmed.2012.08.006 [doi].
12. Hermon-Taylor, J. 2009. *Mycobacterium avium* subspecies *paratuberculosis*, Crohn's disease and the Doomsday scenario. Gut Pathog. 1:15. doi:1757-4749-1-15 [pii]; 10.1186/1757-4749-1-15 [doi].
13. Lei, L., B. L. Plattner, and J. M. Hostetter. 2008. Live *Mycobacterium avium* subsp. *paratuberculosis* and a killed-bacterium vaccine induce distinct subcutaneous granulomas, with unique cellular and cytokine profiles. Clin. Vaccine Immunol. 15:783-793. doi:CVI.00480-07 [pii]; 10.1128/CVI.00480-07 [doi].
14. Losinger, W. C. 2005. Economic impact of reduced milk production associated with Johne's disease on dairy operations in the USA. Journal of Dairy Research 72:425-432.
15. Uzonna, J. E., P. Chilton, R. H. Whitlock, P. L. Habecker, P. Scott, and R. W. Sweeney. 2003. Efficacy of commercial and field-strain *Mycobacterium paratuberculosis* vaccinations with recombinant IL-12 in a bovine experimental infection model. Vaccine 21:3101-3109. doi: S0264410X03002615 [pii].
16. Kalis, C. H., J. W. Hesselink, H. W. Barkema, and M. T. Collins. 2001. Use of long-term vaccination with a killed vaccine to prevent fecal shedding of *Mycobacterium avium* subsp *paratuberculosis* in dairy herds. Am. J. Vet. Res. 62:270-274.
17. Patterson, C. J., M. LaVenture, S. S. Hurley, and J. P. Davis. 1988. Accidental self-inoculation with *Mycobac-* terium paratuberculosis bacterin (Johne's bacterin) by veterinarians in Wisconsin. J. Am. Vet. Med. Assoc. 192:1197-1199.

18. Cossu, A., L. A. Sechi, S. Zanetti, and V. Rosu. 2012. Gene expression profiling of *Mycobacterium avium* subsp. *paratuberculosis* in simulated multi-stress conditions and within THP-1 cells reveals a new kind of interactive intramacrophage behaviour. BMC. Microbiol. 12:87. doi:1471-2180-12-87 [pii]; 10.1186/1471-2180-12-87 [doi].

19. Ghosh, P., C. W. Wu, and A. M. Talaat. 2013. Key Role for the Alternative Sigma Factor, SigH, in the Intracellular Life of *Mycobacterium avium* subsp. *paratuberculosis* during Macrophage Stress. Infect. Immun. 81:2242-2257.

20. Li, L., J. P. Bannantine, Q. Zhang, A. Amonsin, B. J. May, D. Alt, N. Banerji, S. Kanjilal, and V. Kapur. 2005. The complete genome sequence of *Mycobacterium avium* subspecies *paratuberculosis*. Proc. Natl. Acad. Sci U.S.A. 102:12344-12349.

21. Janagama, H. K., E. A. Lamont, S. George, J. P. Bannantine, W. W. Xu, Z. J. Tu, S. J. Wells, J. Schefers, and S. Sreevatsan. 2010. Primary transcriptomes of *Mycobacterium avium* subsp. *paratuberculosis* reveal proprietary pathways in tissue and macrophages. BMC Genomics 11:561.

22. Schnappinger, D., S. Ehrt, M. I. Voskuil, Y. Liu, J. A. Mangan, I. M. Monahan, G. Dolganov, B. Efron, P. D. Butcher, C. Nathan, and G. K. Schoolnik. 2003. Transcriptional Adaptation of *Mycobacterium tuberculosis* within Macrophages: Insights into the Phagosomal Environment. J. Exp. Med. 198:693-704. doi:10.1084/jem.20030846 [doi]; jem.20030846 [pii].

23. Cole, S. T., R. Brosch, J. Parkhill, T. Gamier, C. Churcher, D. Harris, S. V. Gordon, K. Eiglmeier, S. Gas, C. E. Barry, III, F. Tekaia, K. Badcock, D. Basham, D. Brown, T. Chillingworth, R. Connor, R. Davies, K. Devlin, T. Feltwell, S. Gentles, N. Hamlin, S. Holroyd, T. Hornsby, K. Jagels, A. Krogh, J. McLean, S. Moule, L. Murphy, K. Oliver, J. Osborne, M. A. Quail, M. A. Rajandream, J. Rogers, S. Rutter, K. Seeger, J. Skelton, R. Squares, S. Squares, J. E. Sulston, K. Taylor, S. Whitehead, and B. G. Barrell. 1998. Deciphering the biology of *Mycobacterium tuberculosis* from the complete genome sequence. Nature 393:537-544. doi:10.1038/31159 [doi].

24. Hahn, M. Y., S. Raman, M. Anaya, and R. N. Husson. 2005. The *Mycobacterium tuberculosis* extracytoplasmic-function sigma factor SigL regulates polyketide synthases and secreted or membrane proteins and is required for virulence. Journal of Bacteriology 187:7062-7071.

25. Pelicic, V., M. Jackson, J. M. Reyrat, W. R. Jacobs, Jr., B. Gicquel, and C. Guilhot. 1997. Efficient allelic exchange and transposon mutagenesis in *Mycobacterium tuberculosis*. Proc. Natl. Acad. Sci. U.S.A. 94:10955-10960.

26. Ward, S. K., B. Abomoelak, E. A. Hoye, H. Steinberg, and A. M. Talaat. 2010. CtpV: a putative copper exporter required for full virulence of *Mycobacterium tuberculosis*. Mol. Microbiol. 77:1096-1110. doi:MMI7273 [pii]; 10.1111/j.1365-2958.2010.07273.x [doi].

27. Kaushal, D., B. G. Schroeder, S. Tyagi, T. Yoshimatsu, C. Scott, C. Ko, L. Carpenter, J. Mehrotra, Y. C. Manabe, R. D. Fleischmann, and W. R. Bishai. 2002. Reduced immunopathology and mortality despite tissue persistence in a *Mycobacterium tuberculosis* mutant lacking alternative sigma factor, SigH. Proc. Natl. Acad. Sci U.S.A. 99:8330-8335.

28. Murali-Krishna, K., J. D. Altman, M. Suresh, D. J. Sourdive, A. J. Zajac, J. D. Miller, J. Slansky, and R. Ahmed. 1998. Counting antigen-specific CD8 T cells: a reevaluation of bystander activation during viral infection. Immunity. 8:177-187. doi:S1074-7613(00)80470-7 [pii].

29. Frey, A., C. J. Di, and D. Zurakowski. 1998. A statistically defined endpoint titer determination method for immunoassays. J. Immunol. Methods 221:35-41. doi: S0022-1759(98)00170-7 [pii].

30. Gilliland, S. E., T. E. Staley, and L. J. Bush. 1984. Importance of bile tolerance of *Lactobacillus acidophilus* used as a dietary adjunct. J. Dairy Sci. 67:3045-3051. doi:S0022-0302(84)81670-7 [pii]; 10.3168/jds.S0022-0302(84)81670-7 [doi].

31. Sung, N. and M. T. Collins. 2003. Variation in resistance of *Mycobacterium paratuberculosis* to acid environments as a function of culture medium. Appl. Environ. Microbiol. 69:6833-6840.

32. Dainese, E., S. Rodrigue, G. Delogu, R. Provvedi, L. Laflamme, R. Brzezinski, G. Fadda, I. Smith, L. Gaudreau, G. Palu, and R. Manganelli. 2006. Posttranslational regulation of *Mycobacterium tuberculosis* extracytoplasmic-function sigma factor sigma(L) and roles in virulence and in global regulation of gene expression. Infect. Immun. 74:2457-2461.

33. Khader, S. A. and R. Gopal. 2010. IL-17 in protective immunity to intracellular pathogens. Virulence. 1:423-427. doi:12862 [pii]; 10.4161/viru.1.5.12862 [doi].

34. Shin, S. J., C.-W. Wu, H. Steinberg, and A. M. Talaat. 2006. Identification of Novel Virulence Determinants in *Mycobacterium paratuberculosis* by Screening a Library of Insertional Mutants. Infec. Immun. 7:3825-3833.

35. Begg, D. J. and J. F. Griffin. 2005. Vaccination of sheep against *M. paratuberculosis*: immune parameters and protective efficacy. Vaccine 23:4999-5008. doi:S0264-410X(05)00563-3 [pii]; 10.1016/j.vaccine.2005.05.031 [doi].

36. Stabel, J. R. and S. Robbe-Austerman. 2011. Early immune markers associated with *Mycobacterium avium* subsp. *paratuberculosis* infection in a neonatal calf model. Clin. Vaccine Immunol. 18:393-405. doi: CVI.00359-10 [pii]; 10.1128/CVI.00359-10 [doi].

37. Wu, C. W., S. K. Schmoller, S. J. Shin, and A. M. Talaat. 2007. Defining the stressome of *Mycobacterium avium* subsp *paratuberculosis* in vitro and in naturally infected cows. Journal of Bacteriology 189:7877-7886.

38. Gunn, J. S. 2000. Mechanisms of bacterial resistance and response to bile. Microbes. Infect. 2:907-913. doi:S1286-4579(00)00392-0 [pii].

39. Prieto, A. I., F. Ramos-Morales, and J. Casadesus. 2006. Repair of DNA damage induced by bile salts in *Salmonella enterica*. Genetics 174:575-584. doi:genetics.106.060889 [pii]; 10.1534/genetics.106.060889 [doi].

40. den Hengst, C. D. and M. J. Buttner. 2008. Redox control in actinobacteria. Biochim. Biophys. Acta. 1780:1201-1216. doi:S0304-4165(08)00009-3 [pii]; 10.1016/j.bbagen.2008.01.008 [doi].

41. Coynault, C., V. Robbe-Saule, and F. Norel. 1996. Virulence and vaccine potential of *Salmonella typhimurium* mutants deficient in the expression of the RpoS (sigma S) regulon. Mol. Microbiol. 22:149-160.

42. Hernandez, P. R., L. D. Aguilar, I. Smith, and R. Manganelli. 2010. Immunogenicity and protection induced by a *Mycobacterium tuberculosis* sigE mutant in a BALB/c mouse model of progressive pulmonary tuberculosis. Infect. Immun. 78:3168-3176. doi:IAI.00023-10 [pii]; 10.1128/IAI.00023-10 [doi].

43. Park, K. T., A. J. Allen, J. P. Bannantine, K. S. Seo, M. J. Hamilton, G. S. Abdellrazeq, H. M. Rihan, A. Grimm, and W. C. Davis. 2011. Evaluation of two mutants of Mycobacterium avium subsp. paratuberculosis as candidates for a live attenuated vaccine for Johne's disease. Vaccine 29:4709-4719. doi:S0264-410X(11)00645-1 [pii]; 10.1016/j.vaccine.2011.04.090 [doi].

44. Chen, J. W., S. M. Faisal, S. Chandra, S. P. McDonough, M. A. Moreira, J. Scaria, C. F. Chang, J. P. Bannantine, B. Akey, and Y. F. Chang. 2012. Immunogenicity and protective efficacy of the Mycobacterium avium subsp. paratuberculosis attenuated mutants against challenge in a mouse model. Vaccine. 30:3015-3025. doi:S0264-410X(11)01798-1 [pii]; 10.1016/j.vaccine.2011.11.029 [doi].

45. O'Garra, A., P. S. Redford, F. W. McNab, C. I. Bloom, R. J. Wilkinson, and M. P. Berry. 2013. The immune response in tuberculosis. Annu. Rev. Immunol. 31:475-527. doi:10.1146/annurev-immunol-032712-095939 [doi].

46. Begg, D. J., S. K. de, N. Carter, K. M. Plain, A. Purdie, and R. J. Whittington. 2011. Does a Th1 over Th2 dominancy really exist in the early stages of Mycobacterium avium subspecies paratuberculosis infections? Immunobiology 216:840-846. doi:S0171-2985(10) 00220-2 [pii]; 10.1016/j.imbio.2010.12.004 [doi].

47. Scandurra, G. M., G. W. de Lisle, S. M. Cavaignac, M. Young, R. P. Kawakami, and D. M. Collins. 2010. Assessment of live candidate vaccines for paratuberculosis in animal models and macrophages. Infect. Immun. 78:1383-1389. doi:IAI.01020-09 [pii]; 10.1128/IAI.01020-09 [doi].

48. Jeyanathan, M., D. C. Alexander, C. Y. Turenne, C. Girard, and M. A. Behr. 2006. Evaluation of in situ methods used to detect Mycobacterium avium subsp. paratuberculosis in samples from patients with Crohn's disease. J. Clin. Microbiol. 44:2942-2950. doi:44/8/2942 [pii]; 10.1128/JCM.00585-06 [doi].

49. Seiler, P., T. Ulrichs, S. Bandermann, L. Pradl, S. Jorg, V. Krenn, L. Morawietz, S. H. Kaufmann, and P. Aichele. 2003. Cell-wall alterations as an attribute of Mycobacterium tuberculosis in latent infection. J. Infect. Dis. 188: 1326-1331. doi:JID30430 [pii]; 10.1086/378563 [doi].

I claim:

1. A *Mycobacterium* mutant, comprising a mutation in a gene sequence encoding global gene regulators (GGRs), wherein the GGR is sigE, wherein the GGR gene is at least partially inactivated, wherein the *Mycobacterium* is selected from the group consisting of *Mycobacterium avium* subspecies paratuberculosis (*M. ap*) and *Mycobacterium bovis* (*M. bovis*).

2. The mutant of claim 1, wherein the *Mycobacterium* is *M. ap*.

3. The mutant of claim 1, wherein the *Mycobacterium* is *M. bovis*.

4. The mutant of claim 1, further comprising a mutation in a gene sequence encoding a second GGR, wherein the GGR is *M. ap* sigH (SEQ ID NO:1) or a sequence substantially identical to SEQ ID NO:1.

5. The mutant of claim 1, further comprising a mutation in a gene sequence encoding a second GGR, wherein the GGR is *M. ap* sigL (SEQ ID NO:2) or a sequence substantially identical to SEQ ID NO:2.

6. The mutant of claim 1, further comprising a mutation in a gene sequence encoding a second GGR, wherein the GGR is *M. ap* ECF-1 (SEQ ID NO:4) or a sequence substantially identical to SEQ ID NO:4.

7. The mutant of claim 1, wherein the inactivation is achieved by at least partial deletion of the gene sequence encoding GGRs.

8. The mutant of claim 7, wherein the inactivation is achieved by a complete deletion of the gene sequence encoding GGRs.

9. The mutant of claim 1, wherein the inactivation is achieved by at least partial transposon insertion of the gene sequence encoding GGRs.

10. The mutant of claim 9, wherein the inactivation is achieved by a complete transposon insertion of the gene sequence encoding GGRs.

11. The mutant of claim 1, wherein the inactivation is achieved by at least partial anti-sense construct of the gene sequence encoding GGRs.

12. The mutant of claim 11, wherein the inactivation is achieved by a complete anti-sense construct of the gene sequence encoding GGRs.

13. An isolated mycobacterial organism comprising a *Mycobacterium* mutant according to claim 1.

14. A *Mycobacterium* vaccine comprising a *Mycobacterium* mutant according to claim 1.

15. The vaccine of claim 14, wherein the vaccine is physically inactivated.

16. The vaccine of claim 15, wherein the vaccine is heat inactivated.

17. The vaccine of claim 14, wherein the vaccine is chemically inactivated.

18. The vaccine of claim 17, wherein the vaccine is formaldehyde inactivated.

19. The vaccine of claim 14, wherein the vaccine is a live attenuated vaccine.

20. A *Mycobacterium* mutant, comprising a mutation in a gene sequence encoding global gene regulators (GGRs), wherein the GGR is sigH, wherein the GGR gene is at least partially inactivated, and wherein the *Mycobacterium* is *Mycobacterium avium* subspecies paratuberculosis (*M. ap*).

21. The mutant of claim 20, wherein the sigH comprises SEQ ID NO:1 or a sequence substantially identical to SEQ ID NO:1.

22. A *Mycobacterium* vaccine comprising a *Mycobacterium* mutant according to claim 20.

\* \* \* \* \*

UNITED STATES PATENT AND TRADEMARK OFFICE
CERTIFICATE OF CORRECTION

PATENT NO. : 11,655,447 B2
APPLICATION NO. : 17/221605
DATED : May 23, 2023
INVENTOR(S) : Adel M. Talaat Page 1 of 1

It is certified that error appears in the above-identified patent and that said Letters Patent is hereby corrected as shown below:

In the Specification

Column 7, Line 10, "*ap* a factors" should be --*ap* σ factors--.

Column 7, Line 16, "*ap* a factors" should be --*ap* σ factors--.

Column 7, Lines 50-51, "*avium avium*)" should be --*avium* (*M. avium*)--.

Column 18, Line 56, "PadI" should be --PacI--.

Column 18, Line 57, "PadI-digested" should be --PacI-digested--.

Column 21, Line 38, "(IVIES)" should be --(MES)--.

Column 25, Line 59, "The id gene" should be --The *icl* gene--.

Column 25, Line 64, "of id to" should be --of *icl* to--.

Column 49, Line 34, "Gamier" should be --Garnier--.

Signed and Sealed this
Seventeenth Day of October, 2023

Katherine Kelly Vidal
*Director of the United States Patent and Trademark Office*

SEQUENCE LISTING

<160> NUMBER OF SEQ ID NOS: 5

<210> SEQ ID NO 1
<211> LENGTH: 807
<212> TYPE: DNA
<213> ORGANISM: Mycobacterium avium

<400> SEQUENCE: 1

```
gtggtgtcaa cggcgacgag cctgttaggc gaggagcagt tggctggctt ccttgcgagt      60 ccggggcgc tttcggtgct ttccggtgac accgcagcag aagggaccgg gtttatcgaa      120
atggccgatt ctccagatgg cccagacggc gtgaccagcc cggaagtccc cgaagcgcac      180
gcagaaccgg cggcgcacga agaggcccgc gaagagaccg acgccgaatt gacggcgcgg      240
ttcgagcgcg acgcgattcc cctgctggac cagctgtacg gcggtgcgct gcggatgacg      300
cgcaatccgg ccgacgccga ggatttgctg caggaaacga tggtgaaggc ctacgcgggg      360
ttccgctcgt ttcgcgccgg caccaatctc aaggcgtggc tctaccgcat cctgaccaac      420
acctacatca acagctaccg caagaagcag cgccagcccg cggagtatcc gaccgaggaa      480
atcaccgatt ggcagctggc gtcgaatgcg gagcattcct cgaccgggct gcgttcggcc      540
gaggtcgagg cgctggaatc gctgccggat tccgaaatca aagacgcgct gcaggctttg      600
ccggaagaat tccggatggc ggtgtattac gccgatgtcg agggttttcc gtacaaggaa      660
atcgccgaga tcatggatac gccgattgga acggtaatgt cacggctgca ccgcggccga      720
cggcagctgc gtggcctgct ggccgacgtg gccaaggagc gcggtttcaa ccgcgggcag      780
cagacgcacg aggaggtgtc gtcatga                                         807
```

<210> SEQ ID NO 2
<211> LENGTH: 546
<212> TYPE: DNA
<213> ORGANISM: Mycobacterium avium

<400> SEQUENCE: 2

```
gtggctcgtg tggtcggcat ttccagggcg tccgggactg ccgaggccgc tctgatgaag      60
gcgctctacg acgaacacgc cgcggtgctg tggcgctacg cgctgcggct gaccggcgac      120
```

| gcgagccaat ccgaggatgt ggtgcaggag acgttgctgc gggcctggca gcatcccgag | 180 |
| gtcatcggcg acaccgagcg ctcggcccgg cgtggttgt tcacggtggc ccgcaacatg | 240 |
| atcatcgacg accggcgcag cgcgcggttc cgcaacgtgg tcggctcgac cgacaccgcg | 300 |
| ggggcgcccg aacagtccac gcccgacgag gtcaacgcgg cgctggaccg gttgctgatc | 360 |
| gccgacgcga tggcccagct gtcggccgag caccgcgccg tgatcgaacg gtcctactac | 420 |
| cgcggttgga ccaccgcgca gatagctaca gacctcggca tcgccgaggg aacggtgaag | 480 |
| tcgcgactac actatgcggt gcgggcgttg cgactcactc tgcaggaact cggggtcacc | 540 |
| cgatga | 546 |

```
<210> SEQ ID NO 3
<211> LENGTH: 756
<212> TYPE: DNA
<213> ORGANISM: Mycobacterium avium

<400> SEQUENCE: 3
```

| atggatcgcg gagcgcggga gaccgggaat accgaatggc agctgcctgt tgccgccaat | 60 |
| gacgaaatgc cgctgatcgg catgccgaat tcggaggaat tgatcatcac cacgcttttg | 120 |
| agcccgtcca gcatgtcgca cgcgcacgac ccttccgccg acgggtgggc ggagccgtcc | 180 |
| gacgggctgc agggcaccgc ggtcttcgac gcgaccggtg acaagacggc catgccgtcg | 240 |
| tgggacgagc tggtgcgcca gcacgccgac cgggtgtacc ggctggccta ccggcttttcc | 300 |
| ggcaatcagc acgacgccga ggacctcacc caggagacct tcatccgggt gttccggtcg | 360 |
| gtgcagaact accagccggg aaccttcgag ggctggctgc accgcatcac cacgaacctg | 420 |
| ttcctggaca tggtccgccg gcgctcgcgc atccggatgg aggcgctgcc cgaggactac | 480 |
| gagcgggtgc ccgccgacga gcccaatccc gaagagatct accacgattc gcggctcggc | 540 |
| cccgacctgc aggccgcgct ggactcgctg ccgccggagt tccgcgccgc ggtcgtgctg | 600 |
| tgcgacatcg agggcctgtc gtatgaggag atcggcgcga cgctgggggt gaagctgggc | 660 |
| accgtgcgca gccgcatcca ccgcggccgc caggccctgc gcgattacct ggccgcgcac | 720 |
| cccgaccacg acgcgctgcg cgcctcctcg gcgtag | 756 |

```
<210> SEQ ID NO 4
<211> LENGTH: 924
<212> TYPE: DNA
<213> ORGANISM: Mycobacterium avium

<400> SEQUENCE: 4
```

| atgacgcggg caccgaccgg cagcgagcac gccgaccgat tcaccctgct gcggccgctg | 60 |
| ctgttcacca tcgcctacga aatgctgggc tcggcgaccg aggccgacga cgtgttgcag | 120 |
| gacagctacc tgcgctggtc gaccgtcgac ctggccacgg tgcgcgacac caagtcctac | 180 |
| ctggctcagc tggtcacccg ccaggcgctc aacgcgctgc gggccggcgc gcgccggcgc | 240 |
| gaggagtacg tcgggccctg gctgcccgag ccgctgctgc tcgacgagca ggatccgtcc | 300 |
| accgatgtcg ttctcgccga gtcgatttcg atggcgatgc tggtgttgct ggaaacgttg | 360 |
| agtccagacg agcgggcggt gttcgtgctg cgtgaggtgt tcggattcga ctacgacgag | 420 |
| atcgccgagg cggtgggcaa gccggcgtcc accgtgcgtc aggtcgcgca ccgggcccgc | 480 |
| gaacacgtgc gggcccggcg caagcgccac cccggcgccg gcaggcgat cgaccccaag | 540 |
| cgcaacgccg agctcaccgc gcagttcctg gccacggcgg ccagcggcga cgtggaggcg | 600 |
| ctgatggcga tgctggcccc ggacgccacc tggaccgccg acagcggcgg cgtggtcagc | 660 |

```
gccgcccgca ggccggtggt cggcgccgag aaagtggccc gcgccatcac cgggctgttc        720
cgcaaggccg cggagtacgc caccctgcgg gtggacacgg tgacctgcaa cggcgccccg        780
gcggtgttgc tctacctcgg cgaccggctc gaaggcgtca tcacggtgga gatcgcggcg        840
gacaagatca ccaatttcta cgtgatgcgc aacccgcaca agctggcggc gctggccacc        900
gcccgcgacg tcagccgcgg ctga                                               924

<210> SEQ ID NO 5
<211> LENGTH: 998
<212> TYPE: DNA
<213> ORGANISM: Mycobacterium avium

<400> SEQUENCE: 5
ttgaacccga tgacagtaca agccgaacgg gaggtcgcta tggcgaacgc cagcacgagc         60
agatttgacg gcgatctgga tgctcaaagc cccgcagcgg acctggtgcg cgtgtatctg        120
aacgggatcg gtaagacggc gttgctgaat gcggctggcg aagtggaact cgcgaagcgc        180
atcgaagcgg ggctctacgc cgagcacctg ctcgaaacgc gtaagcgcct cggggagaac        240
cgcaaacgcg atctggaggc cgtggtgcgc gacggccagg ccgcgcgccg tcatctgctg        300
gaagcgaacc tgcgcctggt ggtgtcgctg gccaagcggt acacgggtcg cggcatgccg        360
ttgctggacc tgatccagga gggcaacctc gggctgatcc gggcgatgga aaagttcgac        420
tacacaaagg gattcaagtt ctcgacgtac gcgacgtggt ggatccgtca ggccatcacc        480
cgcggcatgg ccgaccagag ccgcaccatc cggctgccgg tgcacctggt cgagcaggtc        540
aacaagctgg cgcggatcaa gcgggagatc accagaacct gggccgcgag gccaccgacg        600
aggagctggc cgccgagtcg ggcatcccga tcgacaagat caacgacctg ctcgagcaca        660
gccgcgaccc ggtgagcctg gacatgccgg tgggctcgga ggaggaagcc ccgctgggcg        720
acttcatcga ggacgccgag gcgatgtccg ccgagaacgc ggtgatcgcc gagctgctgc        780
acaccgacat ccgcagcgtg ctggccaccc tggacgagcg cgagcaccag gtgatccggc        840
tgcggttcgg cctcgacgac ggccagccgc gcacgctgga ccagatcggc aagctgttcg        900
ggctgtcccg ggagcgggtc cgccagatcg agcgggacgt gatgtccaaa ctccgcaacg        960
gggagcgggc cgaccggcta cggtcgtacg cgagctga                                998
```